US011306103B2

(12) United States Patent
Lee et al.

(10) Patent No.: US 11,306,103 B2
(45) Date of Patent: Apr. 19, 2022

(54) THIENO[3,2-B]PYRIDINE-5(4H)-ONE DERIVATIVE COMPOUND, PREPARATION METHOD THEREOF AND USE THEREOF

(71) Applicant: Korea Institute of Ocean Science & Technology, Gyeonggi-do (KR)

(72) Inventors: Jong Seok Lee, Gyeonggi-do (KR); Dan Bi Sung, Seoul (KR); Bo Hyun Mun, Gyeonggi-do (KR); Hyi Seung Lee, Seoul (KR); Yeon Ju Lee, Gyeonggi-do (KR); Ji Hoon Lee, Seoul (KR); Hee Jae Shin, Gyeonggi-do (KR); Sol Park, Gyeonggi-do (KR)

(73) Assignee: Korea Institute of Ocean Science & Technology

( * ) Notice: Subject to any disclaimer, the term of this patent is extended or adjusted under 35 U.S.C. 154(b) by 19 days.

(21) Appl. No.: 16/768,251

(22) PCT Filed: Dec. 27, 2017

(86) PCT No.: PCT/KR2017/015585
§ 371 (c)(1),
(2) Date: May 29, 2020

(87) PCT Pub. No.: WO2019/107662
PCT Pub. Date: Jun. 6, 2019

(65) Prior Publication Data
US 2021/0171539 A1 Jun. 10, 2021

(30) Foreign Application Priority Data
Nov. 30, 2017 (KR) .................. 10-2017-0163722

(51) Int. Cl.
| | |
|---|---|
| *C07D 495/04* | (2006.01) |
| *C09K 11/00* | (2006.01) |
| *C07D 519/00* | (2006.01) |
| *C09K 11/06* | (2006.01) |
| *G01N 31/22* | (2006.01) |
| *G01N 33/533* | (2006.01) |

(52) U.S. Cl.
CPC ......... *C07D 495/04* (2013.01); *C07D 519/00* (2013.01); *C09K 11/06* (2013.01); *G01N 31/221* (2013.01); *G01N 33/533* (2013.01); *C09K 2211/1018* (2013.01)

(58) Field of Classification Search
CPC .... C07D 495/04; C09K 11/06; G01N 33/533; A61K 31/4365

USPC .............. 546/114; 252/301.16; 514/301
See application file for complete search history.

(56) References Cited

FOREIGN PATENT DOCUMENTS

KR 101736387 B1 5/2017

OTHER PUBLICATIONS

"Synthetic Study of Thieno[3,2-b]pyridin-5(4H)-one Derivatives," Thesis submitted to committee of the University of Science and Technology (2016).
Acharya et al., "Synthesis of Thieno-Fused Five- and Six-Membered Nitrogen and Oxygen Heterocycles via Intramolecular Heteroannulation of 4,5-Substituted 3-Amino or 3-Hydroxy 2-Functionalized Thiophenes," Journal of Organic Chemistry, 82:7920-7938 (2017).
Lee et al., "Reactions of 3-methylamino-5-phenylthiophene with $\alpha,\beta$ unsaturated esters and $\alpha,\beta$ unsaturated nitriles," Journal of Heterocyclic Chemistry, 37:363-372 (2000).
Queiroz et al., "New potential antitumoral di(hetero)arylether derivatives in the thieno[3,2-b]pyridine series: Synthesis and fluorescence studies in solution and in nanoliposomes," Journal of Photochemistry and Photobiology A: Chemistry, 238:71-80 (2012).
Sung et al., "Synthesis and Photophysical Properties of Fluorescent Thieno[3,2-b]pyridin-5(4H)-ones," 26th ISHC Congress (2017).

*Primary Examiner* — Charanjit Aulakh
(74) *Attorney, Agent, or Firm* — Foley Hoag LLP

(57) ABSTRACT

The present invention relates to a novel thieno[3,2-b]pyridine-5(4H)-one derivative compound, a preparation method thereof, and a use thereof. The novel thieno[3,2-b]pyridine-5(4H)-one derivative compound according to the present invention is synthesized via an aza-[3+3] cyclization addition reaction using BOP, wherein the compound is obtained by synthesizing a 4-arylthiophen-3-amine in which aryl groups such as 4-piperidyl-C6H4, 4-pyrrolidyl-C6H4, 4-MeOC6H4, 3,4,5-(MeO)3C6H4, C6H5, 4-C6H5C6H4, and 4-F3COC6H4 are introduced via a synthesis process by a bromination reaction, a hydrolysis reaction, a decarboxylation reaction, and a Suzuki coupling reaction of methyl 3-aminothiophene carboxylate, and by synthesizing 4-arylthiophen-3-amine and mono-methyl fumarate via a formal aza-[3+3] cyclization addition reaction using BOP and conjugation. Accordingly, novel thieno[3,2-b]pyridine-5(4H)-one derivative compounds according to the present invention have fluorescence properties with a wide range of emission wavelengths and thus may be utilized in various industrial fields such as physics, chemistry, and biomedical research.

8 Claims, 5 Drawing Sheets

THIENO[3,2-B]PYRIDINE-5(4H)-ONE DERIVATIVE COMPOUND, PREPARATION METHOD THEREOF AND USE THEREOF

RELATED APPLICATIONS

This application is the U.S. National Stage of International Application No. PCT/KR2017/015585, filed Dec. 27, 2017, which designates Korea, published in Korean, and claims priority under 35 U.S.C. §§ 119 or 365(c) to Korean Application No. 10-2017-0163722, filed Nov. 30, 2017. The entire teachings of the above applications are incorporated herein by reference.

TECHNICAL FIELD

Disclosed are a novel thieno[3,2-b] pyridine-5(4H)-one derivative compound, a preparation method therefor, and a use thereof.

BACKGROUND ART

A fluorophore is used for monitoring an analysis subject at a molecular or supermolecular level in a non-destructive manner. Recently, the development of detection and imaging technology has tended to make a focus on an increase in florescence sensitivity and spatial resolution. As a result, even a phenomenon of single molecules can be monitored in real time using high-quality fluorescence microscopy. Due to the applicability thereof to various industrial fields including biology, medical science, pharmacy, environmentology, and sitology, such technologies using fluorophores have high ripple effects in industries, inciting extensive research on the development of small molecule fluorophores having advanced photophysical properties. In particular, small molecule fluorophores offer several advantages including excellent synthetic accessibility complemented by the inherent structural versatility thereof, substantial flexibility to assemble components with a specific function, and high chemical stability, despite the small sizes thereof.

However, most of the currently available fluorophores suffer from the problems of temporary switching between fluorescent and non-fluorescent states (blinking), and irreversible destruction (photobleaching). Development is thus needed for a technology to solve these problems.

In order to develop organic fluorophores having a broad spectrum of emission wavelengths, account must be taken of the extent of the n-electron system in suitable substituents (auxochromes) for the central scaffold of the fluorophore selected. In addition, promoting a non-radioactive process in an excited state, and a photoinduced intramolecular charge transfer (ICT) process across the donoo-acceptor (D-A) type molecule system while suppressing the interal rotation is also another factor to be considered.

Generally, serving as fluorescent reporter molecules in designing molecular sensors, organic fluorescent substances provides chemical crues to various problems existing in nature. Therefore, there is a need for a fluorophore having more intensified and enhanced fluorescent properties although a wide range of pools of customized molecular sensors has been developed on the basis of suitable sets of fluorophore core scaffolds.

DETAILED DESCRIPTION OF THE INVENTION

Technical Problem

Leading to the present disclosure, intensive and thorough research into a novel fluorophore, conducted by the present inventors, resulted in the finding that novel thieno[3,2-b] pyridine-5(4H)-one derivative compounds synthesized herein have a wide range of emission wavelengths, thereby being applicable to physics, chemistry, and biomedical research and form a pool from which a suitable derivative compound with an emission wavelength of interest can be selected as needed.

Therefore, a purpose of the present disclosure is to provide a novel thieno[3,2-b] pyridine-5(4H)-one derivative compound.

Another purpose of the present disclosure is to provide a method of preparation of the novel thieno[3,2-b] pyridine-5(4H)-one derivative compound according to the present disclosure.

A further purpose of the present disclosure is to provide a fluorescent composition comprising the novel thieno[3,2-b] pyridine-5(4H)-one derivative compound according to the present disclosure, an enantiomer or diastereomer thereof, or an acid or base addition salt thereof as an active ingredient.

Still another purpose of the present disclosure is to provide a biomolecular labeling or analysis kit comprising the fluorescent composition of the present disclosure A still further purpose of the present disclosure is to provide a pH-sensing composition comprising the novel thieno[3,2-b] pyridine-5(4H)-one derivative compound according to the present disclosure, an enantiomer or diastereomer thereof, or an acid or base addition salt thereof as a fluorescent dye.

Yet another purpose of the present disclosure is to provide a pH sensor comprising the pH-sensing composition of the present disclosure.

Technical Solution

In order to achieve the purposes, an aspect of the present disclosure provides a novel thieno[3,2-b]pyridine-5(4H)-one derivative compound.

According to another aspect thereof, the present disclosure provides a method for preparing the novel thieno[3,2-b] pyridine-5(4H)-one derivative compound of the present disclosure.

According to a further aspect thereof, the present disclosure provides a fluorescent composition comprising the novel thieno[3,2-b] pyridine-5(4H)-one derivative compound according to the present disclosure, an enantiomer or diastereomer thereof, or an acid or base addition salt thereof as an active ingredient.

According to yet another aspect thereof, the present disclosure provides a biomolecular labeling or analyzing kit comprising the fluorescent composition of the present disclosure.

According to still another aspect thereof, the present disclosure provides a pH sensing composition comprising the novel thieno[3,2-b] pyridine-5(4H)-one derivative compound according to the present disclosure, an enantiomer or diastereomer thereof, or an acid or base addition salt thereof as a fluorescent dye.

According to a yet further aspect thereof, the present disclosure provides a pH sensor comprising the pH sensing composition of the present disclosure.

Advantageous Effects

The novel thieno[3,2-b] pyridine-5(4H)-one derivative compounds according to the present disclosure are prepared by aza-[3+3] cycloaddition using BOP. In this regard, 4-arylthiophen-3-amine is synthesized by introducing an aryl group such as 4-piperidyl-$C_6H_4$, 4-pyrrolidyl-$C_6H_4$, 4-MeO$C_6H_4$, 3,4,5-$(MeO)_3C_6H_4$, $C_6H_5$, 4-$C_6H_5C_6H_4$, 4-$F_3COC_6H_4$, and the like into methyl 3-aminothiophene carboxylate through a series of reactions including bromination, hydrolysis, decarboxylation, and Suzuki coupling reaction, and then subjected to formal aza-[3+3] cycloaddition and conjugation with mono-methyl fumarate, using BOP, to synthesize novel thieno[3,2-b]pyridine-5(4H)-one derivative compounds according to the present disclosure. Having fluorescence characteristics with a broad spectrum of emission wavelengths, the novel thieno[3,2-b] pyridine-5(4H)-one derivative compounds according to the present disclosure can find advantageous applications in a variety of industries including physical, chemical, and biomedical investigations.

BEST MODE FOR INVENTION

Figure 1:
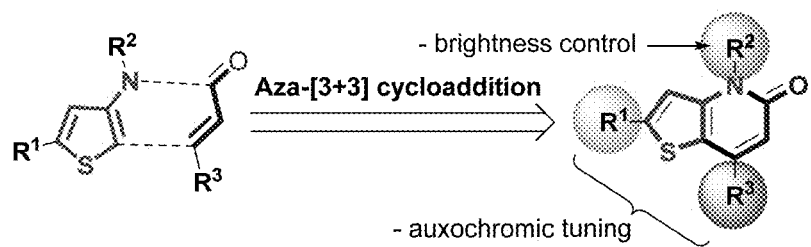
FIG. 1 is a schematic view illustrating a synthetic strategy for novel thieno[3,2-b] pyridine-5(4H)-one derivative compounds of the present disclosure through Aza-[3+3] cycloaddition.
Figure 2:
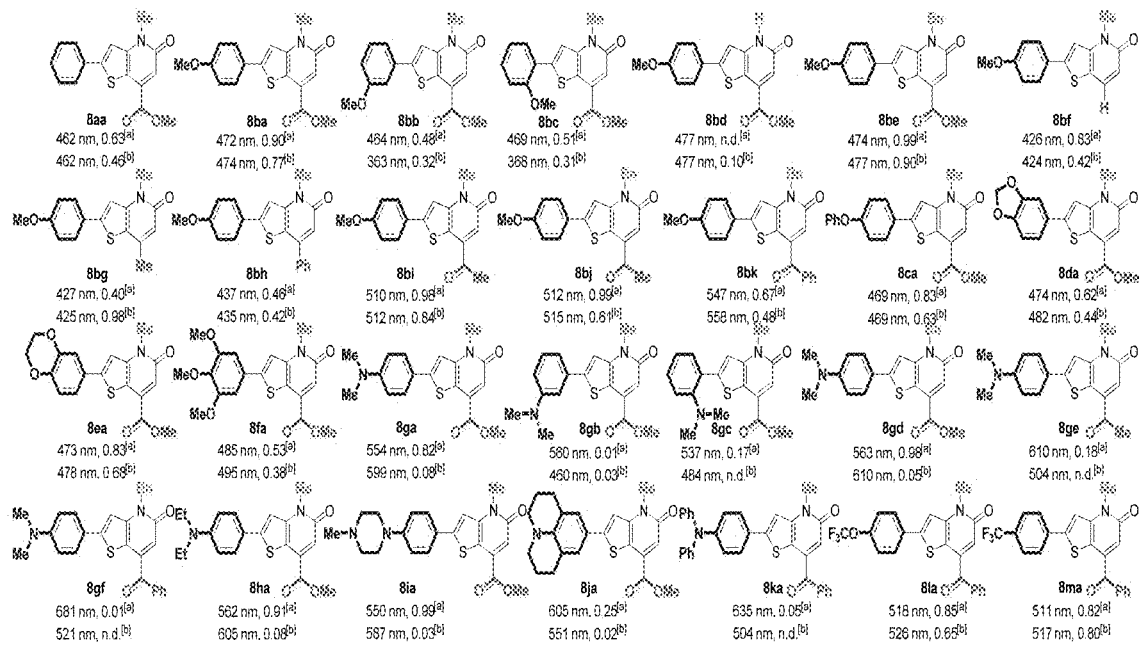
FIG. 2 shows structures and photophysical analysis data of novel thieno[3,2-b] pyridine-5(4H)-one derivative compounds synthesized in embodiments of the present disclosure.

The present disclosure provides a novel thieno[3,2-b]pyridine-5(4H)-one derivative compound represented by the following chemical formula, a enantiomer or diastereomer thereof, or an acid or base addition salt thereof.

<Chemical Formula>

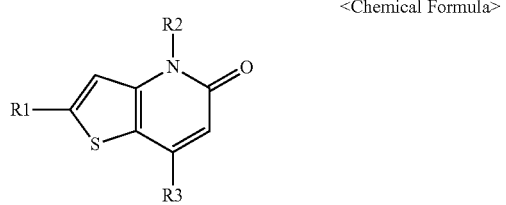

wherein,

R1 is an aryl of $C_6$-$C_{10}$ that may be substituted or unsubstituted with one or more substituents overlappingly selected from the group consisting of a linear or branched alkyl of $C_1$-$C_{10}$, an amine, a 5- or 6-membered aromatic or non-aromatic heterocylic ring amine bearing one or two N atoms, $F_3CO$—, an aryl of $C_6$-$C_{10}$, and an alkoxy of $C_1$-$C_4$, R2 is H, Me, or Bn, and R3 is

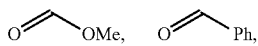

H, Me, or Ph.

As used herein, the term "linear alkyl" refers to a straight chain alkyl, wherein alkyl chain length is indicated by a range of numbers. In exemplary embodiments, "alkyl" refers to an alkyl chain as defined above containing 1, 2, 3, 4, 5, 6, 7, 8, 9, or 10 carbon atoms (i.e., $C_1$-$C_{10}$ alkyl). Examples of an alkyl group include, but are not limited to, methyl, ethyl, propyl, butyl, pentyl, and hexyl.

As used herein, the term "branched alkyl" refers to an alkyl chain wherein a branching point in the chain exists, and the total number of carbon atoms in the chain is indicated by a range of numbers. In exemplary embodiments, "branched alkyl" refers to an alkyl chain as defined above containing 3, 4, 5, 6, 7, 8, 9, or 10 carbon atoms (i.e, branched $C_3$-$C_{10}$ alkyl). Examples of branched alkyl include, but are not limited to, iso-propyl, iso-butyl, secondary-butyl, and tertiary-butyl.

The term "alkoxy" as used herein refers to —O-(alkyl), wherein "alkyl" is as defined above.

The term "aryl", as used herein, refers to a cyclic hydrocarbon where the ring is characterized by delocalized n electrons (aromaticity) shared among the ring members and wherein the number of ring atoms is indicated by a range of numbers. In exemplary embodiments, "aryl" refers to a cyclic hydrocarbon as described above containing 6, 7, 8, 9, or 10 ring atoms (i.e., $C_6$-$C_{10}$ aryl). Examples of an aryl group include, but are not limited to, benzene, naphthalene, tetralin, indene, and indane.

The term "heterocyclic amine", as used herein, refers to a cyclic amine which may be aromatic or non-aromatic and bears one or two N atoms as ring members wherein the number of ring atoms is indicated by a range of numbers. In exemplary embodiments, "heterocyclic amine" refers to a cyclic amine as defined above containing 5 or 6 ring atoms (i.e., 5- or 6-membered heterocyclic amine). Examples of heterocyclic amine include pyrrole, pyrazle, imidazole, pyridine, pyridazine, pyrimidine, piperidine, and pyrolidine, but are not limited thereto.

The novel thieno[3,2-b] pyridine-5(4H)-one derivative compounds according to the present disclosure are synthesized by aza-[3+3] cycloaddition using BOP. In this regard, 4-arylthiophen-3-amine is synthesized by introducing an aryl group such as 4-piperidyl-$C_6H_4$, 4-pyrrolidyl-$C_6H_4$, 4-MeO$C_6H_4$, 3,4,5-$(MeO)_3C_6H_4$, $C_6H_5$, 4-$C_6H_5C_6H_4$, 4-$F_3COC_6H_4$, and the like into methyl 3-aminothiophene carboxylate through a series of reactions including bromination, hydrolysis, decarboxylation, and Suzuki coupling reaction, and then subjected to formal aza-[3+3] cycloaddition and conjugation with mono-methyl fumarate, using BOB, to synthesize novel thieno[3,2-b]pyridine-5(4H)-one derivative compounds according to the present disclosure.

Concrete structures of the novel thieno[3,2-b]pyridine-5(4H)-one derivative compound synthesized by the method in exemplary embodiment of the present invention are summarized in the following table.

| | structure |
|---|---|
| 1 | 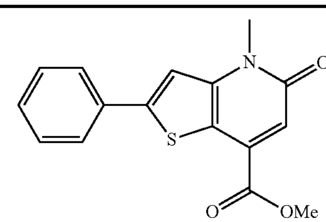 |

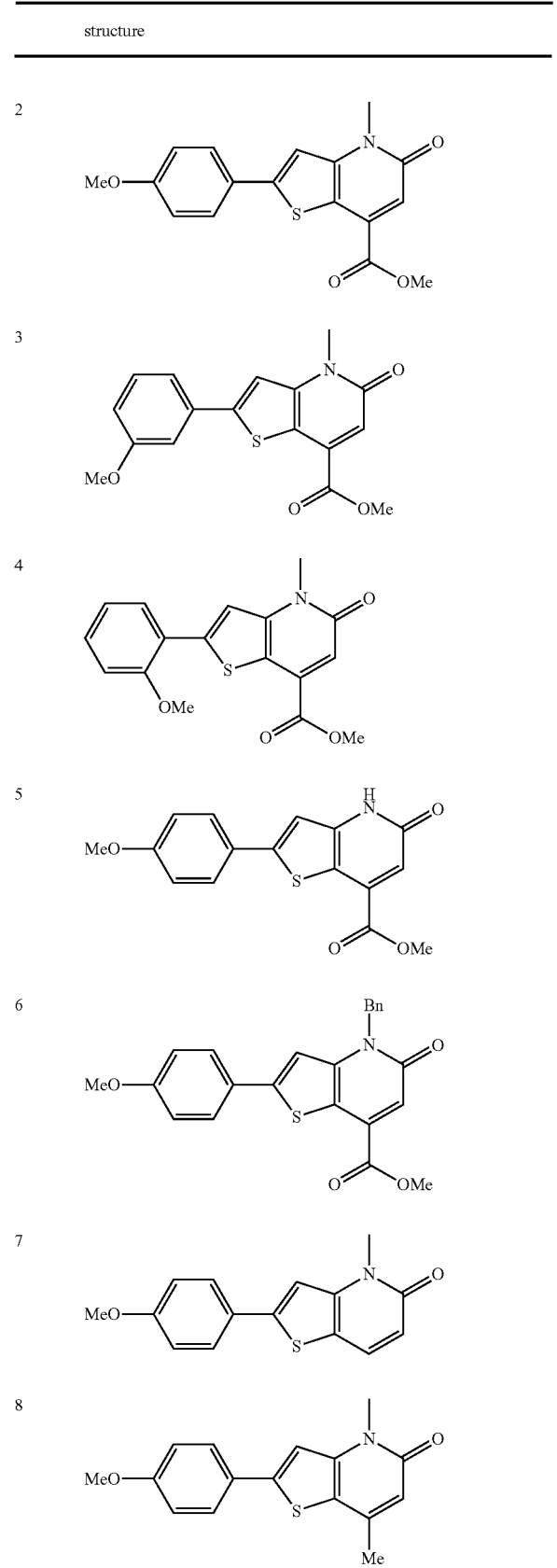
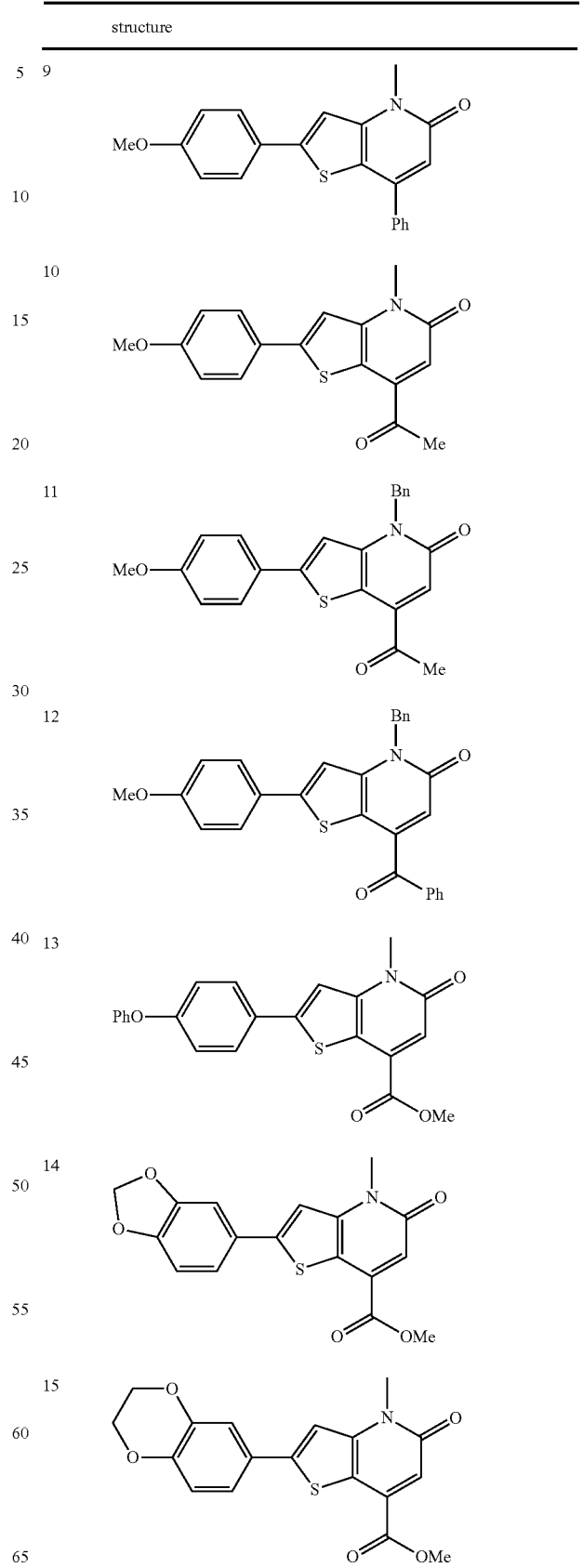

| | structure |
|---|---|
| 16 | 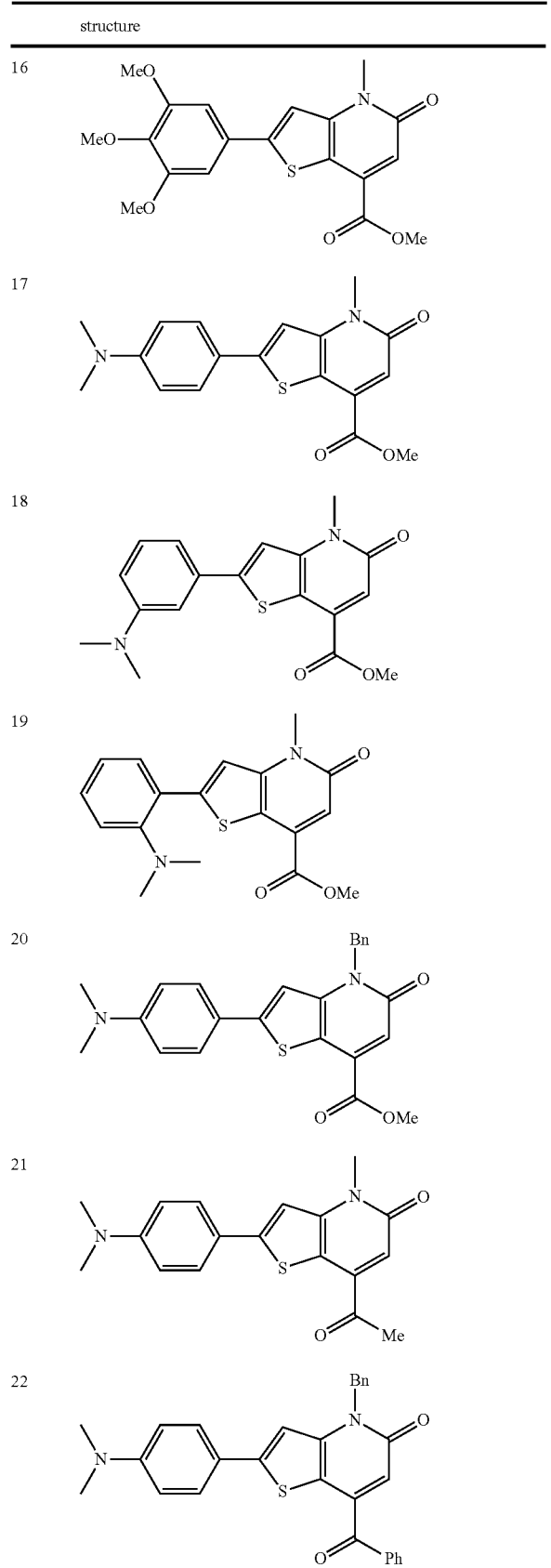 |
| 17 | 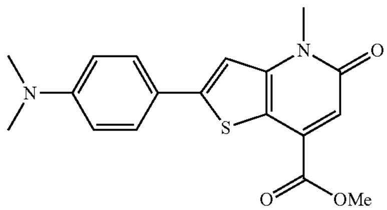 [SMILES: COC(=O)c1cc(=O)n(C)c2cc(-c3ccc(N(C)C)cc3)sc12] |
| 18 | 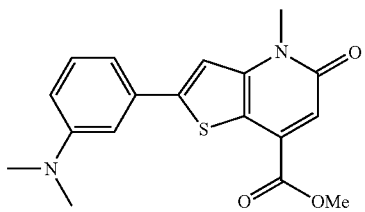 [SMILES: COC(=O)c1cc(=O)n(C)c2cc(-c3cccc(N(C)C)c3)sc12] |
| 19 | 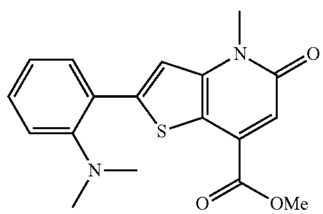 [SMILES: COC(=O)c1cc(=O)n(C)c2cc(-c3ccccc3N(C)C)sc12] |
| 20 | 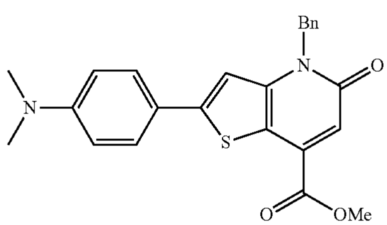 [SMILES: COC(=O)c1cc(=O)n(Cc2ccccc2)c2cc(-c3ccc(N(C)C)cc3)sc12] |
| 21 | 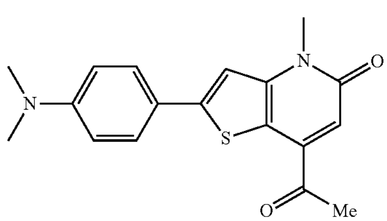 [SMILES: CC(=O)c1cc(=O)n(C)c2cc(-c3ccc(N(C)C)cc3)sc12] |
| 22 | 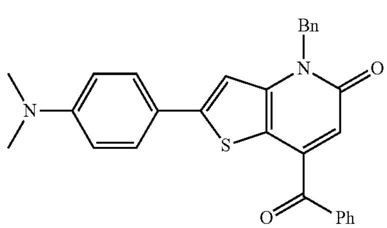 [SMILES: CN(C)c1ccc(-c2cc3c(s2)c(C(=O)c2ccccc2)cc(=O)n3Cc2ccccc2)cc1] |

| | structure |
|---|---|
| 23 | 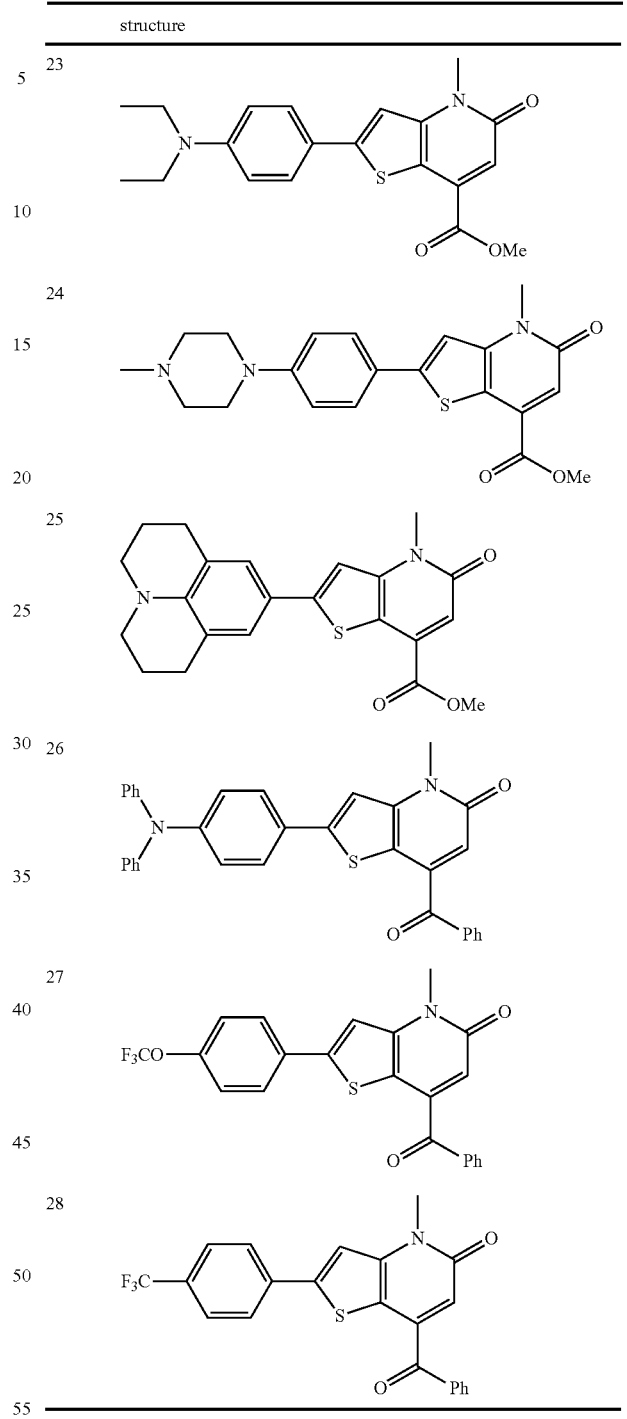 |
| 24 | 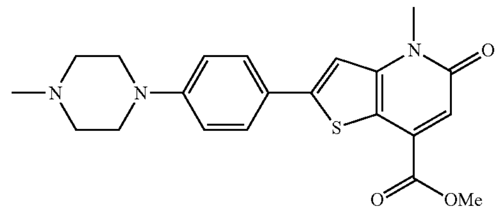 [SMILES: COC(=O)c1cc(=O)n(C)c2cc(-c3ccc(N4CCN(C)CC4)cc3)sc12] |
| 25 | 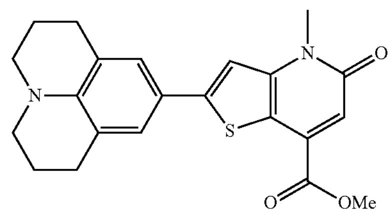 [SMILES: COC(=O)c1cc(=O)n(C)c2cc(-c3cc4c5c(c3)CCCN5CCC4)sc12] |
| 26 | 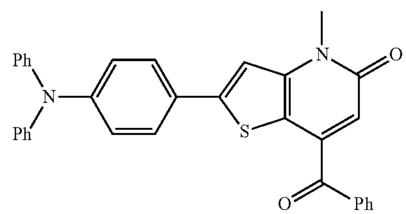 [SMILES: Cn1c(=O)cc(C(=O)c2ccccc2)c2sc(-c3ccc(N(c4ccccc4)c4ccccc4)cc3)cc21] |
| 27 | 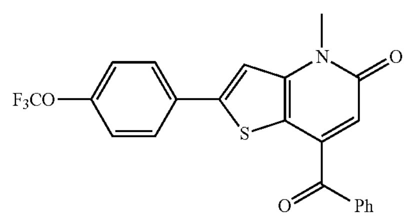 [SMILES: Cn1c(=O)cc(C(=O)c2ccccc2)c2sc(-c3ccc(OC(F)(F)F)cc3)cc21] |
| 28 | 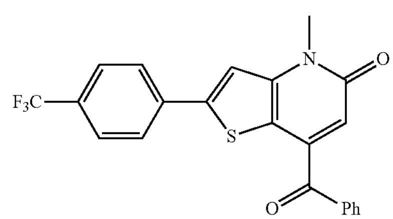 [SMILES: Cn1c(=O)cc(C(=O)c2ccccc2)c2sc(-c3ccc(C(F)(F)F)cc3)cc21] |

As used herein, the term "salt" is intended to embrace a pharmaceutically acceptable salt commonly used to form an alkali metal salt of a free acid and to form an addition salt of a free base. The nature of the salt is not critical, provided that it is pharmaceutically acceptable. Suitable pharmaceutically acceptable acid addition salts may be prepared from an inorganic acid or from an organic acid. Exemplary pharmaceutical salts are disclosed in the document [Stahl, P. H., Wermuth, C. G., Eds. *Handbook of Pharmaceutical Salts: Properties, Selection and Use*; Verlag Helvetica Chimica Acta/Wiley-VCH: Zurich, 2002], the contents of which are hereby incorporated by reference in their entirety. Specific, non-limiting examples of inorganic acids are hydrochloric acid, hydrobromic acid, hydroiodic acid, nitric acid, carbonic acid, sulfuric acid, and phosphoric acid. Appropriate organic acids include, without limitation, aliphatic, cycloaliphatic, aromatic, arylaliphatic, and heterocyclyl containing carboxylic acids and sulfonic acids, for example formic, acetic, propionic, succinic, glycolic, gluconic, lactic, malic, tartaric, citric, ascorbic, glucuronic, maleic, fumaric, pyruvic, aspartic, glutamic, benzoie, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, 3-hydroxybutyric, and galactaric or galacturonic acid. Suitable pharmaceutically acceptable salts of free acid-containing compounds disclosed herein include, without limitation, metallic salts and organic salts. Exemplary metallic salts include, but are not limited to, appropriate alkali metal (group Ia) salts, alkaline earth metal (group IIa) salts, and other physiological acceptable metals. Such salts can be made from aluminum, calcium, lithium, magnesium, potassium, sodium, and zinc. Exemplary organic salts can be made from primary amines, secondary amines, tertiary amines and quaternary ammonium salts, for example, tromethamine, diethylamine, tetra-N-methylammonium, N,N'-dibenzylethylenediamine, chloroprocaine, choline, diethanolamine, ethylenediamine, meglumine (N-methylglucamine), and procaine.

Structural, chemical and stereochemical definitions are broadly taken from IUPAC recommendations, and more specifically from Glossary of Terms used in Physical Organic Chemistry (IUPAC Recommendations 1994) as summarized by Muller, P. Pure Appl. Chem. 1994, 66, pp. 1077-1184 and Basic Terminology of Stereochemistry (IUPAC Recommendations 1996) as summarized by Moss, G. P. Pure Appl. Chem. 1996, 68, pp. 2193-2222.

An enantiomer is defined as one of a pair of molecular entities which are mirror images of each other and non-superimposable. A diastereomer is defined as a stereoisomer other than enantiomers. Diastereomers are stereoisomers not related as mirror images. Diastereoisomers are characterized by differences in physical properties, and by some differences in chemical behavior towards achiral as well as chiral reagents.

The novel thieno[3,2-b] pyridine-5(4H)-one derivative compounds represented by the chemical formula, provided by the present disclosure, can be prepared through one selected from the following reaction schemes 1 to 3. Detailed preparation methods are described in the following Examples.

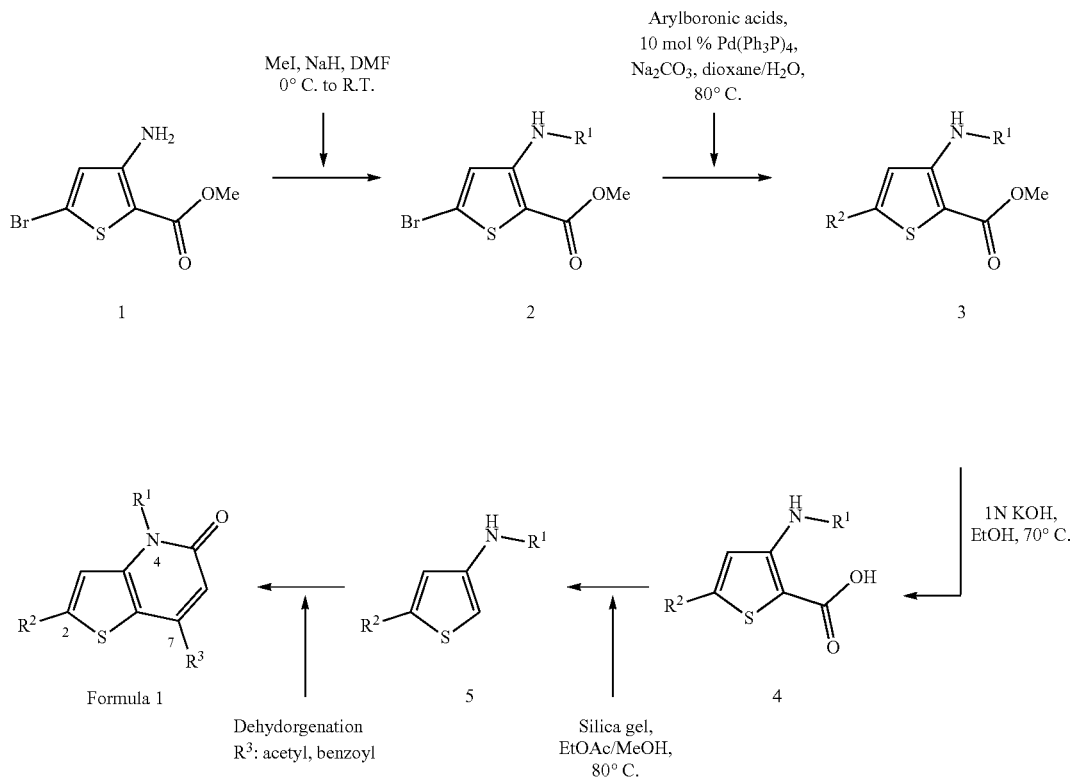

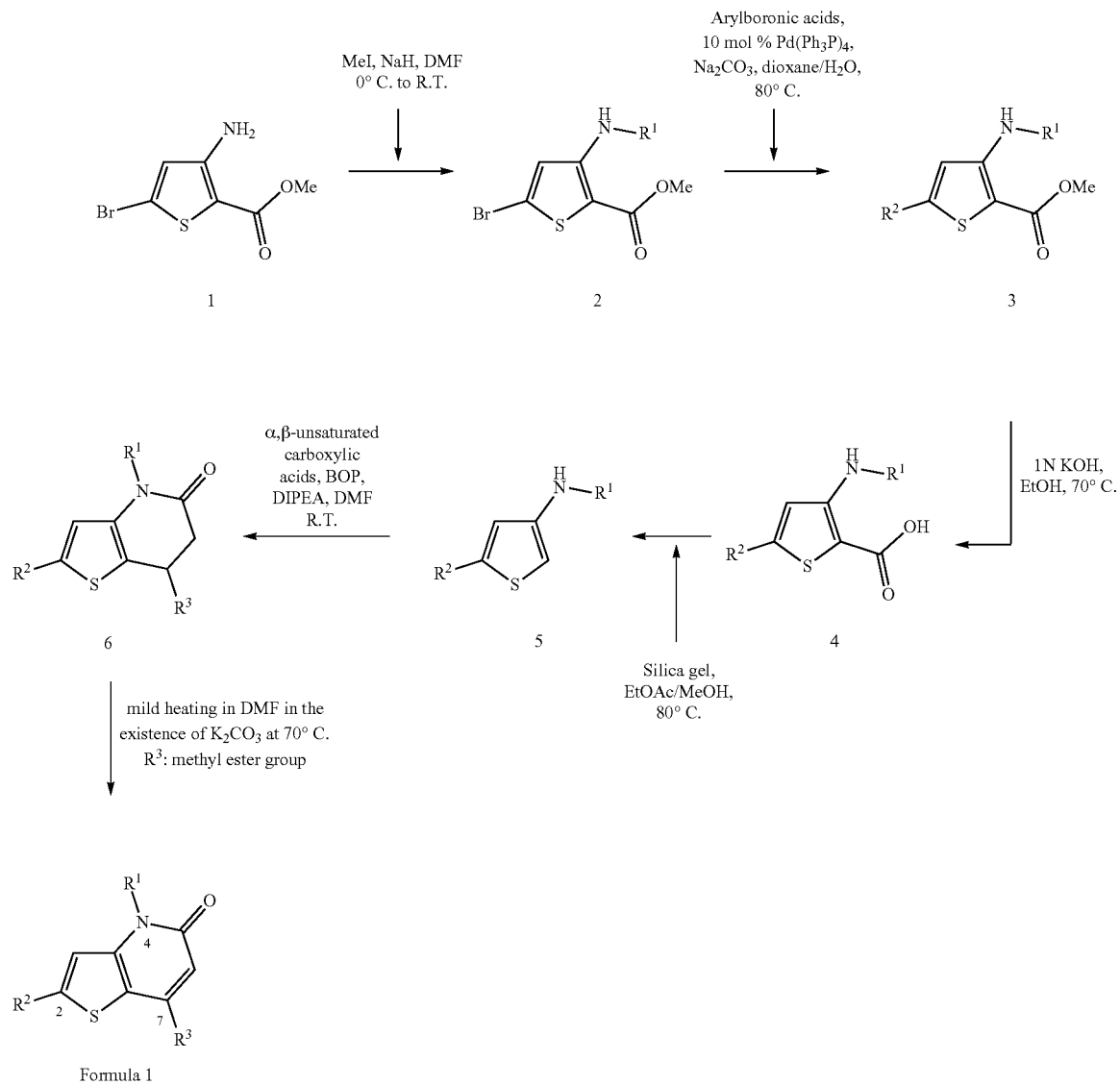
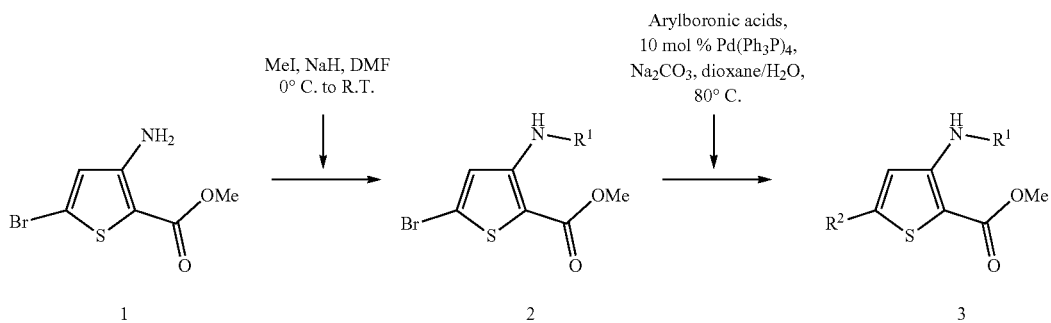

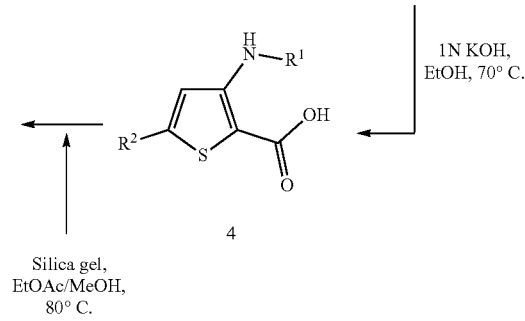
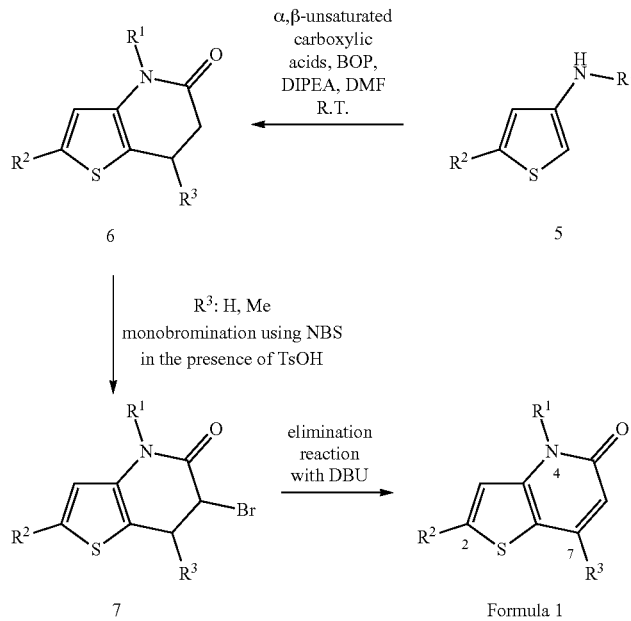

wherein,

R1 is H, Me, or Bn,

R2 is an aryl of $C_6$-$C_{10}$ that may be substituted or unsubstituted with one or more substituents overlappingly selected from the group consisting of a linear or branched alkyl of $C_1$-$C_{10}$, an amine, a 5- or 6-membered aromatic or non-aromatic heterocylic ring amine bearing one or two N atoms, $F_3CO-$, an aryl of $C_6$-$C_{10}$, and an alkoxy of $C_1$-$C_4$, and R3 is

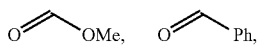

H, Me, or Ph.

In addition, the derivative compounds according to the present disclosure may be synthesized through the reaction schemes. Preferably, the compounds are synthesized through Reaction Scheme 1 for R3 substituent being an acetyl or a benzoyl (general ketone substituents), through Reaction Scheme 2 for R3 substituent being an ester, and through Reaction Scheme 3 for R3 substituent being H, an alkyl, or an aryl (heteroring, phenyl, substituted phenyl).

Of the derivative compounds synthesized in the Examples of the present disclosure, a synthesis was made of compounds 8ge, 8gf, 8bl, 8bj, 8bk, 8ka, 8la, and 8ma through Reaction Scheme 1, compounds 8aa, 8ba, 8bb, 8bc, 8bd, 8be, 8ea, 8fa, 8ga, 8gb, 8gc, 8gd, 8ha, 8ca, 8da, 8ia, and 8ja through Reaction Scheme 2, and compounds 8bf, 8bg, and 8bh through Reaction Scheme 3.

Furthermore, the present disclosure may provide a fluorescent composition comprising the novel derivative compound of the present disclosure, an enantiomer or diastereomer thereof, or an acid or base addition salt thereof as an active ingredient.

According to an embodiment of the present disclosure, analysis of fluorescence characteristics of the novel derivative compounds of the present disclosure revealed that the derivative compounds have emission wavelengths of 427 to 678 nm, which cover a broad spectrum of colors ranging from a blue color to a red color. From these derivative compounds, therefore, a selection may be advantageously made of a compound responsible for a color of interest among a blue to red color spectrum corresponding to 427 to 678 nm.

Moreover, the present disclosure may provide a biomolecular labeling or analyzing kit comprising the fluorescent composition of the present disclosure.

When used in biomolecular labeling or analysis, the fluorescent composition of the present disclosure can cover all the biomolecules found in organisms as target molecules. Having high fluoroluminescent characteristics and a broad spectrum of emission wavelengths, the novel derivative compounds of the present disclosure enable the detection and analysis of target molecules at higher sensitivity and accuracy.

In addition, the fluorescent composition of the present disclosure may be used to stain biospecimens such as cells, tissues, nucleic acids, and so on.

The present disclosure may also provide a pH-sensing composition comprising the novel derivative compound of the present disclosure, an enantiomer or diastereomer thereof, or an acid or base addition salt thereof as a fluorescent dye, and a pH sensor comprising the pH-sensing composition.

According to an embodiment of the present disclosure, fluorescent intensities of the derivative compounds in different pH ranges were analyzed. As a result, the novel derivative compounds of the present disclosure was found to exhibit high fluorescent intensities at characteristic pH ranges different from one compound to another. Therefore, the novel derivative compounds of the present disclosure can be used as pH-sensing sensors.

A better understanding of the present disclosure may be obtained through the following examples which are set forth to illustrate, but are not to be construed as limiting the present disclosure.

MODE FOR CARRYING OUT THE INVENTION

<Reagents and Instruments>

Anhydrous solvents, boric acid, and other chemical reagents were all purchased from Sigma Aldrich, Alfa Aesar, and TCI. The starting material methyl 3-amino-5-bromothiophene-2-carboxylate was purchased from Matrix Scientific Co. Organic reactions were monitored by thin-layer chromatography (TLC) on a 0.25 mm-thick, precoated silicagel plate (Kieselgel 60F254). Flash column chromatography was performed using an organic solvent on silica gel (70-230 mesh). In addition, $^1$H and $^{13}$C spectra recorded on Varian Unity-Inova 500 MHz and Bruker 600 MHz spectrometers. Chemical shift values were reported in δ (ppm) relative to chloroform (CDCl$_3$, δ 7.26) and dimethylsulfoxide (DMSO-d$_6$, δ 2.50). Coupling constants were expressed in Hz unit. Molecular weights were measured by liquid chromatography-mass spectrometry (LC-MS) using a ThermoRiningan spectrometer. Photophysical properties (UV-vis spectra, emission, excitation, quantum yield, and molecular coefficient) were obtained using Scinco 3000 spectrophotometer and fluorescence spectrophotometer (1 cm quartz cell).

Example 1

Synthesis of Novel Thieno[3,2-b]pyridine-5(4H)-one Derivative Compounds

The present inventors synthesized novel thieno[3,2-b]pyridine-5(4H)-one) derivative compounds through the following strategies. Synthesis processes for novel individual derivative compounds are illustrated as follows:

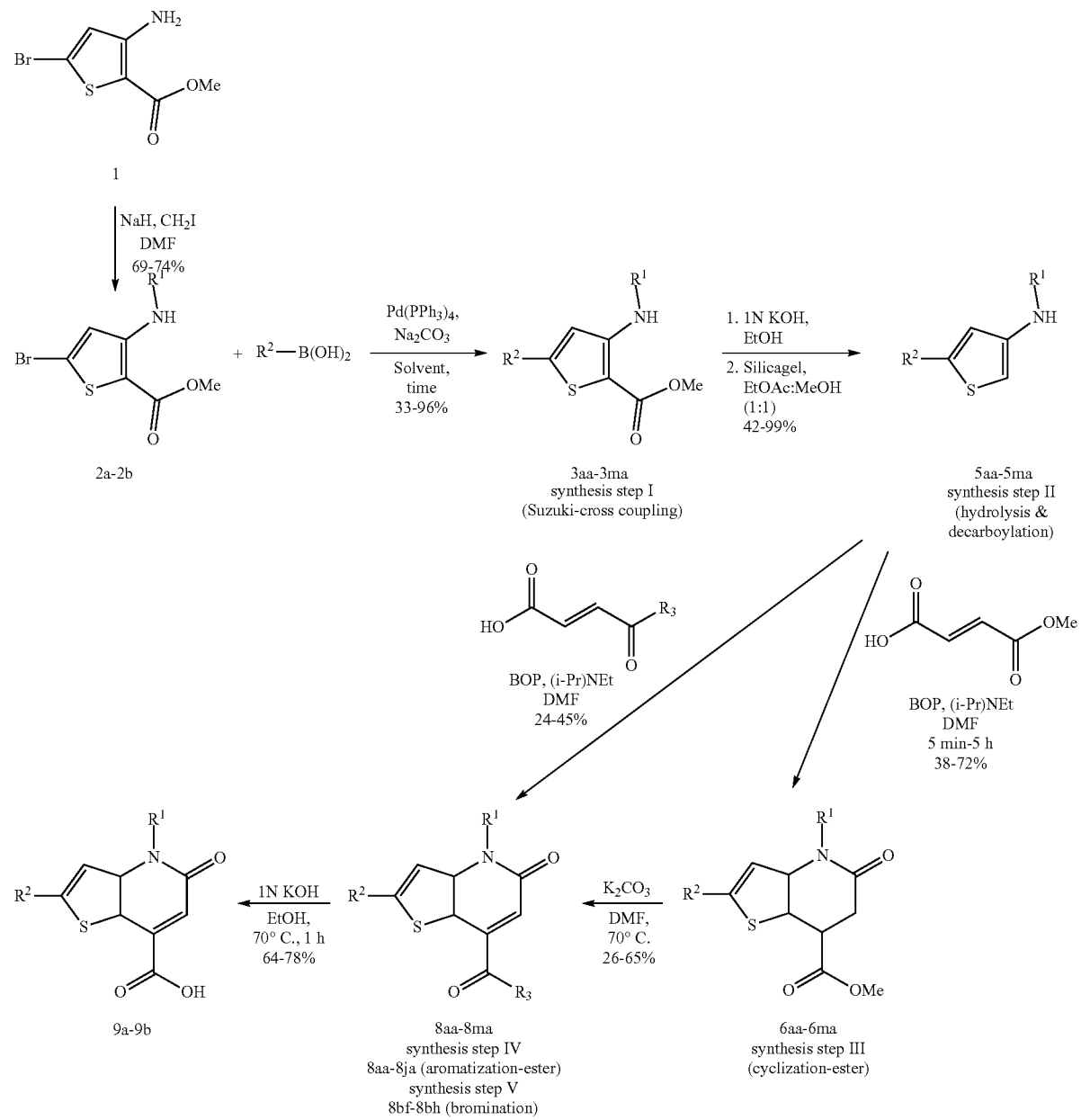

R$_1$ = H, Me, Bn
R$_2$ = various derivatives
R$_3$ = Me, OMe, Ph

General Reaction Scheme for Synthesis of Novel Derivative Compounds

<1-1> Suzuki Cross Coupling Reaction (3aa-3ma Synthesis Step I)

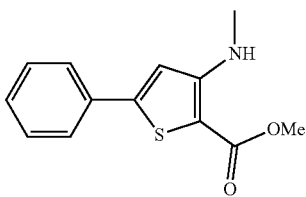 [SMILES: CNc1cc(-c2ccccc2)sc1C(=O)OC]

Methyl 3-(methylamino)-5-phenylthiophene-2-carboxylate (3aa)

Structureal formula 3aa represents an exemplary compound for illustrating the Suzuki cross coupling reaction. Compounds 3aa-3ma were synthesized through the Suzuki cross coupling reaction. For compound 3aa of the structural formula, phenyl boronic acid (146 mg, 1.20 mmol, 1.2 eq.), Pd(PPh$_3$)$_4$ (50.9 mg, 0.0500 mmol, 0.05 eq.), and a solution of sodium carbonate (127 mg, 1.20 mmol, 1.2 equiv.) in distilled water (1 ml) were added to a solution of 2a (methyl 5-bromo-3-(methylamino)thiophene-2-carboxylate; 250 mg, 1.00 mmol, 1.0 equiv.) in toluene (2.5 mL, 0.25M). Then, the mixture was subjected to the reaction while being heated to 110° C. and stirred for 5 hours. Subsequently, 5 ml of distilled water was added. Thereafter, the crude product was extracted three times with ethyl acetate (EtOAc (4 mL)). The organic layer thus formed was dried over Na$_2$SO$_4$, filtered, and evaporated in a vacuum. The residue was purified by flash column chromatography (hexane/EtOAc=4/1, v/v) on silica to afford compound 3aa as a pale yellow solid (128 mg, 0.517 mmol, 52%).

NMR data for compound 3aa are given as follow:
$^1$H NMR (600 MHz, CDCl$_3$) δ 7.64-7.62 (m, 2H), 7.41-7.39 (m, 2H), 7.34-7.34 (m, 1H), 6.85 (s, 1H), 6.68 (br s, 1H), 3.83 (s, 3H), 3.02 (s, 3H); $^{13}$CNMR (150 MHz, CDCl$_3$) δ 165.3, 157.5, 149.8, 133.7, 129.00, 128.99, 126.1, 111.7, 97.5, 51.1, 31.7.

<1-2> Hydrolysis and Decarboxylation (5aa-5ma Synthesis Step II)

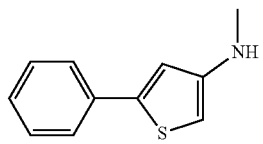

N-Methyl-5-phenylthiophen-3-amine (5aa)

Structural formula 5aa represents an exemplary compound for illustrating hydrolysis and decarboxylation reactions. Compounds 5aa-5ma were synthesized through hydrolysis and decarboxylation reactions. For compound 5aa of the structural formula, 1N KOH (2 mL) was added to a solution of 3aa (150 mg, 0.600 mmol, 1.0 eq.) in ethanol (4 mL, 0.25M). The mixture was heated to 70° C. and stirred for 1 hour. After completion of the reaction, the solvent was evaporated. Then, the crude product was reacted with silica gel without further purification. Silica gel (750 mg, 500 wt % of substrate) was added to an EtOAc (2 mL) and MeOH (2 mL) solution (1:1), and the reaction mixture was heated to 60° C. and stirred for 2 hours, followed by filtering out the silica gel and evaporating the organic layer in a vacuum. The residue was purified by flash column chromatography (hexane/EtOAc=3/1, v/v) on silica to afford compound 5aa as a white solid (105 mg, 0.555 mmol, 92%).

NMR data for compound 5aa are given as follow:
$^1$H NMR (600 MHz, CDCl$_3$) δ 7.59-7.57 (m, 2H), 7.37 (td, J=7.2 Hz and J=1.8 Hz, 2H), 7.28 (tt, J=7.2 Hz and J=1.5 Hz, 1H), 6.86 (d, J=1.8 Hz, 1H), 5.95 (d, J=1.8 Hz, 1H), 3.48 (br s, 1H), 2.85 (s, 3H); $^{13}$CNMR (150 MHz, CDCl$_3$) δ 150.3, 143.6, 134.7, 128.9, 127.6, 125.6, 116.0, 95.0, 32.7; LRMS (APCI): m/z calcd for C$_{11}$H$_{12}$NS [M+H]$^+$ 190.07, found 189.93.

<1-3> Cyclization-Esterification Reaction (6aa-6ja Synthesis Step III)

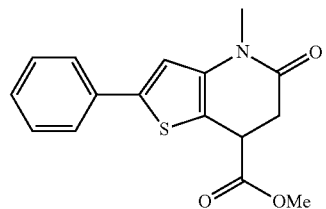 [SMILES: COC(=O)C1CC(=O)N(C)c2cc(-c3ccccc3)sc21]

Methyl 4-methyl 5-oxo-2 phenyl 4,5,6,7-tetrahydrothieno[3,2-b]pyridine-7-carboxylate (6aa)

Structural formula 6aa represents an exemplary compound for illustrating cyclization-esterification. Compounds 6aa-6ja were synthesized through cyclization-esterification. For compound 6aa of the structural formula, monomethyl fumarate (25.0 mg, 0.186 mmol, 1.2 equiv), (benzotriazol-1-yoxy)tris(dimethyl amino)phosphonium hexafluorophosphate (BOP, 83.0 mg, 0.186 mmol, 1.2 equiv), and N,N-diisopropylethylamine (67.0 μL, 0.388 mmol, 1.2 equiv) were added to a solution of 5aa (29.4 mg, 0.155 mmol, 1.0 equiv) in DMF (1.5 mL, 0.1M) were added. The reaction was stirred for 5 min at room temperature. After completion of the reaction, water (2 mL) was added. The crude product was extracted with EtOAc (3 mL) three times. The organic layer was dried over Na$_2$SO$_4$, filtered, and evaporated in a vacuum. The residue was purified by flash column chromatography (Hexane/EtOAc=1/1, v/v) on silica to afford compound 6aa as a pale yellow solid (21.2 mg, 0.0703 mmol, 45%).

NMR data for compound 6aa are given as follow:
$^1$H NMR (600 MHz, CDCl$_3$) δ 7.56 (d, J=7.8 Hz, 2H), 7.39 (t, J=12.5 Hz, 2H), 7.31 (t, J=6.9 Hz, 1H), 6.99 (s, 1H), 4.03 (t, J=7.2 Hz, 1H), 3.79 (s, 3H), 3.36 (s, 3H), 3.03 (ddd, J=7.7 Hz, J=16.2 Hz and J=31.5 Hz, 2H); $^{13}$CNMR (150 MHz, CDCl$_3$) δ 171.3, 167.2, 143.9, 140.4, 133.8, 129.2, 128.2, 125.6, 113.3, 112.5, 52.9, 38.4, 34.4, 30.6; LRMS (APCI): m/z calcd for C$_{16}$H$_{14}$NO$_3$S [M−H]$^-$ 300.07, found 300.50.

<1-4> Aromatization-Esterification (8aa-8ja Synthesis Step IV)

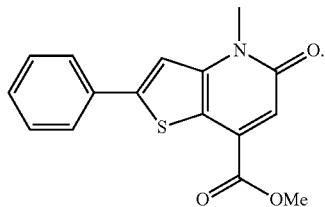 [SMILES: COC(=O)c1cc(=O)n(C)c2cc(-c3ccccc3)sc12]

Methyl 4-methyl-5-oxo-2-phenyl-4,5-dihydrothieno [3,2-b] pyridine-7-carboxylate (8aa)

Structural formula 8aa represents an exemplary compound for illustrating aromatization-esterification. Compounds 8aa-8ja were synthesized through aromatization-esterification. For compound 8aa of the structural formula, potassium carbonate (14.0 mg, 0.100 mmol, 1.5 equiv.) was added to a solution of 6aa (20.2 mg, 0.0670 mmol, 1.0 equiv.) in DMF (0.7 mL, 0.25M). Then, the reaction was heated to 70° C. and stirred for 1 hour. After completion of the reaction, water (1 mL) was added. The crude product was extracted with EtOAc (1 mL) three times. The organic layer was dried over $Na_2SO_4$, filtered, and evaporated in a vacuum. The residue was purified by flash column chromatography (Hexane/EtOAc=1/1, v/v) on silica to afford compound 8aa as a yellow solid (9.60 mg, 0.0320 mmol, 48%).

NMR data for compound 8aa are given as follow:
$^1$H NMR (600 MHz, $CDCl_3$) δ 7.72 (d, J=7.2 Hz, 2H), 7.46 (t, J=7.5 Hz, 2H), 7.41 (t, J=7.2 Hz, 1H), 7.27 (s, 1H), 7.23 (s, 1H), 4.02 (s, 3H), 3.79 (s, 3H); $^{13}$CNMR (150 MHz, $CDCl_3$) δ 165.1, 162.4, 151.3, 145.8, 134.1, 133.4, 129.5, 129.4, 126.4, 119.0, 115.7, 111.3, 53.3, 32.4.

<1-5> Bromination (8bf-8bh Synthesis Step V)

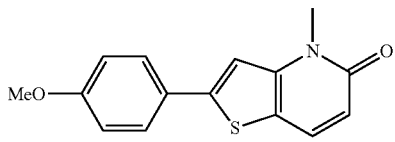 [SMILES: COc1ccc(-c2cc3c(ccc(=O)n3C)s2)cc1]

2-(4-Methoxyphenyl)-4-methylthieno[3,2-b]pyridine-5(4H)-one (8bf)

Structural formula 8bf represents an exemplary compound for illustrating bromination. Compounds 8bf-8bh were synthesized through bromination. For compound 8bf of the structural formula, N-bromosuccinimide (28.0 mg, 0.193 mmol, 1.1 eq.) was added to a solution of 6bf (37.9 mg, 0.139 mmol, 1.0 eq.) in DCM (1.5 mL, 0.25M) at 0° C. Subsequently, the mixture was warmed up to room temperature and stirred for 18 hours. After completion of the reaction, water (2 mL) was added. The crude product was extracted three times with DCM (2 mL). The organic layer was dried over $Na_2SO_4$, filtered, and evaporated in a vacuum. The residue was purified by flash column chromatography (hexane/EtOAc=1/2, v/v) on silica to afford compound 8bf as a white solid (16.9 mg, 0.0623 mmol, 45%).

NMR data for compound 8aa are given as follow:
$^1$H NMR (600 MHz, $CDCl_3$) δ 7.63 (d, J=9.0 Hz, 1H), 7.58 (d, J=8.4 Hz, 2H), 7.12 (s, 1H), 6.95 (d, J=8.4 Hz, 2H), 6.56 (d, J=9.0 Hz, 1H), 3.85 (s, 3H), 3.73 (s, 3H); $^{13}$CNMR (150 MHz, $CDCl_3$) δ 162.4, 160.6, 148.9, 145.0, 133.1, 127.6, 126.0, 117.3, 116.6, 114.7, 110.9, 55.6, 32.0; LRMS (APCI): m/z calcd for $C_{15}H_{14}NO_2S$ $[M+H]^+$ 272.07, found 271.88.

Example 2

Synthesis of Novel Thieno[3,2-b] pyridine-5(4H)-one(thieno[3,2-b]pyridine-5(4H)-one) Derivative Compounds

<2-1> Synthesis of Methyl 5-bromo-3-(methylamino)thiophene-2-carboxylate (2a)

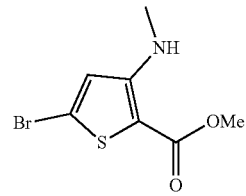

Methyl 5-bromo-3-(methylamino)thiophene-2-carboxylate (2a)

To a solution of methyl 3-amino-5-bromothiophene-2-carboxylate 1 (1.00 g, 4.24 mmol, 1.0 equiv) in DMF (40 mL) was added NaH (60% in mineral oil dispersion, 237 mg, 11.9 mmol, 1.4 equiv) at 0° C. After the mixture was stirred for 10 min, methyl iodide (343 μL, 5.51 mmol, 1.3 equiv) was added and warmed up to room temperature. The reaction was stirred for 18 h at room temperature. To quench the reaction, water (50 mL) was added and extracted three times with EtOAc (50 mL). The organic layer was dried over $Na_2SO_4$, filtered, and evaporated in a vacuum. The crude product was purified by flash column chromatography (hexane/EtOAc=30/1, v/v) on silica to afford the product 2a as a white solid.

NMR data for compound 2a are given as follow:
$^1$H NMR (600 MHz, $CDCl_3$) δ 6.67 (br s, 1H), 6.63 (s, 1H), 3.78 (s, 3H), 2.93 (d, J=5.5 Hz, 3H); $^{13}$CNMR (150 MHz, $CDCl_3$) δ 164.4, 156.5, 121.8, 119.5, 99.2, 51.3, 31.7.

<2-2> Synthesis of Methyl 3-(benzylamino)-5-bromothiophene-2-carboxylate (2b)

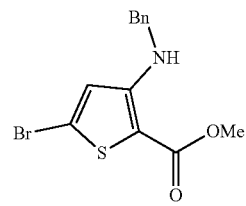 [SMILES: COC(=O)c1sc(Br)cc1NCc1ccccc1]

Methyl 3-(benzylamino)-5-bromothiophene-2-carboxylate (2b)

To a solution of methyl 3-amino-5-bromothiophene-2-carboxylate 1 (2.00 g, 8.47 mmol, 1.0 equiv) in DMF (85 mL) was added NaH (60% in mineral oil dispersion, 499 mg, 11.9 mmol, 1.4 eq.) at 0° C. After being stirred for 10 min, the mixture was added with benzyl bromide (1.59 g, 9.32 mmol, 1.1 eq.), warmed up to room temperature, and stirred for 3 hours at the temperature. To quench the reaction, water (100 mL) was added, followed by three rounds of extraction with EtOAc (100 mL). The organic layer was dried over $Na_2SO_4$, filtered, and evaporated in a vacuum. The crude product was purified by flash column chromatography (Hexane/EtOAc=20/1, v/v) on silica to afford the product 2a as a white solid (1.71 g, 5.24 mmol, 62%).

NMR data for compound 2b are given as follow:
$^1$H NMR (600 MHz, CDCl$_3$) δ 7.31-7.29 (m, 2H), 7.25-7.20 (m, 3H), 6.54 (d, J=1.2 Hz, 1H), 4.38 (d, J=4.2 Hz, 2H), 3.75 (s, 3H); $^{13}$CNMR (150 MHz, CDCl$_3$) δ 164.3, 155.4, 138.5, 128.9, 127.6, 127.0, 121.8, 119.9, 100.1, 51.3, 49.0; LRMS (APCI): m/z calcd for $C_{13}H_{13}BrNO_2S$ [M+H]$^+$ 325.99, found 325.99.

<2-3> Synthesis of Methyl 5-(4-methoxyphenyl)-3-(methylamino)thiophene-2-carboxylate (3ba)

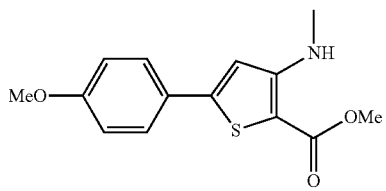 [SMILES: CNc1cc(-c2ccc(OC)cc2)sc1C(=O)OC]

Methyl 5-(4-methoxyphenyl)-3-(methylamino)thiophene-2-carboxylate (3ba)

Compound 2a (600 mg, 2.40 mmol, 1.0 equiv.), 4-methoxyphenylboronic acid (437 mg, 1.84 mmol, 1.2 equiv.), Pd(PPh$_3$)$_4$ (139 mg, 0.12 mmol, 0.05 equiv.), 0.4M sodium carbonate (7.2 mL), and toluene (9.6 mL) were used in a similar manner to synthesis step I of Example 1 to afford compound 3ba as a pale yellow solid (404 mg, 1.46 mmol, 61%). NMR data for compound 3ba are given as follow:
$^1$H NMR (600 MHz, CDCl$_3$) δ 7.56 (dd, J=6.9 Hz and J=2.1 Hz, 2H), 6.92 (dd, J=6.9 Hz and J=2.1 Hz, 2H), 6.75 (s, 1H), 3.84 (s, 3H), 3.82 (s, 3H), 3.02 (s, 3H); $^{13}$CNMR (150 MHz, CDCl$_3$) δ 165.4, 160.5, 157.7, 150.0, 127.5, 126.5, 114.4, 110.7, 96.7, 55.5, 51.1, 31.8; LRMS (APCI): m/z calcd for $C_{14}H_{16}NO_3S$ [M+H]$^+$ 278.09, found 277.88.

<2-4> Synthesis of Methyl 5-(3-methoxyphenyl)-3-(methylamino)thiophene-2-carboxylate (3bb)

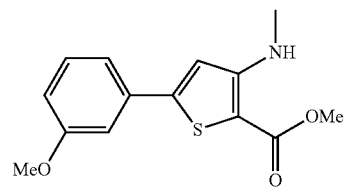 [SMILES: CNc1cc(-c2cccc(OC)c2)sc1C(=O)OC]

Methyl 5-(3-methoxyphenyl)-3-(methylamino)thiophene-2-carboxylate (3bb)

Compound 2a (300 mg, 1.20 mmol, 1.0 equiv.), 3-methoxyphenyl boronic acid (219 mg, 1.44 mmol, 1.2 equiv.), Pd(PPh$_3$)$_4$ (69.3 mg, 0.06 mmol, 0.05 equiv.), 0.4M sodium carbonate (3 mL), and toluene (4.8 mL) were used in a similar manner to synthesis step I of Example 1 to afford compound 3bb as a pale yellow solid (218 mg, 0.786 mmol, 66%). NMR data for compound 3bb are given as follow:
$^1$H NMR (500 MHz, CDCl$_3$) δ 7.30 (t, J=8.0 Hz, 1H), 7.22 (dt, J=7.5 Hz and J=1.1 Hz, 1H), 7.14 (t, J=2.0 Hz, 1H), 6.90 (dd, J=2.5 Hz and J=8.0 Hz, 1H), 6.84 (s, 1H), 6.66 (br s, 1H), 3.85 (s, 3H), 3.82 (s, 3H), 3.02 (d, J=5.5 Hz, 3H); $^{13}$CNMR (125 MHz, CDCl$_3$) δ 165.4, 157.6, 151.2, 150.9, 134.5, 129.7, 114.6, 113.3, 111.7, 110.0, 97.2, 51.2, 40.7, 31.8; LRMS (APCI): m/z calcd for $C_{14}H_{16}NO_3S$ [M+H]$^+$ 278.09, found 277.86.

<2-5> Synthesis of Methyl 5-(2-methoxyphenyl)-3-(methylamino)thiophene-2-carboxylate (3bc)

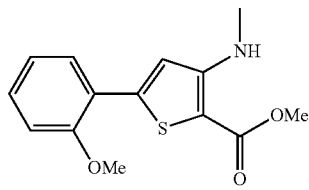 [SMILES: CNc1cc(-c2ccccc2OC)sc1C(=O)OC]

Methyl 5-(2-methoxyphenyl)-3-(methylamino)thiophene-2-carboxylate (3bc)

Compound 2a (300 mg, 1.20 mmol, 1.0 equiv.), 2-methoxyphenyl boronic acid (219 mg, 1.44 mmol, 1.2 equiv.), Pd(PPh$_3$)$_4$ (69.3 mg, 0.06 mmol, 0.05 equiv.), 0.4M sodium carbonate (3 mL), and toluene (4.8 mL) were used in a similar manner to synthesis step I of Example 1 to afford compound 3bc as a pale yellow solid (217 mg, 0.782 mmol, 65%). NMR data for compound 3bc are given as follow:
$^1$H NMR (500 MHz, CDCl$_3$) δ 7.67 (dd, J=7.5 Hz and J=1.5 Hz, 1H), 7.32 (t, J=7.8 Hz, 1H), 7.05 (s, 1H), 7.02-6.98 (m, 2H), 6.70 (br s, 1H), 3.95 (s, 3H), 3.83 (s, 3H), 3.03 (s, 3H); $^{13}$CNMR (125 MHz, CDCl$_3$) δ 165.6, 156.7, 156.6, 145.5, 130.0, 128.7, 122.5, 121.1, 113.9, 111.9, 98.7, 55.8, 51.2, 31.8; LRMS (APCI): m/z calcd for $C_{14}H_{16}NO_3S$ [M+H]$^+$ 278.09, found 277.83.

<2-6> Synthesis of Methyl 3-amino-5-(4-methoxyphenyl)thiophene-2-carboxylate (3bd)

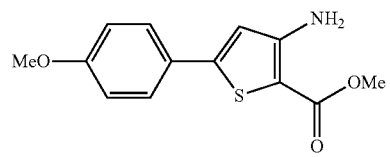 [SMILES: COC(=O)c1sc(-c2ccc(OC)cc2)cc1N]

Methyl 3-amino-5-(4-methoxyphenyl)thiophene-2-carboxylate (3bd)

Compound 1 (500 mg, 2.12 mmol, 1.0 equiv.) in the reaction scheme of Example 1, 4-methoxyphenyl boronic acid (386 mg, 2.50 mmol, 1.2 equiv.), Pd(PPh$_3$)$_4$ (122 mg, 0.110 mmol, 0.05 equiv.), 0.4M sodium carbonate (6.4 mL), and toluene (8.5 mL) were used in a similar manner to synthesis step I of Example 1 to afford compound 3bd as a yellow solid (480 mg, 1.82 mmol, 86%). NMR data for compound 3bd are given as follow:

$^1$H NMR (600 MHz, CDCl$_3$) δ 7.52 (dd, J=6.6 Hz and J=2.4 Hz, 2H), 6.91 (dd, J=6.6 Hz and J=2.4 Hz, 2H), 6.67 (s, 1H), 3.84 (s, 3H), 3.83 (s, 3H); $^{13}$CNMR (150 MHz, CDCl$_3$) δ 165.1, 160.5, 154.6, 149.4, 127.4, 126.2, 114.6, 114.5, 99.7, 55.5, 51.4; LRMS (APCI): m/z calcd for C$_{13}$H$_{14}$NO$_3$S [M+H]$^+$ 264.07, found 263.78.

<2-7> Synthesis of Methyl 3-(benzylamino)-5-(4-methoxyphenyl)thiophene-2-carboxylate (3be)

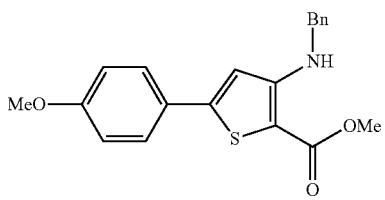 [SMILES: COC(=O)c1sc(-c2ccc(OC)cc2)cc1NCc1ccccc1]

Methyl 3-(benzylamino)-5-(4-methoxyphenyl)thiophene-2-carboxylate (3be)

Compound 2b (500 mg, 1.53 mmol, 1.0 equiv.), 4-methoxyphenyl boronic acid (280 mg, 1.84 mmol, 1.2 equiv.), 4-methoxyphenyl boronic acid (386 mg, 2.50 mmol, 1.2 equiv.), Pd(PPh$_3$)$_4$ (88.6 mg, 0.0800 mmol, 0.05 equiv.), 0.4M sodium carbonate (4 mL), and toluene (6.1 mL) were used in a similar manner to synthesis step I of Example 1 to afford compound 3be as a yellow solid (392 mg, 1.11 mmol, 73%). NMR data for compound 3be are given as follow:

$^1$H NMR (600 MHz, CDCl$_3$) δ 7.50 (dd, J=6.6 Hz and J=1.8 Hz, 2H), 7.37-7.33 (m, 4H), 7.29-7.26 (m, 1H), 7.22 (br s, 1H), 6.89 (dd, J=6.6 Hz and J=2.4 Hz, 2H), 6.70 (s, 1H), 4.53 (d, J=6.0 Hz, 2H), 3.84 (s, 3H), 3.82 (s, 3H); $^{13}$CNMR (150 MHz, CDCl$_3$) δ 165.5, 160.5, 156.7, 150.0, 139.0, 128.9, 127.49, 127.45, 127.1, 126.4, 114.4, 111.2, 97.5, 55.5, 51.2, 49.1; LRMS (APCI): m/z calcd for C$_{20}$H$_{20}$NO$_3$S [M+H]$^+$ 354.12, found 353.98.

<2-8> Synthesis of Methyl 3-(methylamino)-5-(4-phenoxyphenyl)thiophene-2-carboxylate (3ca)

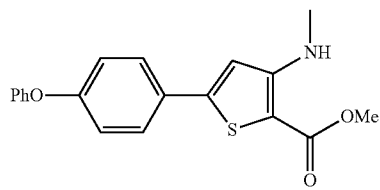 [SMILES: CNc1cc(-c2ccc(Oc3ccccc3)cc2)sc1C(=O)OC]

Methyl 3-(methylamino)-5-(4-phenoxyphenyl)thiophene-2-carboxylate (3ca)

Compound 2a (200 mg, 0.800 mmol, 1.0 equiv.), 4-methoxyphenyl boronic acid (280 mg, 1.84 mmol, 1.2 equiv.), (4-methoxyphenyl)boronic acid (205 mg, 0960 mmol, 1.2 equiv.), Pd(PPh$_3$)$_4$ (46.2 mg, 0.0400 mmol, 0.05 equiv.), 0.4M sodium carbonate (2 mL), and toluene (3.2 mL) were used in a similar manner to synthesis step I of Example 1 to afford compound 3ca as a pale yellow solid (220 mg, 0.648 mmol, 81%). NMR data for compound 3ca are given as follow:

$^1$H NMR (600 MHz, CDCl$_3$) δ 7.60-7.58 (m, 2H), 7.38-7.36 (m, 2H), 7.15 (tt, J=7.5 Hz and J=1.2 Hz, 1H), 7.07-7.05 (m, 2H), 7.03-7.00 (m, 2H), 6.79 (s, 1H), 3.83 (s, 3H), 3.03 (s, 3H); $^{13}$CNMR (150 MHz, CDCl$_3$) δ 165.4, 158.4, 157.6, 156.6, 149.4, 130.0, 128.7, 127.6, 124.0, 119.5, 118.9, 111.3, 97.1, 51.2, 31.8; LRMS (APCI): m/z calcd for C$_{19}$H$_{18}$NO$_3$S [M+H]$^+$ 340.10, found 339.91.

<2-9> Synthesis of Methyl 5-(benzo[d][1,3]dioxol-5-yl)-3-(methylamino)thiophene-2-carboxylate (3da)

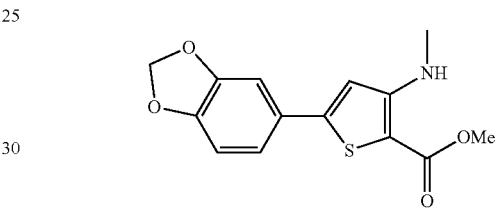

Methyl 5-(benzo[d][1,3]dioxol-5-yl)-3-(methylamino)thiophene-2-carboxylate (3da)

Compound 2a (400 mg, 1.60 mmol, 1.0 equiv.), benzo[d][1,3]dioxol-5-ylboronic acid (318 mg, 1.92 mmol, 1.2 equiv.), Pd(PPh$_3$)$_4$ (92.4 mg, 0.0800 mmol, 0.05 equiv.), 0.4M sodium carbonate (4.8 mL), and toluene (6.4 mL) were used in a similar manner to synthesis step I of Example 1 to afford compound 3da as a pale yellow solid (319 mg, 1.09 mmol, 68%). NMR data for compound 3da are given as follow:

$^1$H NMR (600 MHz, CDCl$_3$) δ 7.14 (dd, J=8.4 Hz and J=1.8 Hz, 1H), 7.09 (d, J=1.8 Hz, 1H), 6.82 (d, J=7.8 Hz, 1H), 6.73 (s, 1H), 6.00 (s, 2H), 3.82 (s, 3H), 3.02 (s, 3H); $^{13}$CNMR (150 MHz, CDCl$_3$) δ 165.4, 157.6, 149.9, 148.6, 148.3, 128.1, 120.3, 111.2, 108.8, 106.6, 101.6, 96.9, 51.2, 31.8; LRMS (APCI): m/z calcd for C$_{14}$H$_{14}$NO$_4$S [M+H]$^+$ 292.06, found 291.91.

<2-10> Methyl 5-(2,3-dihydrobenzo[b][1,4]dioxin-6-yl)-3-(methylamino)thiophene-2-carboxylate (3ea)

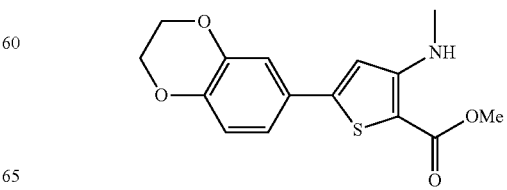

Methyl 5-(2,3-dihydrobenzo[b][1,4]dioxin-6-yl)-3-(methylamino)thiophene-2-carboxylate (3ea)

Compound 2a (250 mg, 1.00 mmol, 1.0 equiv.), (2,3-dihydrobenzo[b][1,4]dioxin-6-yl)boronic acid (216 mg, 1.20 mmol, 1.2 equiv.), Pd(PPh$_3$)$_4$ (57.0 mg, 0.0500 mmol, 0.05 equiv), 0.4M sodium carbonate (2 mL), and toluene (2.5 mL) were used in a similar manner to synthesis step I of Example 1 to afford compound 3ea as a sticky, pale yellow solid (274 mg, 0.897 mmol, 90%). $^1$H NMR data for compound 3ea are given as follow:

$^1$H NMR (600 MHz, CDCl$_3$) δ 7.11 (d, J=2.4 Hz, 1H), 7.08 (dd, J=8.4 Hz and J=2.4 Hz, 1H), 6.83 (d, J=8.4 Hz, 1H), 6.70 (s, 1H), 6.64 (br s, 1H), 4.22 (s, 4H), 3.79 (s, 3H), 2.97 (d, J=4.8 Hz, 3H); $^{13}$CNMR (150 MHz, CDCl$_3$) δ 165.2, 157.5, 149.5, 144.5, 143.6, 127.2, 119.3, 117.6, 114.8, 110.8, 96.6, 64.4, 64.3, 50.9, 31.5; LRMS (APCI): m/z calcd for C$_{15}$H$_{16}$NO$_4$S [M+H]$^+$ 306.08, found 305.79.

<2-11> Synthesis of Methyl 3-(methylamino)-5-(3,4,5-trimethoxyphenyl)thiophene-2-carboxylate (3fa)

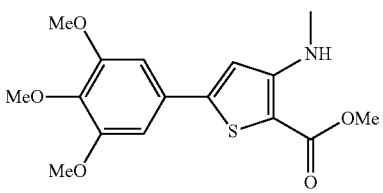 [SMILES: CNc1cc(-c2cc(OC)c(OC)c(OC)c2)sc1C(=O)OC]

Methyl 3-(methylamino)-5-(3,4,5-trimethoxyphenyl)thiophene-2-carboxylate (3fa)

Compound 2a (485 mg, 1.94 mmol, 1.0 equiv.), (3,4,5-trimethoxyphenyl)boronic acid (493 mg, 2.33 mmol, 1.2 equiv.), Pd(PPh$_3$)$_4$ (112 mg, 0.100 mmol, 0.05 equiv.), 0.4M sodium carbonate (5.8 mL), and toluene (7.8 mL) were used in a similar manner to synthesis step I of Example 1 to afford compound 3fa as a yellow solid (438 mg, 1.30 mmol, 67%). NMR data for compound 3fa are given as follow:

$^1$H NMR (600 MHz, CDCl$_3$) δ 6.82 (s, 2H), 6.77 (s, 1H), 3.91 (s, 6H), 3.91 (s, 3H), 3.83 (s, 3H), 3.05 (s, 3H); $^{13}$CNMR (150 MHz, CDCl$_3$) δ 165.3, 157.3, 153.7, 150.1, 139.2, 129.5, 111.7, 103.7, 93.0, 61.1, 56.4, 51.3, 31.9; LRMS (APCI): m/z calcd for C$_{16}$H$_{20}$NO$_5$S [M+H]$^+$ 338.11, found 338.07.

<2-12> Synthesis of Methyl 5-(4-(dimethylamino)phenyl)-3-(methylamino)thiophene-2-carboxylate (3ga)

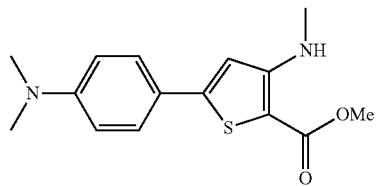 [SMILES: CNc1cc(-c2ccc(N(C)C)cc2)sc1C(=O)OC]

Methyl 5-(4-(dimethylamino)phenyl)-3-(methylamino)thiophene-2-carboxylate (3ga)

Compound 2a (300 mg, 1.20 mmol, 1.0 equiv.), (4-(dimethylamino)phenyl) boronic acid (237 mg, 1.43 mmol, 1.2 equiv.) Pd(PPh$_3$)$_4$ (69.3 mg, 0.0600 mmol, 0.05 equiv.), 0.4M sodium carbonate (2 mL), and DMF (4.8 mL) were used in a similar manner to synthesis step I of Example 1 to afford compound 3ga as a pale red solid (194 mg, 0.668 mmol, 56%). NMR data for compound 3ga are given as follow:

$^1$H NMR (600 MHz, CDCl$_3$) δ 7.52 (d, J=9.0 Hz, 2H), 6.71 (s, 1H), 6.70 (d, J=9.0 Hz, 2H), 3.81 (s, 3H), 3.02 (d, J=5.4 Hz, 3H), 3.01 (s, 6H); $^{13}$CNMR (150 MHz, CDCl$_3$) δ 165.5, 158.1, 151.3, 151.0, 127.2, 121.7, 112.2, 109.2, 95.5, 51.1, 40.4, 31.8; LRMS (APCI): m/z calcd for C$_{15}$H$_{19}$N$_2$O$_2$S [M+H]$^+$ 291.12, found 290.82.

<2-13> Synthesis of Methyl 5-(3-(dimethylamino)phenyl)-3-(methylamino)thiophene-2-carboxylate (3gb)

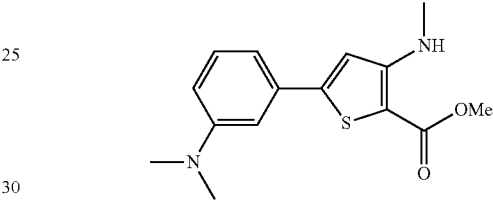

Methyl 5-(3-(dimethylamino)phenyl)-3-(methylamino)thiophene-2-carboxylate (3gb)

Compound 2a (300 mg, 1.20 mmol, 1.0 equiv.), (3-(dimethylamino)phenyl) boronic acid (237 mg, 1.43 mmol, 1.2 equiv.), Pd(PPh$_3$)$_4$ (69.3 mg, 0.0600 mmol, 0.05 equiv.), 0.4M sodium carbonate (2 mL), and toluene (4.8 mL) were used in a similar manner to synthesis step I of Example 1 to afford compound 3gb as a yellow solid (250 mg, 0.861 mmol, 72%). NMR data for compound 3ga are given as follow:

$^1$H NMR (600 MHz, CDCl$_3$) δ 7.26 (t, J=8.1 Hz, 1H), 7.00 (dd, J=7.2 Hz and J=1.2 Hz, 1H), 6.93 (t, J=2.4 Hz, 1H), 6.84 (s, 1H), 6.74 (dd, J=8.4 Hz and J=2.4 Hz, 1H), 6.67 (br s, 1H), 3.83 (s, 3H), 3.04 (d, J=5.4 Hz, 3H), 3.00 (s, 6H); $^{13}$CNMR (150 MHz, CDCl$_3$) δ 165.4, 157.6, 151.2, 150.9, 134.5, 129.7, 114.6, 113.3, 111.7, 110.0, 97.2, 51.2, 40.7, 31.8; LRMS (APCI): m/z calcd for C$_{15}$H$_{19}$N$_2$O$_2$S [M+H]$^+$ 291.12, found 290.96.

<2-14> Synthesis of Methyl 5-(2-(dimethylamino)phenyl)-3-(methylamino)thiophene-2-carboxylate (3gc)

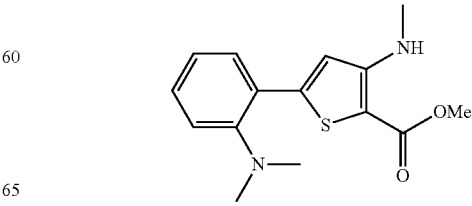

Methyl 5-(2-(dimethylamino)phenyl)-3-(methylamino)thiophene-2-carboxylate (3gc)

Compound 2a (200 mg, 0.800 mmol, 1.0 equiv.), (2-(dimethylamino)phenyl) boronic acid (158 mg, 0.960 mmol, 1.2 equiv.), Pd(PPh$_3$)$_4$ (46.0 mg, 0.0400 mmol, 0.05 equiv.), 0.4M sodium carbonate (1 mL), and DMF (3.2 mL) were used in a similar manner to synthesis step I of Example 1 to afford compound 3gc as a yellow liquid (250 mg, 0.861 mmol, 72%). NMR data for compound 3gc are given as follow:

$^1$H NMR (600 MHz, CDCl$_3$) δ 7.56 (dd, J=7.8 Hz and J=1.2 Hz, 1H), 7.28 (td, J=7.8 Hz and J=1.4 Hz, 1H), 7.14 (dd, J=7.8 Hz and J=1.2 Hz, 1H), 7.05 (td, J=7.2 Hz and J=1.2 Hz, 1H), 6.99 (s, 1H), 6.64-6.63 (m, 1H), 3.83 (s, 3H), 3.02 (d, J=5.4 Hz, 3H), 2.68 (s, 6H); $^{13}$CNMR (150 MHz, CDCl$_3$) δ 165.8, 156.7, 151.9, 147.9, 129.6, 129.4, 128.0, 123.0, 119.9, 113.5, 98.8, 51.0, 44.3, 31.7; LRMS (APCI): m/z calcd for C$_{15}$H$_{19}$N$_2$O$_2$S [M+H]$^+$ 291.12, found 290.82.

<2-15> Synthesis of Methyl 3-(benzylamino)-5-(4-(dimethylamino)phenyl)thiophene-2-carboxylate (3gd)

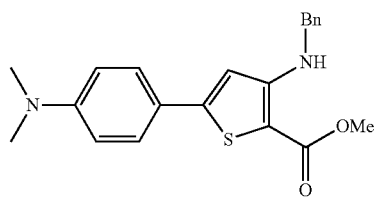 [SMILES: COC(=O)c1sc(-c2ccc(N(C)C)cc2)cc1NCc1ccccc1]

Methyl 3-(benzylamino)-5-(4-(dimethylamino)phenyl)thiophene-2-carboxylate (3gd)

Compound 2b (500 mg, 1.53 mmol, 1.0 equiv.), (4-(dimethylamino)phenyl)boronic acid (304 mg, 1.84 mmol, 1.2 equiv.), Pd(PPh$_3$)$_4$ (88.6 mg, 0.0800 mmol, 0.05 equiv.), 0.4M sodium carbonate (2 mL), and toluene (6.1 mL) were used in a similar manner to synthesis step I of Example 1 to afford compound 3gd as a red solid (371 mg, 1.01 mmol, 66%). NMR data for compound 3gd are given as follow:

$^1$H NMR (600 MHz, CDCl$_3$) δ 7.46-7.44 (m, 2H), 7.37-7.33 (m, 4H), 7.28-7.25 (m, 2H), 6.67-6.66 (m, 3H), 4.53 (d, J=6.0 Hz, 2H), 3.83 (s, 3H), 2.99 (s, 6H); $^{13}$CNMR (150 MHz, CDCl$_3$) δ 165.5, 157.0, 151.3, 151.0, 139.2, 128.8, 127.4, 127.2, 121.6, 112.2, 109.8, 96.3, 51.1, 49.1, 40.4; LRMS (APCI): m/z calcd for C$_{21}$H$_{23}$N$_2$O$_2$S [M+H]$^+$ 367.15, found 367.02.

<2-16> Synthesis of Methyl 5-(4-(diethylamino)phenyl)-3-(methylamino)thiophene-2-carboxylate (3ha)

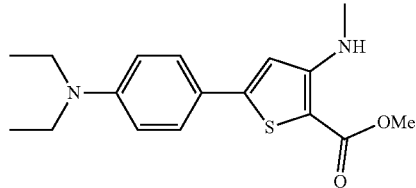 [SMILES: CCN(CC)c1ccc(-c2cc(NC)c(C(=O)OC)s2)cc1]

Methyl 5-(4-(diethylamino)phenyl)-3-(methylamino)thiophene-2-carboxylate (3ha)

Compound 2a (400 mg, 1.60 mmol, 1.0 equiv.), (4-(diethylamino)phenyl)boronic acid (528 mg, 1.92 mmol, 1.2 equiv.), Pd(PPh$_3$)$_4$ (92.3 mg, 0.0800 mmol, 0.05 equiv.), 0.4M sodium carbonate (2 mL), and toluene (6.4 mL) were used in a similar manner to synthesis step I of Example 1 to afford compound 3ha as a yellow solid (490 mg, 1.54 mmol, 96%). NMR data for compound 3ha are given as follow:

$^1$H NMR (500 MHz, CDCl$_3$) δ 7.49 (d, J=9.0 Hz, 2H), 6.70 (s, 1H), 6.65 (d, J=9.0 Hz, 2H), 3.82 (s, 3H), 3.37 (q, J=7.3 Hz, 4H), 3.03 (d, J=5.0 Hz, 3H), 1.19 (t, J=7.0 Hz, 6H); $^{13}$CNMR (125 MHz, CDCl$_3$) δ 165.4, 158.0, 151.4, 148.4, 127.3, 120.6, 111.4, 108.7, 95.1, 50.9, 44.5, 31.7, 12.7; LRMS (APCI): m/z calcd for C$_{17}$H$_{23}$N$_2$O$_2$S [M+H]$^+$ 319.15, found 319.05.

<2-17> Synthesis of Methyl 3-(methylamino)-5-(4-(4-methylpiperazin-1-yl)phenyl)thiophene-2-carboxylate (3ia)

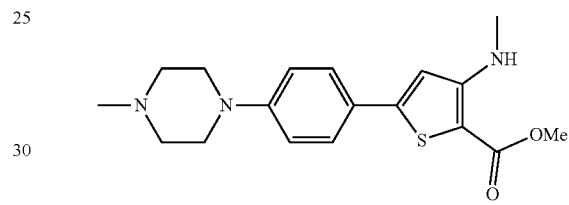

Methyl 3-(methylamino)-5-(4-(4-methylpiperazin-1-yl)phenyl)thiophene-2-carboxylate (3ia)

Compound 2a (100 mg, 0.400 mmol, 1.0 equiv.), 4-(4-methyl)-piperazinylboronic acid (145 mg, 0.480 mmol, 1.2 equiv.), Pd(PPh$_3$)$_4$ (23.0 mg, 0.0200 mmol, 0.05 equiv.), 0.4M sodium carbonate (0.5 mL), and DMF (1.6 mL) were used in a similar manner to synthesis step I of Example 1 to afford compound 3ia as a brown solid (113 mg, 0.327 mmol, 82%). NMR data for compound 3ia are given as follow:

$^1$H NMR (600 MHz, CDCl$_3$) δ 7.53 (d, J=8.4 Hz, 2H), 6.91 (d, J=8.4 Hz, 2H), 6.74 (s, 1H), 6.67 (br s, 1H), 3.81 (s, 3H), 3.28 (t, J=5.1 Hz, 4H), 3.02 (d, J=5.4 Hz, 3H), 2.57 (t, J=5.1 Hz, 4H), 2.36 (s, 3H); $^{13}$CNMR (150 MHz, CDCl$_3$) δ 165.5, 157.9, 151.7, 150.5, 127.1, 124.6, 115.5, 110.0, 96.2, 55.0, 51.1, 48.4, 46.3, 31.8; LRMS (APCI): m/z calcd for C$_{18}$H$_{24}$N$_3$O$_2$S [M+H]$^+$ 346.16, found 345.91.

<2-18> Synthesis of Methyl 3-(methylamino)-5-(2,3,6,7-tetrahydro-1H, 5H-pyrido[3,2,1-ij]quinolin-9-yl)thiophene-2-carboxylate (3ja)

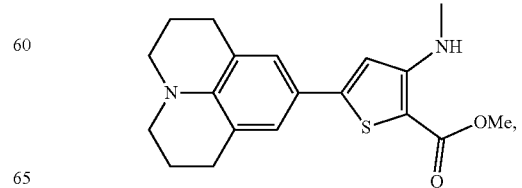

Methyl 3-(methylamino)-5-(2,3,6,7-tetrahydro-1H,5H-pyrido[3,2,1-ij]quinolin-9-yl)thiophene-2-carboxylate (3ja)

To a solution of compound 2a (100 mg, 0.400 mmol, 1.0 equiv) in dioxane/H₂O (3:1, 1.6 mL) were added 2,3,6,7-tetrahydro-1H,5H-pyrido[3,2,1-ij]-quinolin-9-yl)boronic acid (96.0 mg, 0.440 mmol, 1.2 equiv), Pd(OAc)₂ (9.00 mg, 0.0400 mmol, 0.1 equiv), 1,1'-bis(diphenylphospino)ferrocene (dppf, 22.2 mg, 0.0400 mmol, 0.1 equiv), and Cs₂CO₃ (260 mg, 0.800 mmol, 2.0 equiv). Then, the mixture was heated under reflux for 18 hours. To quench the reaction mixture, water (2 mL) was added. The crude product was extracted with DCM (3 mL) three times. The organic layer was dried over Na₂SO₄, filtered, and evaporated in a vacuum. The mixture was purified by flash column chromatography (hexane/EtOAc=3/1, v/v) on silica to afford compound 3ja as a red-orange solid (45.0 mg, 0.131 mmol, 33%).

$^1$H NMR (600 MHz, CDCl₃) δ 7.08 (s, 2H), 6.65 (s, 1H), 3.80 (s, 3H), 3.19 (t, J=5.7 Hz, 4H), 3.01 (d, J=4.8 Hz, 3H), 2.76 (t, J=6.6 Hz, 4H), 2.00-1.95 (m, 4H); $^{13}$CNMR (150 MHz, CDCl₃) δ 165.4, 158.1, 151.8, 143.8, 124.8, 121.3, 120.6, 108.6, 94.6, 50.9, 50.0, 31.7, 27.8, 21.9; LRMS (APCI): m/z calcd for C₁₉H₂₃N₂O₂S [M+H]⁺ 343.15, found 342.89.

<2-19> Synthesis of Methyl 5-(4-(diphenylamino)phenyl)-3-(methylamino)thiophene-2-carboxylate (3ka)

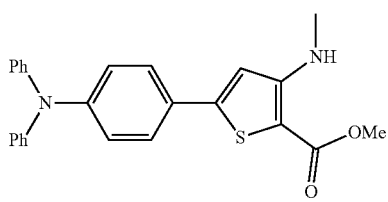 [SMILES: CNc1cc(-c2ccc(N(c3ccccc3)c3ccccc3)cc2)sc1C(=O)OC]

Methyl 5-(4-(diphenylamino)phenyl)-3-(methylamino)thiophene-2-carboxylate (3ka)

Compound 2a (500 mg, 2.00 mmol, 1.0 equiv.), (4-(diphenylamino)phenyl) boronic acid (693 mg, 2.40 mmol, 1.2 equiv.), Pd(PPh₃)₄ (116 mg, 0.100 mmol, 0.05 equiv.), 0.4M sodium carbonate (3 mL), and toluene (8 mL) were used in a similar manner to synthesis step I of Example 1 to afford compound 3ka as a yellow solid (728 mg, 1.76 mmol, 88%). NMR data for compound 3ka are given as follow:

$^1$H NMR (600 MHz, CDCl₃) δ 7.94-7.47 (m, 2H), 7.30-7.27 (m, 4H), 7.14-7.12 (m, 4H), 7.08-7.04 (m, 4H), 6.77 (s, 1H), 3.82 (s, 3H), 3.02 (s, 3H); $^{13}$CNMR (150 MHz, CDCl₃) δ 165.4, 157.7, 150.0, 148.8, 147.3, 129.5, 127.2, 126.9, 125.1, 123.7, 122.8, 110.6, 96.7, 51.2, 31.8; LRMS (APCI): m/z calcd for C₂₅H₂₃N₂O₂S [M+H]⁺ 415.15, found 415.04.

<2-20> Synthesis of Methyl 3-(methylamino)-5-(4-(trifluoromethoxy)phenyl)thiophene-2-carboxylate (31a)

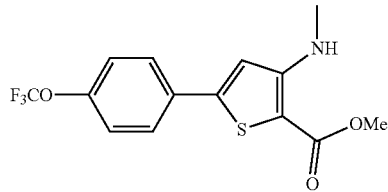 [SMILES: CNc1cc(-c2ccc(OC(F)(F)F)cc2)sc1C(=O)OC]

Methyl 3-(methylamino)-5-(4-(trifluoromethoxy)phenyl)thiophene-2-carboxylate (31a)

Compound 2a (400 mg, 1.60 mmol, 1.0 equiv.), (4-(trifluoromethoxy)phenyl)boronic acid (395 mg, 1.92 mmol, 1.2 equiv.), Pd(PPh₃)₄ (92.0 mg, 0.0800 mmol, 0.05 equiv.), 0.4M sodium carbonate (4.8 mL), and toluene (6.4 mL) were used in a similar manner to synthesis step I of Example 1 to afford compound 31a as a yellow solid (365 mg, 1.10 mmol, 69%). NMR data for compound 31a are given as follow:

$^1$H NMR (600 MHz, CDCl₃) δ 7.64 (d, J=8.4 Hz, 2H), 7.24 (d, J=8.4 Hz, 2H), 6.83 (s, 1H), 3.83 (s, 3H), 3.03 (s, 3H); $^{13}$CNMR (150 MHz, CDCl₃) δ 165.3, 157.4, 149.67, 149.66, 149.65, 149.63, 148.1, 132.6, 127.6, 123.1, 121.5, 121.4, 121.3, 119.7, 112.3, 98.2, 51.3, 31.8; $^{19}$FNMR (600 MHz, CDCl₃) δ −57.8; LRMS (APCI): m/z calcd for C₁₄H₁₃F₃NO₃S [M+H]⁺ 332.06, found 331.84.

<2-21> Synthesis of Methyl 3-(methylamino)-5-(4-(trifluoromethyl)phenyl)thiophene-2-carboxylate (3ma)

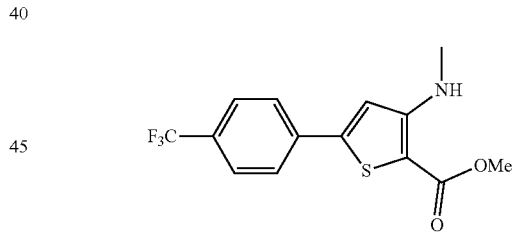

Methyl 3-(methylamino)-5-(4-(trifluoromethyl)phenyl)thiophene-2-carboxylate (3ma)

Compound 2a (400 mg, 1.60 mmol, 1.0 equiv.), (4-(trifluoromethyl)phenyl)boronic acid (365 mg, 1.92 mmol, 1.2 equiv.), Pd(PPh₃)₄ (92.0 mg, 0.0800 mmol, 0.05 equiv.), 0.4M sodium carbonate (4.8 mL), and toluene (6.4 mL) were used in a similar manner to synthesis step I of Example 1 to afford compound 3ma as a yellow solid (345 mg, 1.09 mmol, 680). NMR data for compound 3ma are given as follow:

$^1$H NMR (600 MHz, CDCl₃) δ 7.72 (d, J=8.4 Hz, 2H), 7.64 (d, J=8.4 Hz, 2H), 6.91 (s, 1H), 3.84 (s, 3H), 3.04 (s, 3H); $^{13}$CNMR (150 MHz, CDCl₃) δ 165.3, 157.3, 147.6, 137.2, 131.1, 130.8, 130.6, 130.4 (F-coupling), 126.8, 126.3, 126.2, 126.12, 126.09 (F-coupling), 126.07, 126.05, 125.0, 123.2, 121.4, 112.9, 98.8, 51.4, 31.8; $^{19}$FNMR (600 MHz, CDCl₃) δ −62.7; LRMS (APCI): m/z calcd for C$_{14}$H$_{13}$F$_3$NO$_2$S [M+H]⁺ 316.06, found 315.87.

<2-22> Synthesis of 5-(4-Methoxyphenyl)-N-methylthiophen-3-amine (5ba)

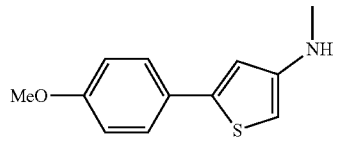

5-(4-Methoxyphenyl)-N-methylthiophen-3-amine (5ba)

Compound 3ba (185 mg, 0.667 mmol, 1.0 equiv.) was used in a similar manner to synthesis step II of Example 1 to afford compound 5ba as a pale yellow solid (130 mg, 0.593 mmol, 89%). NMR data for compound 5ba are given as follow:

¹H NMR (600 MHz, CDCl₃) δ 7.48 (dd, J=6.6 Hz and J=1.8 Hz, 2H), 6.91 (dd, J=6.6 Hz and J=2.4 Hz, 2H), 6.74 (d, J=1.8 Hz, 1H), 5.87 (d, J=1.8 Hz, 1H), 3.83 (s, 3H), 2.84 (s, 3H); ¹³CNMR (150 MHz, CDCl₃) δ 159.3, 150.3, 143.6, 127.6, 126.9, 115.1, 114.3, 94.0, 55.5, 32.8; LRMS (APCI): m/z calcd for C$_{12}$H$_{14}$NOS [M+H]⁺ 220.08, found 219.93.

<2-23> Synthesis of 5-(3-Methoxyphenyl)-N-methylthiophen-3-amine (5bb)

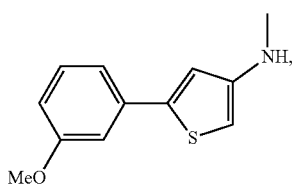

5-(3-Methoxyphenyl)-N-methylthiophen-3-amine (5bb)

Compound 3bb (182 mg, 0.656 mmol, 1.0 equiv.) was used in a similar manner to synthesis step II of Example 1 to afford compound 5bb as a brown oil (122 mg, 0.556 mmol, 85%). NMR data for compound 5bb are given as follow:

¹H NMR (500 MHz, CDCl₃) δ 7.36 (t, J=7.8 Hz, 1H), 7.27 (d, J=7.5 Hz, 1H), 7.23 (s, 1H), 6.93 (dd, J=2.5 Hz and J=8.0 Hz, 1H), 6.89 (d, J=1.8 Hz, 1H), 5.99 (d, J=2.0 Hz, 1H), 3.90 (s, 3H), 3.71 (br s, 1H), 2.87 (s, 3H); ¹³CNMR (125 MHz, CDCl₃) δ 159.8, 150.2, 142.9, 135.8, 129.7, 117.9, 116.1, 112.7, 111.0, 94.5, 55.1, 32.4; LRMS (APCI): m/z calcd for C$_{12}$H$_{14}$NOS [M+H]⁺ 220.08, found 219.81.

<2-24> Synthesis of 5-(2-Methoxyphenyl)-N-methylthiophen-3-amine (5bc)

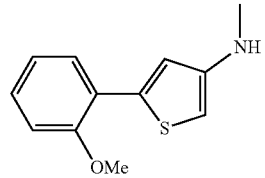

5-(2-Methoxyphenyl)-N-methylthiophen-3-amine (5bc)

Compound 3bc (204 mg, 0.736 mmol, 1.0 equiv.) was used in a similar manner to synthesis step II of Example 1 to afford compound 5bc as a pale yellow solid (139 mg, 0.634 mmol, 86%). NMR data for compound 5bc are given as follow:

¹H NMR (500 MHz, CDCl₃) δ 7.62 (dd, J=7.5 Hz and J=1.5 Hz, 1H), 7.26 (td, J=7.9 Hz and J=1.8 Hz, 1H), 7.09 (d, J=1.5 Hz, 1H), 7.01-6.96 (m, 2H), 6.00 (d, J=1.5 Hz, 1H), 3.90 (s, 3H), 3.63 (br s, 1H), 2.84 (s, 3H); ¹³CNMR (150 MHz, CDCl₃) δ 155.8, 149.6, 138.7, 128.28, 128.25, 123.4, 120.8, 118.5, 111.6, 95.6, 55.5, 32.7; LRMS (APCI): m/z calcd for C$_{12}$H$_{14}$NOS [M+H]⁺ 220.08, found 219.90.

<2-25> Synthesis of 5-(4-Methoxyphenyl)thiophen-3-amine (5bd)

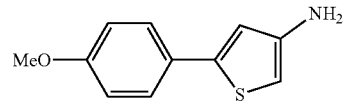 [SMILES: COc1ccc(-c2cc(N)cs2)cc1]

5-(4-Methoxyphenyl)thiophen-3-amine (5bd)

Compound 3bd (318 mg, 1.21 mmol, 1.0 equiv.) was used in a similar manner to synthesis step II of Example 1 to afford compound 5bd as a pale yellow solid (104 mg, 0.507 mmol, 42%). NMR data for compound 5bd are given as follow:

¹H NMR (600 MHz, CDCl₃) δ 7.48 (dd, J=6.6 Hz and J=1.2 Hz, 2H), 6.91 (dd, J=7.8 Hz and J=1.2 Hz, 2H), 6.77 (d, J=1.8 Hz, 1H), 6.07 (d, J=1.8 Hz, 1H), 3.83 (s, 3H); ¹³CNMR (150 MHz, CDCl₃) δ 159.3, 145.5, 143.8, 127.5, 126.9, 116.4, 114.3, 99.1, 55.5; LRMS (APCI): m/z calcd for C$_{11}$H$_{12}$NOS [M+H]⁺ 206.06, found 205.68.

<2-26> Synthesis of N-Benzyl-5-(4-methoxyphenyl)thiophen-3-amine (5be)

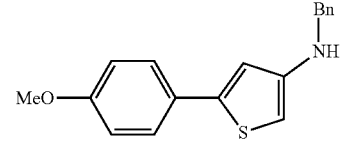 [SMILES: COc1ccc(-c2cc(NCc3ccccc3)cs2)cc1]

N-Benzyl-5-(4-methoxyphenyl)thiophen-3-amine (5be)

Compound 3be (336 mg, 0.951 mmol, 1.0 equiv.) was used in a similar manner to synthesis step II of Example 1 to afford compound 5be as a yellow solid (278 mg, 0.941 mmol, 99%). NMR data for compound 5be are given as follow:

$^1$H NMR (600 MHz, CDCl$_3$) δ 7.48 (d, J=9.0 Hz, 2H), 7.42-7.41 (m, 2H), 7.38-7.35 (m, 2H), 7.30 (tt, J=7.2 Hz and J=1.7 Hz, 1H), 6.91 (d, J=9.0 Hz, 2H), 6.78 (d, J=1.2 Hz, 1H), 5.89 (d, J=1.2 Hz, 1H), 4.29 (s, 2H), 3.83 (s, 3H); $^{13}$CNMR (150 MHz, CDCl$_3$) δ 159.3, 148.8, 143.5, 139.4, 128.7, 127.8, 127.5, 127.4, 126.9, 115.2, 114.3, 94.9, 55.5, 50.5; LRMS (APCI): m/z calcd for C$_{18}$H$_{18}$NOS [M+H]$^+$ 296.11, found 295.86.

<2-27> Synthesis of N-Methyl-5-(4-phenoxyphenyl)thiophen-3-amine (5ca)

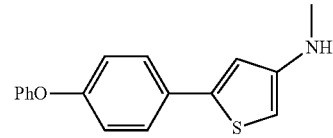 [SMILES: CNc1csc(-c2ccc(Oc3ccccc3)cc2)c1]

N-Methyl-5-(4-phenoxyphenyl)thiophen-3-amine (5ca)

Compound 3ca (56.0 mg, 0.165 mmol, 1.0 equiv.) was used in a similar manner to synthesis step II of Example 1 to afford compound 5ca as a pale yellow liquid (33.2 mg, 0.118 mmol, 72%). NMR data for compound 5ca are given as follow:

$^1$H NMR (600 MHz, CDCl$_3$) δ 7.53 (dd, J=6.6 Hz and J=1.8 Hz, 2H), 7.38-7.36 (m, 2H), 7.14 (tt, J=7.2 Hz and J=1.1 Hz, 1H), 7.07-7.05 (m, 2H), 7.01 (dd, J=6.6 Hz and J=1.8 Hz, 2H), 6.79 (d, J=1.8 Hz, 1H), 5.91 (d, J=1.2 Hz. 1H), 2.85 (s, 3H); $^{13}$CNMR (150 MHz, CDCl$_3$) δ 157.1, 156.9, 150.3, 143.0, 129.95, 129.90, 127.0, 123.5, 119.14, 119.06, 115.6, 94.5, 32.7; LRMS (APCI): m/z calcd for C$_{17}$H$_{16}$NOS [M+H]$^+$ 282.10, found 281.88.

<2-28> Synthesis of 5-(Benzo[d][1,3]dioxol-5-yl)-N-methylthiophen-3-amine (5da)

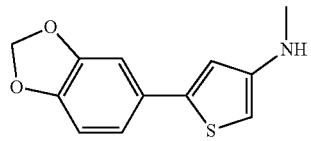 [SMILES: CNc1csc(-c2ccc3c(c2)OCO3)c1]

5-(Benzo[d][1,3]dioxol-5-yl)-N-methylthiophen-3-amine (5da)

Compound 3da (28.0 mg, 0.0961 mmol, 1.0 equiv.) was used in a similar manner to synthesis step II of Example 1 to afford compound 5da as a pale green solid (16.3 mg, 0.0699 mmol, 73%). NMR data for compound 5da are given as follow:

$^1$H NMR (600 MHz, CDCl$_3$) δ 7.05-7.03 (m, 2H), 6.80 (d, J=2.4 Hz, 1H), 6.72 (s, 1H), 5.97 (s, 2H), 5.86 (s, 1H), 3.63 (br s, 1H), 2.83 (s, 3H); $^{13}$CNMR (125 MHz, CDCl$_3$) δ 150.2, 148.1, 147.3, 143.5, 129.1, 119.4, 115.5, 108.7, 106.4, 101.3, 94.2, 32.7; LRMS (APCI): m/z calcd for C$_{12}$H$_{12}$NO$_2$S [M+H]$^+$ 234.06, found 233.76.

<2-29> Synthesis of 5-(2,3-Dihydrobenzo[b][1,4]dioxin-6-yl)-N-methylthiophen-3-amine (5ea)

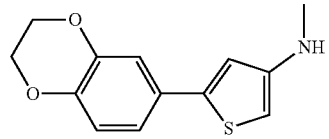 [SMILES: CNc1csc(-c2ccc3c(c2)OCCO3)c1]

5-(2,3-Dihydrobenzo[b][1,4]dioxin-6-yl)-N-methylthiophen-3-amine (5ea)

Compound 3ea (256 mg, 0.838 mmol, 1.0 equiv.) was used in a similar manner to synthesis step II of Example 1 to afford compound 5ea as a brown oil (160 mg, 0.647 mmol, 77%). NMR data for compound 5ea are given as follow:

$^1$H NMR (500 MHz, CDCl$_3$) δ 7.09-7.04 (m, 2H), 6.85 (d, J=8.5 Hz, 1H), 6.72 (d, J=2.0 Hz, 1H), 5.86 (d, J=1.5 Hz, 1H), 4.27 (s, 4H), 3.61 (br s, 1H), 2.83 (s, 3H); $^{13}$CNMR (125 MHz, CDCl$_3$) δ 150.2, 143.7, 143.3, 143.2, 128.5, 119.0, 117.6, 115.3, 114.5, 94.1, 64.53, 64.50, 32.7; LRMS (APCI): m/z calcd for C$_{13}$H$_{14}$NO$_2$S [M+H]$^+$ 248.07, found 247.95.

<2-30> Synthesis of N-Methyl-5-(3,4,5-trimethoxyphenyl)thiophen-3-amine (5fa)

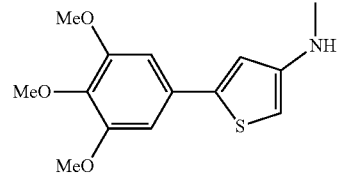 [SMILES: CNc1csc(-c2cc(OC)c(OC)c(OC)c2)c1]

N-Methyl-5-(3,4,5-trimethoxyphenyl)thiophen-3-amine (5fa)

Compound 3fa (400 mg, 1.19 mmol, 1.0 equiv.) was used in a similar manner to synthesis step II of Example 1 to afford compound 5fa as a brown oil (298 mg, 1.07 mmol, 90%). NMR data for compound 5fa are given as follow:

$^1$H NMR (600 MHz, CDCl$_3$) δ 6.77 (d, J=1.8 Hz, 1H), 6.75 (s, 2H), 5.89 (d, J=1.8 Hz, 1H), 3.89 (s, 6H), 3.86 (s, 3H), 2.83 (s, 3H); $^{13}$CNMR (150 MHz, CDCl$_3$) δ 153.4, 150.2, 143.5, 137.8, 130.5, 115.9, 103.1, 94.7, 61.0, 56.2, 32.7; LRMS (APCI): m/z calcd for C$_{14}$H$_{18}$NO$_3$S [M+H]$^+$ 280.10, found 279.81.

<2-31> Synthesis of 5-(4-(Dimethylamino)phenyl)-N-methylthiophen-3-amine (5ga)

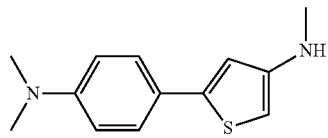

5-(4-(Dimethylamino)phenyl)-N-methylthiophen-3-amine (5ga)

Compound 3ga (1.20 g, 4.13 mmol, 1.0 equiv.) was used in a similar manner to synthesis step II of Example 1 to afford compound 5ga as a reddish brown solid (600 mg, 2.58 mmol, 62%). NMR data for compound 5ga are given as follow:

$^1$H NMR (600 MHz, CDCl$_3$) δ 7.44 (d, J=9.0 Hz, 2H), 6.71-6.70 (m, 3H), 5.81 (s, 1H), 2.98 (s, 6H), 2.84 (s, 3H); $^{13}$CNMR (150 MHz, CDCl$_3$) δ 150.2, 150.1, 144.5, 126.6, 123.3, 114.0, 112.6, 93.0, 40.6, 32.8; LRMS (APCI): m/z calcd for C$_{13}$H$_{17}$N$_2$S [M+H]$^+$ 233.11, found 232.80.

<2-32> Synthesis of 5-(3-(Dimethylamino)phenyl)-N-methylthiophen-3-amine (5gb)

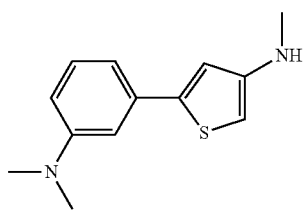

5-(3-(Dimethylamino)phenyl)-N-methylthiophen-3-amine (5gb)

Compound 3gb (159 mg, 0.547 mmol, 1.0 equiv.) was used in a similar manner to synthesis step II of Example 1 to afford compound 5gb as a brown liquid (109 mg, 0.469 mmol, 86%). NMR data for compound 5gb are given as follow:

$^1$H NMR (500 MHz, CDCl$_3$) δ 7.26 (t, J=8.0 Hz, 1H), 6.96 (d, J=7.5 Hz, 1H), 6.94-6.93 (m, 1H), 6.86 (d, J=1.5 Hz, 1H), 6.70 (dd, J=8.0 Hz and J=2.5 Hz, 1H), 5.93 (d, J=2.0 Hz, 1H), 3.38 (br s, 1H), 3.01 (s, 6H), 2.85 (s, 3H); $^{13}$CNMR (125 MHz, CDCl$_3$) δ 150.9, 150.1, 144.6, 135.4, 129.5, 115.9, 114.4, 112.0, 109.9, 94.6, 40.7, 32.7; LRMS (APCI): m/z calcd for C$_{13}$H$_{17}$N$_2$S [M+H]$^+$ 233.11, found 233.00.

<2-33> Synthesis of 5-(2-(Dimethylamino)phenyl)-N-methylthiophen-3-amine (5gc)

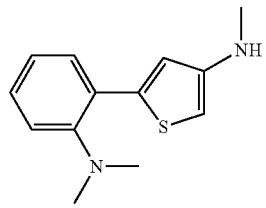 [SMILES: CNc1csc(-c2ccccc2N(C)C)c1]

5-(2-(Dimethylamino)phenyl)-N-methylthiophen-3-amine (5gc)

Compound 3gc (170 mg, 0.585 mmol, 1.0 equiv.) was used in a similar manner to synthesis step II of Example 1 to afford compound 5gc as a yellow liquid (110 mg, 0.473 mmol, 81%). NMR data for compound 5gc are given as follow:

$^1$H NMR (600 MHz, CDCl$_3$) δ 7.48 (d, J=7.8 Hz, 1H), 7.23 (t, J=7.2 Hz, 1H), 7.11 (d, J=8.4 Hz, 1H), 7.03 (t, J=7.5 Hz, 1H), 7.00 (s, 1H), 5.99 (s, 1H), 3.56 (br s, 1H), 2.86 (s, 3H), 2.67 (s, 6H); $^{13}$CNMR (150 MHz, CDCl$_3$) δ 151.3, 149.1, 141.4, 129.5, 128.9, 128.1, 122.8, 119.5, 117.9, 96.4, 44.2, 32.8; LRMS (APCI): m/z calcd for C$_{13}$H$_{17}$N$_2$S [M+H]$^+$ 233.11, found 232.80.

<2-34> Synthesis of N-Benzyl-5-(4-(dimethylamino)phenyl)thiophen-3-amine (5gd)

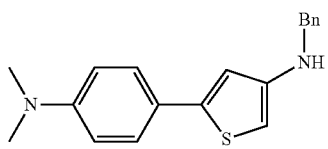 [SMILES: CN(C)c1ccc(-c2cc(NCc3ccccc3)cs2)cc1]

N-Benzyl-5-(4-(dimethylamino)phenyl)thiophen-3-amine (5gd)

Compound 3gd (350 mg, 0.955 mmol, 1.0 equiv.) was used in a similar manner to synthesis step II of Example 1 to afford compound 5gd as a reddidh brown solid (230 mg, 0.746 mmol, 78%). NMR data for compound 5gd are given as follow:

$^1$H NMR (600 MHz, CDCl$_3$) δ 7.45-7.41 (m, 4H), 7.37 (t, J=7.5 Hz, 2H), 7.30 (t, J=7.2 Hz, 1H), 6.74-6.740 (m, 1H), 6.71 (d, J=8.4 Hz, 2H), 5.84 (d, J=1.8 Hz, 1H), 4.29 (s, 2H), 3.95 (br s, 1H), 2.98 (s, 6H); $^{13}$CNMR (150 MHz, CDCl$_3$) δ 150.1, 148.7, 144.4, 139.5, 128.7, 127.8, 127.4, 126.6, 123.2, 114.1, 112.6, 93.9, 50.5, 40.6; LRMS (APCI): m/z calcd for C$_{19}$H$_{21}$N$_2$S [M+H]$^+$ 309.14, found 308.92.

<2-35> Synthesis of 5-(4-(Diethylamino)phenyl)-N-methylthiophen-3-amine (5ha)

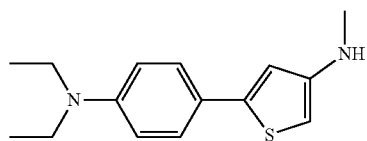 [SMILES: CCN(CC)c1ccc(-c2cc(NC)cs2)cc1]

5-(4-(Diethylamino)phenyl)-N-methylthiophen-3-amine (5ha)

Compound 3ha (80.8 mg, 0.254 mmol, 1.0 equiv.) was used in a similar manner to synthesis step II of Example 1 to afford compound 5ha as a reddish brown solid (41.5 mg, 0.159 mmol, 63%). NMR data for compound 5ha are given as follow:

$^1$H NMR (500 MHz, CDCl$_3$) δ 7.44 (dd, J=6.5 Hz and J=2.3 Hz, 2H), 6.70-6.67 (m, 3H), 5.81 (d, J=1.5 Hz, 1H), 3.62 (br s, 1H), 3.39 (q, J=7.0 Hz, 4H), 2.84 (s, 3H), 1.20 (t, J=7.3 Hz, 6H); $^{13}$CNMR (125 MHz, CDCl$_3$) δ 150.2, 147.3, 144.6, 126.8, 122.1, 113.7, 111.7, 92.6, 44.5, 32.7, 12.8; LRMS (APCI): m/z calcd for C$_{15}$H$_{21}$N$_2$S [M+H]$^+$ 261.14, found 260.97.

<2-36> Synthesis of N-Methyl-5-(4-(4-methylpiperazin-1-yl)phenyl)thiophen-3-amine (5ia)

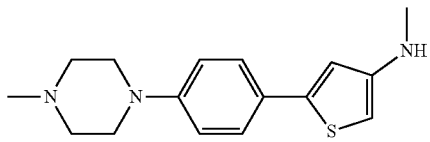

N-Methyl-5-(4-(4-methylpiperazin-1-yl)phenyl)thiophen-3-amine (5ia)

Compound 3ia (180 mg, 0.521 mmol, 1.0 equiv.) was used in a similar manner to synthesis step II of Example 1 to afford compound 5ia as a brown solid (123 mg, 0.428 mmol, 82%). NMR data for compound 5ia are given as follow:

$^1$H NMR (600 MHz, CDCl$_3$) δ 7.45 (d, J=9.0 Hz, 2H), 6.89 (d, J=9.0 Hz, 2H), 6.73 (s, 1H), 5.84 (s, 1H), 3.60 (br s, 1H), 3.24 (t, J=4.8 Hz, 4H), 2.83 (s, 3H), 2.57 (t, J=5.1 Hz, 4H), 2.35 (s, 3H); $^{13}$CNMR (150 MHz, CDCl$_3$) δ 150.7, 150.3, 143.9, 126.5, 126.1, 115.9, 114.6, 93.6, 55.2, 48.9, 46.3, 32.7; LRMS (APCI): m/z calcd for C$_{16}$H$_{22}$N$_3$S [M+H]$^+$ 288.15, found 287.86.

<2-37> Synthesis of N-Methyl-5-(2,3,6,7-tetrahydro-1H, 5H-pyrido[3,2,1-ij]quinolin-9-yl)thiophen-3-amine (5ja)

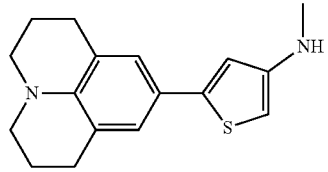 [SMILES: CNc1csc(-c2cc3c4c(c2)CCCN4CCC3)c1]

N-Methyl-5-(2,3,6,7-tetrahydro-1H,5H-pyrido[3,2,1-ij]quinolin-9-yl)thiophen-3-amine (5ja)

Compound 3ja (100 mg, 0.292 mmol, 1.0 equiv.) was used in a similar manner to synthesis step II of Example 1 to afford compound 5ja as a blackish brown liquid (74.3 mg, 0.261 mmol, 89%). NMR data for compound 5ja are given as follow:

$^1$H NMR (600 MHz, CDCl$_3$) δ 7.00 (s, 2H), 6.65 (s, 1H), 5.78 (s, 1H), 3.63 (br s, 1H), 3.16 (t, J=6.0 Hz, 4H), 2.83 (s, 3H), 2.77 (t, J=6.6 Hz, 4H), 2.00-1.96 (m, 4H); $^{13}$CNMR (150 MHz, CDCl$_3$) δ 150.1, 145.0, 142.7, 124.5, 122.3, 121.6, 113.6, 92.8, 50.1, 32.8, 27.8, 22.1; LRMS (APCI): m/z calcd for C$_{17}$H$_{19}$N$_2$S [M–H]$^-$ 283.13, found 283.19.

<2-38> Synthesis of 5-(4-(Diphenylamino)phenyl)-N-methylthiophen-3-amine (5ka)

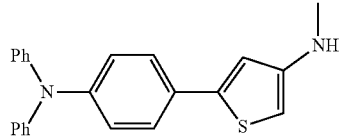 [SMILES: CNc1csc(-c2ccc(N(c3ccccc3)c3ccccc3)cc2)c1]

5-(4-(Diphenylamino)phenyl)-N-methylthiophen-3-amine (5ka)

Compound 3ka (406 mg, 0.979 mmol, 1.0 equiv.) was used in a similar manner to synthesis step II of Example 1 to afford compound 5ka as a redish brown solid (150 mg, 0.421 mmol, 43%). NMR data for compound 5ka are given as follows:

$^1$H NMR (600 MHz, CDCl$_3$) δ7.41 (d, J=8.4 Hz, 2H), 7.29-7.25 (m, 4H), 7.11 (d, J=7.8 Hz, 4H), 7.05-7.02 (m, 4H), 6.77 (s, 1H), 5.88 (s, 1H), 2.84 (s, 3H); $^{13}$CNMR (150 MHz, CDCl$_3$) δ150.3, 147.7, 147.3, 143.5, 129.4, 128.9, 126.4, 124.6, 123.8, 123.1, 115.2, 94.3, 32.8; LRMS (APCI): m/z calcd for C$_{23}$H$_{21}$N$_2$S [M+I]$^+$357.14, found 357.06.

<2-39> Synthesis of N-Methyl-5-(4-(trifluoromethoxy)phenyl)thiophen-3-amine (5la)

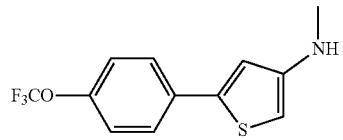

N-Methyl-5-(4-(trifluoromethoxy)phenyl)thiophen-3-amine (51a)

Compound 31a (339 mg, 1.02 mmol, 1.0 equiv.) was used in a similar manner to synthesis step II of Example 1 to afford compound 51a as a green solid (224 mg, 0.820 mmol, 80%). NMR data for compound 51a are given as follows:

$^1$H NMR (600 MHz, CDCl$_3$) δ 7.56 (dd, J=6.6 Hz and J=1.8 Hz, 2H), 7.21 (d, J=9.0 Hz and J=0.6 Hz, 2H), 6.82 (d, J=1.8 Hz, 1H), 5.95 (d, J=1.2 Hz, 1H), 2.85 (s, 3H); $^{13}$CNMR (150 MHz, CDCl$_3$) δ 150.4, 148.6, 141.9, 133.5, 126.9, 123.2, 121.4, 119.7, 118.0, 116.5, 95.5, 32.7; $^{19}$F NMR (600 MHz, CDCl$_3$) δ −57.9; LRMS (APCI): m/z calcd for C$_{12}$H$_{11}$F$_3$NOS [M+H]$^+$ 274.05, found 273.92.

<2-40> Synthesis of N-Methyl-5-(4-(trifluoromethyl)phenyl)thiophen-3-amine (5ma)

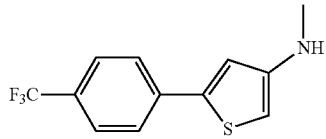

N-Methyl-5-(4-(trifluoromethyl)phenyl)thiophen-3-amine (5ma)

Compound 3ma (172 mg, 0.545 mmol, 1.0 equiv.) was used in a similar manner to synthesis step II of Example 1 to afford compound 5ma as a yellowish green solid (112 mg, 0.435 mmol, 80%). NMR data for compound 5ma are given as follow:

$^1$H NMR (600 MHz, CDCl$_3$) δ 7.64 (d, J=8.4 Hz, 2H), 7.59 (d, J=8.4 Hz, 2H), 6.92 (d, J=1.8 Hz, 1H), 6.00 (d, J=1.8 Hz, 1H), 2.86 (s, 3H); $^{13}$CNMR (150 MHz, CDCl$_3$) δ 150.6, 141.7, 138.1, 129.6, 129.4, 129.2, 129.0, 127.0, 126.0, 125.93, 125.91, 125.9, 125.6, 125.2, 123.4, 121.6, 117.0, 96.3, 32.7; $^{19}$F NMR (600 MHz, CDCl$_3$) δ −62.5; LRMS (APCI): m/z calcd for C$_{12}$H$_{11}$F$_3$NS [M+H]$^+$ 258.06, found 257.84.

<2-41> Synthesis of Methyl 2-(4-methoxyphenyl)-4-methyl-5-oxo-4,5,6,7-tetrahydrothieno[3,2-b]pyridine-7-carboxylate (6ba)

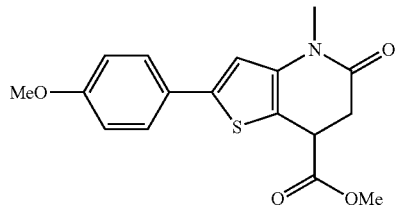 [SMILES: COC(=O)C1CC(=O)N(C)c2cc(-c3ccc(OC)cc3)sc21]

Methyl 2-(4-methoxyphenyl)-4-methyl-5-oxo-4,5,6,7-tetrahydrothieno[3,2-b]pyridine-7-carboxylate (6ba)

Compound 5ba (50.0 mg, 0.228 mmol, 1.0 equiv.) was used in a similar manner to synthesis step III of Example 1 to afford compound 6ba as a yellow solid (36.3 mg, 0.109 mmol, 48%). NMR data for compound 6ba are given as follow:

$^1$H NMR (600 MHz, CDCl$_3$) δ 7.48 (dd, J=6.9 Hz and J=1.8 Hz, 2H), 6.92 (dd, J=6.6 Hz and J=1.8 Hz, 2H), 6.88 (s, 1H), 4.01 (t, J=7.5 Hz, 1H), 3.84 (s, 3H), 3.79 (s, 3H), 3.35 (s, 3H), 3.02 (ddd, J=48.9 Hz, J=16.2 Hz and J=7.5 Hz, 2H); $^{13}$CNMR (150 MHz, CDCl$_3$) δ 171.4, 167.2, 159.8, 143.9, 140.3, 126.9, 126.7, 114.5, 112.4, 111.3, 55.5, 52.9, 38.4, 34.5, 30.6; LRMS (APCI): m/z calcd for C$_{17}$H$_{18}$NO$_4$S [M+H]$^+$ 332.10, found 331.81.

<2-42> Synthesis of Methyl 2-(3-methoxyphenyl)-4-methyl-5-oxo-4,5,6,7-tetrahydrothieno[3,2-b]pyridine-7-carboxylate (6bb)

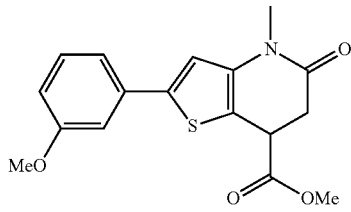 [SMILES: COC(=O)C1CC(=O)N(C)c2cc(-c3cccc(OC)c3)sc21]

Methyl 2-(3-methoxyphenyl)-4-methyl-5-oxo-4,5,6,7-tetrahydrothieno[3,2-b]pyridine-7-carboxylate (6bb)

Compound 5bb (121 mg, 0.552 mmol, 1.0 equiv.) was used in a similar manner to synthesis step III of Example 1 to afford compound 6bb as a yellow solid (106 mg, 0.320 mmol, 58%). NMR data for compound 6bb are given as follow:

$^1$H NMR (500 MHz, CDCl$_3$) δ 7.28 (t, J=8.0 Hz, 1H), 7.13 (d, J=8.5 Hz, 1H), 7.05-7.06 (m, 1H), 6.96 (s, 1H), 6.84 (dd, J=2.3 Hz and J=8.3 Hz, 1H), 4.01 (t, J=7.5 Hz, 1H), 3.83 (s, 3H), 3.77 (s, 3H), 3.33 (s, 3H), 3.00 (ddd, J=46.8 Hz, J=19.2 Hz and J=8.9 Hz, 2H); $^{13}$CNMR (125 MHz, CDCl$_3$) δ 171.2, 167.0, 160.1, 143.5, 140.3, 135.0, 130.1, 118.0, 113.5, 113.4, 112.5, 111.2, 55.4, 52.8, 38.3, 34.3, 30.5; LRMS (APCI): m/z calcd for C$_{17}$H$_{18}$NO$_4$S [M+H]$^+$ 332.10, found 331.86.

<2-43> Synthesis of Methyl 2-(2-methoxyphenyl)-4-methyl-5-oxo-4,5,6,7-tetrahydrothieno[3,2-b]pyridine-7-carboxylate (6bc)

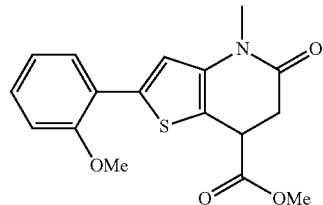 [SMILES: COC(=O)C1CC(=O)N(C)c2cc(-c3ccccc3OC)sc21]

Methyl 2-(2-methoxyphenyl)-4-methyl-5-oxo-4,5,6,7-tetrahydrothieno[3,2-b]pyridine-7-carboxylate (6bc)

Compound 5bc (136 mg, 0.620 mmol, 1.0 equiv.) was used in a similar manner to synthesis step III of Example 1 to afford compound 6bc as a pale brown solid (134 mg, 0.404 mmol, 65%). NMR data for compound 6bc are given as follow:

$^1$H NMR (500 MHz, CDCl$_3$) δ 7.59 (d, J=7.5 Hz, 1H), 7.28 (t, J=7.8 Hz, 1H), 7.17 (s, 1H), 7.01-6.98 (m, 2H), 4.02 (t, J=7.3 Hz, 1H), 3.94 (s, 3H), 3.77 (s, 3H), 3.36 (s, 3H), 3.02 (ddd, J=57.8 Hz, J=19.4 Hz and J=8.6 Hz, 2H); $^{13}$CNMR (125 MHz, CDCl$_3$) δ 171.5, 167.2, 155.8, 139.6, 139.0, 129.0, 128.0, 122.6, 121.1, 115.3, 113.1, 111.7, 55.7, 52.8, 38.4, 34.5, 30.5; LRMS (APCI): m/z calcd for C$_{17}$H$_{18}$NO$_4$S [M+H]$^+$ 332.10, found 331.94.

<2-44> Synthesis of Methyl 2-(4-methoxyphenyl)-5-oxo-4,5,6,7-tetrahydrothieno[3,2-b]pyridine-7-carboxylate (6bd)

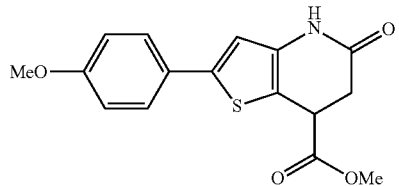 [SMILES: COC(=O)C1CC(=O)Nc2cc(-c3ccc(OC)cc3)sc21]

Methyl 2-(4-methoxyphenyl)-5-oxo-4,5,6,7-tetrahydrothieno[3,2-b]pyridine-7-carboxylate (6bd)

Compound 5bd (70.0 mg, 0.341 mmol, 1.0 equiv.) was used in a similar manner to synthesis step III of Example 1 to afford compound 6bd as a pale yellow solid (58.9 mg, 0.186 mmol, 54%). NMR data for compound 6bd are given as follow:

$^1$H NMR (600 MHz, CDCl$_3$) δ 8.28 (s, 1H), 7.46 (d, J=9.0 Hz, 2H), 6.90 (d, J=8.4 Hz, 2H), 6.74 (s, 1H), 4.06 (t, J=6.9 Hz, 1H), 3.83 (s, 3H), 3.79 (s, 3H), 3.00 (ddd, J=57.5 Hz, J=16.4 Hz and J=7.1 Hz, 2H); $^{13}$CNMR (150 MHz, CDCl$_3$) δ 171.4, 169.0, 159.8, 144.6, 136.8, 127.0, 126.5, 114.5, 112.5, 110.1, 55.5, 52.9, 38.8, 33.8; LRMS (APCI): m/z calcd for C$_{16}$H$_{16}$NO$_4$S [M+H]$^+$ 318.08, found 317.68.

<2-45> Synthesis of Methyl 4-benzyl-2-(4-methoxyphenyl)-5-oxo-4,5,6,7-tetrahydrothieno[3,2-b]pyridine-7-carboxylate (6be)

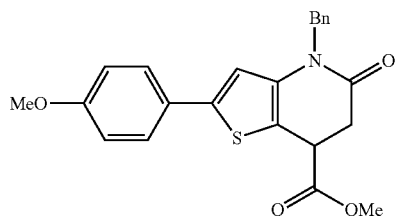 [SMILES: COC(=O)C1CC(=O)N(Cc2ccccc2)c2cc(-c3ccc(OC)cc3)sc21]

Methyl 4-benzyl-2-(4-methoxyphenyl)-5-oxo-4,5,6,7-tetrahydrothieno[3,2-b]pyridine-7-carboxylate (6be)

Compound 5be (69.4 mg, 0.235 mmol, 1.0 equiv.) was used in a similar manner to synthesis step III of Example 1 to afford compound 6be as a yellow solid (73.3 mg, 0.180 mmol, 77%). NMR data for compound 6be are given as follow:

$^1$H NMR (600 MHz, CDCl$_3$) δ 7.36 (dd, J=4.2 Hz and J=2.4 Hz, 2H), 7.31 (t, J=7.5 Hz, 2H), 7.28-7.24 (m, 3H), 6.86 (dd, J=6.6 Hz and J=1.8 Hz, 2H), 6.73 (s, 1H), 5.19 (d, J=16.2 Hz, 1H), 4.99 (d, J=16.2 Hz, 1H), 4.04 (t, J=6.9 Hz, 1H), 3.81 (s, 3H), 3.77 (s, 3H), 3.13 (ddd, J=47.7 Hz, J=16.2 Hz and J=6.9 Hz, 2H); $^{13}$CNMR (150 MHz, CDCl$_3$) δ 171.4, 167.4, 159.7, 143.7, 139.6, 137.0, 128.9, 127.5, 126.94, 126.92, 126.6, 114.5, 112.9, 111.8, 55.5, 52.9, 47.0, 38.5, 34.7; LRMS (APCI): m/z calcd for C$_{23}$H$_{20}$NO$_4$S [M–H]$^-$ 406.11, found 406.00.

<2-46> Synthesis of 2-(4-Methoxyphenyl)-4-methyl-6,7-dihydrothieno[3,2-b]pyridine-5(4H)-one (6bf)

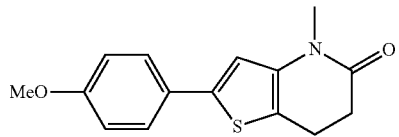 [SMILES: COc1ccc(-c2cc3c(s2)CCC(=O)N3C)cc1]

2-(4-Methoxyphenyl)-4-methyl-6,7-dihydrothieno[3,2-b]pyridine-5(4H)-one (6bf)

Compound 5ba (40.0 mg, 0.182 mmol, 1.0 equiv.) was used in a similar manner to synthesis step III of Example 1 to afford compound 6bf as a white solid (38.2 mg, 0.140 mmol, 77%). NMR data for compound 6bf are given as follow:

$^1$H NMR (600 MHz, CDCl$_3$) δ 7.46 (dd, J=9.5 Hz and J=2.4 Hz, 2H), 6.91 (dd, J=9.5 Hz and J=2.4 Hz, 2H), 6.87 (s, 1H), 3.83 (s, 3H), 3.34 (s, 3H), 2.94 (t, J=7.8 Hz, 2H), 2.78 (t, J=7.8 Hz, 2H); $^{13}$CNMR (150 MHz, CDCl$_3$) δ 168.7, 159.5, 141.6, 139.8, 127.0, 126.8, 115.3, 114.5, 112.5, 55.5, 32.3, 30.5, 20.8; LRMS (APCI): m/z calcd for C$_{15}$H$_{16}$NO$_2$S [M+H]$^+$ 274.09, found 273.80.

<2-47> Synthesis of Methyl 4-methyl-5-oxo-2-(4-phenoxyphenyl)-4,5,6,7-tetrahydrothieno[3,2-b]pyridine-7-carboxylate (6ca)

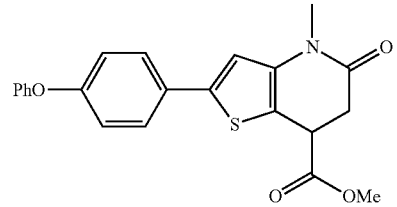

Methyl 4-methyl-5-oxo-2-(4-phenoxyphenyl)-4,5,6,7-tetrahydrothieno[3,2-b]pyridine-7-carboxylate (6ca)

Compound 5ca (33.0 mg, 0.117 mmol, 1.0 equiv.) was used in a similar manner to synthesis step III of Example 1 to afford compound 6ca as a yellow solid (25.0 mg, 0.0635 mmol, 54%). NMR data for compound 6ca are given as follow:

$^1$H NMR (600 MHz, CDCl$_3$) δ 7.51 (dd, J=6.6 Hz and J=2.4 Hz, 2H), 7.38-7.35 (m, 2H), 7.14 (tt, J=7.8 Hz and J=2.4 Hz, 1H), 7.05-7.04 (m, 2H), 7.02 (dd, J=2.4 Hz and J=6.6 Hz, 2H), 6.91 (s, 1H), 4.02 (t, J=7.2 Hz, 1H), 3.79 (s, 3H), 3.35 (s, 3H), 3.03 (ddd, J=47.1 Hz, J=16.5 Hz and J=7.2 Hz, 2H); $^{13}$CNMR (150 MHz, CDCl$_3$) δ 171.3, 167.1, 157.6, 156.8, 143.3, 140.4, 130.0, 128.9, 127.1, 123.8, 119.3, 119.2, 112.9, 111.9, 52.9, 38.4, 34.4, 30.6; LRMS (APCI): m/z calcd for C$_{22}$H$_{20}$NO$_4$S [M+H]$^+$ 394.11, found 394.02.

<2-48> Synthesis of Methyl 2-(benzo[d][1,3]dioxol-5-yl)-4-methyl-5-oxo-4,5,6,7-tetrahydrothieno[3,2-b]pyridine-7-carboxylate (6da)

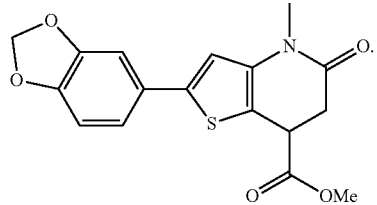 [SMILES: COC(=O)C1CC(=O)N(C)c2cc(-c3ccc4c(c3)OCO4)sc21]

Methyl 2-(benzo[d][1,3]dioxol-5-yl)-4-methyl-5-oxo-4,5,6,7-tetrahydrothieno[3,2-b]pyridine-7-carboxylate (6da)

Compound 5da (40.5 mg, 0.174 mmol, 1.0 equiv.) was used in a similar manner to synthesis step III of Example 1 to afford compound 6da as a yellow solid (32.8 mg, 0.0950 mmol, 55%). NMR data for compound 6da are given as follow:

$^1$H NMR (500 MHz, CDCl$_3$) δ 7.03 (dd, J=8.0 Hz and J=2.0 Hz, 1H), 7.00 (d, J=2.0 Hz, 1H), 6.83 (s, 1H), 6.79 (d, J=8.0 Hz, 1H), 5.97 (s, 2H), 3.99 (t, J=7.3 Hz, 1H), 3.77 (s, 3H), 3.32 (s, 3H), 3.00 (ddd, J=49.4 Hz, J=19.7 Hz and J=8.9 Hz, 2H); $^{13}$CNMR (150 MHz, CDCl$_3$) δ 171.3, 167.1, 148.3, 147.8, 143.7, 140.2, 128.1, 119.4, 112.7, 111.5, 108.8, 106.2, 101.5, 52.8, 38.3, 34.4, 30.5; LRMS (APCI): m/z calcd for C$_{17}$H$_{16}$NO$_5$S [M+H]$^+$ 346.07, found 345.95.

<2-49> Synthesis of Methyl 2-(2,3-dihydrobenzo[b][1,4]dioxin-6-yl)-4-methyl-5-oxo-4,5,6,7-tetrahydrothieno[3,2-b]pyridine-7-carboxylate (6ea)

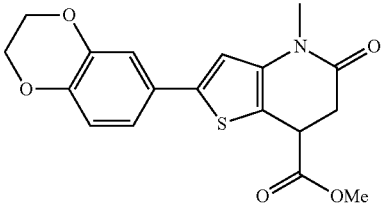 [SMILES: COC(=O)C1CC(=O)N(C)c2cc(-c3ccc4c(c3)OCCO4)sc21]

Methyl 2-(2,3-dihydrobenzo[b][1,4]dioxin-6-yl)-4-methyl-5-oxo-4,5,6,7-tetrahydrothieno[3,2-b]pyridine-7-carboxylate (6ea)

Compound 5ea (145 mg, 0.586 mmol, 1.0 equiv.) was used in a similar manner to synthesis step III of Example 1 to afford compound 6ea as a yellow oil (130 mg, 0.362 mmol, 62%). NMR data for compound 6ea are given as follow:

$^1$H NMR (500 MHz, CDCl$_3$) δ 7.02 (d, J=2.0 Hz, 1H), 6.99 (dd, J=2.3 Hz and J=9.0 Hz, 1H), 6.82-6.80 (m, 2H), 4.23 (s, 4H), 3.95 (t, J=7.3 Hz, 1H), 3.74 (s, 3H), 3.28 (s, 3H), 2.96 (ddd, J=51.9 Hz, J=19.8 Hz and J=8.7 Hz, 2H); $^{13}$CNMR (125 MHz, CDCl$_3$) δ 171.2, 167.0, 143.8, 143.7, 143.3, 140.1, 127.3, 118.7, 117.7, 114.3, 112.5, 111.4, 64.44, 64.39, 52.7, 38.2, 34.3, 30.4; LRMS (APCI): m/z calcd for C$_{18}$H$_{16}$NO$_5$S [M–H]$^-$ 358.07, found 357.99.

<2-50> Synthesis of Methyl 4-methyl-5-oxo-2-(3,4,5-trimethoxyphenyl)-4,5,6,7-tetrahydrothieno[3,2-b]pyridine-7-carboxylate (6fa)

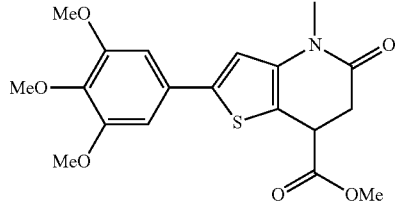 [SMILES: COC(=O)C1CC(=O)N(C)c2cc(-c3cc(OC)c(OC)c(OC)c3)sc21]

Methyl 4-methyl-5-oxo-2-(3,4,5-trimethoxyphenyl)-4,5,6,7-tetrahydrothieno[3,2-b]pyridine-7-carboxylate (6fa)

Compound 5fa (80.0 mg, 0.286 mmol, 1.0 equiv.) was used in a similar manner to synthesis step III of Example 1 to afford compound 6fa as a yellow oil (60.4 mg, 0.154 mmol, 54%). NMR data for compound 6fa are given as follow:

$^1$H NMR (600 MHz, CDCl$_3$) δ 6.89 (s, 1H), 6.73 (s, 2H), 4.02 (t, J=7.5 Hz, 1H), 3.91 (s, 6H), 3.86 (s, 3H), 3.79 (s, 3H), 3.36 (s, 3H), 3.02 (ddd, J=38.4 Hz, J=16.2 Hz and J=7.2 Hz, 2H); $^{13}$CNMR (150 MHz, CDCl$_3$) δ 171.3, 167.2, 153.7, 144.0, 140.2, 138.4, 129.6, 113.2, 112.2, 103.2, 61.1, 56.4, 52.9, 38.3, 34.4, 30.7; LRMS (APCI): m/z calcd for C$_{19}$H$_2$NO$_6$S [M–H]$^-$ 390.10, found 390.06.

<2-51> Synthesis of Methyl 2-(4-(dimethylamino)phenyl)-4-methyl-5-oxo-4,5,6,7-tetrahydrothieno[3,2-b]pyridine-7-carboxylate (6ga)

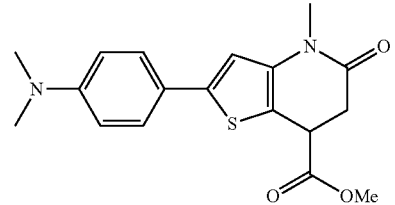 [SMILES: COC(=O)C1CC(=O)N(C)c2cc(-c3ccc(N(C)C)cc3)sc21]

Methyl 2-(4-(dimethylamino)phenyl)-4-methyl-5-oxo-4,5,6,7-tetrahydrothieno[3,2-b]pyridine-7-carboxylate (6ga)

Compound 5ga (91.6 mg, 0.394 mmol, 1.0 equiv.) used in a similar manner to synthesis step III of Example 1 to afford compound 6ga as an orange-brown solid (83.1 mg, 0.241 mmol, 61%). NMR data for compound 6ga are given as follow:

$^1$H NMR (600 MHz, CDCl$_3$) δ 7.43 (d, J=9.0 Hz, 2H), 6.82 (s, 1H), 6.72 (d, J=7.8 Hz, 2H), 3.99 (t, J=7.2 Hz, 1H), 3.78 (s, 3H), 3.34 (s, 3H), 3.02 (m, 8H); $^{13}$CNMR (150 MHz, CDCl$_3$) δ 171.6, 167.3, 150.4, 144.8, 140.2, 126.6, 122.1, 112.6, 111.1, 110.0, 52.8, 40.6, 38.4, 34.5, 30.6; LRMS (APCI): m/z calcd for C$_{18}$H$_{21}$N$_2$O$_3$S [M+H]$^+$ 345.13, found 345.12.

<2-52> Synthesis of Methyl 2-(3-(dimethylamino)phenyl)-4-methyl-5-oxo-4,5,6,7-tetrahydrothieno[3,2-b]pyridine-7-carboxylate (6gb)

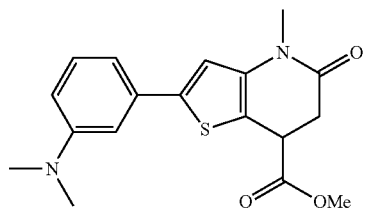 [SMILES: COC(=O)C1CC(=O)N(C)c2cc(-c3cccc(N(C)C)c3)sc21]

Methyl 2-(3-(dimethylamino)phenyl)-4-methyl-5-oxo-4,5,6,7-tetrahydrothieno[3,2-b]pyridine-7-carboxylate (6gb)

Compound 5gb (114 mg, 0.491 mmol, 1.0 equiv.) was used in a similar manner to synthesis step III of Example 1 to afford compound 6gb as a brown solid (102 mg, 0.296 mmol, 61%). NMR data for compound 6gb are given as follow:

$^1$H NMR (600 MHz, CDCl$_3$) δ 7.24 (t, J=8.1 Hz, 1H), 6.96 (s, 1H), 6.92 (d, J=7.8 Hz, 1H), 6.86 (s, 1H), 6.70 (dd, J=8.4 Hz and J=2.4 Hz, 1H), 4.02 (t, J=7.2 Hz, 1H), 3.78 (s, 3H), 3.35 (s, 3H), 3.08-2.96 (m, 8H); $^{13}$CNMR (150 MHz, CDCl$_3$) δ 171.4, 167.2, 151.0, 144.9, 140.2, 134.5, 129.8, 114.2, 113.1, 112.5, 112.0, 109.5, 52.9, 40.7, 38.4, 34.4, 30.6; LRMS (APCI): m/z calcd for C$_{18}$H$_{21}$N$_2$O$_3$S [M+H]$^+$ 345.13, found 344.80.

<2-53> Synthesis of Methyl 2-(2-(dimethylamino)phenyl)-4-methyl-5-oxo-4,5,6,7-tetrahydrothieno[3,2-b]pyridine-7-carboxylate (6gc)

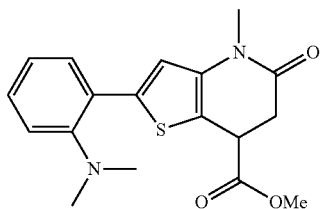 [SMILES: COC(=O)C1CC(=O)N(C)c2cc(-c3ccccc3N(C)C)sc21]

Methyl 2-(2-(dimethylamino)phenyl)-4-methyl-5-oxo-4,5,6,7-tetrahydrothieno[3,2-b]pyridine-7-carboxylate (6gc)

Compound 5gc (105 mg, 0.452 mmol, 1.0 equiv.) was used in a similar manner to synthesis step III of Example 1 to afford compound 6gc as a yellow liquid (118 mg, 0.342 mmol, 76%). NMR data for compound 6gc are given as follow:

$^1$H NMR (600 MHz, CDCl$_3$) δ 7.52 (d, J=7.8 Hz, 1H), 7.24 (t, J=7.5 Hz, 1H), 7.16 (d, J=8.4 Hz, 1H), 7.12 (s, 1H), 7.06 (t, J=7.2 Hz, 1H), 4.03 (t, J=6.9 Hz, 1H), 3.79 (s, 3H), 3.38 (s, 3H), 3.04 (ddd, J=7.1 Hz, J=16.4 Hz and J=60.2 Hz, 2H), 2.65 (s, 6H); $^{13}$CNMR (150 MHz, CDCl$_3$) δ 171.6, 167.2, 151.0, 140.9, 139.0, 128.6, 128.5, 128.4, 123.6, 120.5, 114.5, 113.9, 52.7, 44.4, 38.4, 34.5, 30.4; LRMS (APCI): m/z calcd for C$_{18}$H$_{21}$N$_2$O$_3$S [M+H]$^+$ 345.13, found 345.00.

<2-54> Synthesis of Methyl 4-benzyl-2-(4-(dimethylamino)phenyl)-5-oxo-4,5,6,7-tetrahydrothieno[3,2-b]pyridine-7-carboxylate (6gd)

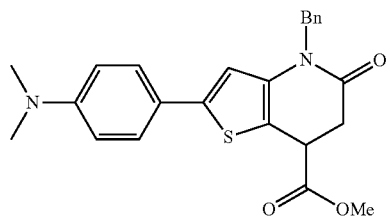 [SMILES: COC(=O)C1CC(=O)N(Cc2ccccc2)c2cc(-c3ccc(N(C)C)cc3)sc21]

Methyl 4-benzyl-2-(4-(dimethylamino)phenyl)-5-oxo-4,5,6,7-tetrahydrothieno[3,2-b]pyridine-7-carboxylate (6gd)

Compound 5gd (60.0 mg, 0.194 mmol, 1.0 equiv.) was used in a similar manner to synthesis step III of Example 1 to afford compound 6gd as a pale red solid (66.3 mg, 0.158 mmol, 81%). NMR data for compound 6gd are given as follow:

$^1$H NMR (600 MHz, CDCl$_3$) δ 7.33-7.27 (m, 6H), 7.25-7.22 (m, 1H), 6.69 (s, 1H), 6.67 (d, J=8.4 Hz, 2H), 5.19 (d, J=15.6 Hz, 1H), 4.99 (d, J=15.6 Hz, 1H), 4.02 (t, J=6.6 Hz, 1H), 3.77 (s, 3H), 3.12 (ddd, J=49.8 Hz, J=16.2 Hz and J=6.6 Hz, 2H), 2.96 (s, 6H); $^{13}$CNMR (150 MHz, CDCl$_3$) δ 171.4, 167.4, 150.3, 144.6, 139.4, 137.0, 128.7, 127.3, 126.9, 126.5, 121.9, 112.4, 111.6, 110.3, 52.7, 46.8, 40.4, 38.4, 34.6; LRMS (APCI): m/z calcd for C$_{24}$H$_{25}$N$_2$O$_3$S [M+H]$^+$ 421.16, found 421.07.

<2-55> Synthesis of Methyl 2-(4-(diethylamino)phenyl)-4-methyl-5-oxo-4,5,6,7-tetrahydrothieno[3,2-b]pyridine-7-carboxylate (6ha)

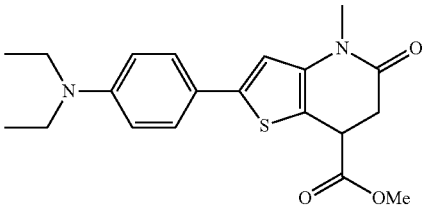

Methyl 2-(4-(diethylamino)phenyl)-4-methyl-5-oxo-4,5,6,7-tetrahydrothieno[3,2-b]pyridine-7-carboxylate (6ha)

Compound 5ha (160 mg, 0.614 mmol, 1.0 equiv.) was used in a similar manner to synthesis step III of Example 1 to afford compound 6ha as an orange yellow solid (166 mg, 0.446 mmol, 73%). NMR data for compound 6ha are given as follow:
$^1$H NMR (500 MHz, CDCl$_3$) δ 7.39 (d, J=8.5 Hz, 2H), 6.79 (s, 1H), 6.64 (d, J=8.5 Hz, 2H), 3.97 (t, J=7.0 Hz, 1H), 3.77 (s, 3H), 3.38 (q, J=7.2 Hz, 4H), 3.33 (s, 3H), 3.00 (ddd, J=46.6 Hz, J=16.3 Hz and J=7.1 Hz, 2H), 1.18 (t, J=7.3 Hz, 6H); $^{13}$CNMR (125 MHz, CDCl$_3$) δ 171.5, 167.2, 147.7, 145.0, 140.1, 126.7, 120.9, 111.7, 110.7, 109.5, 52.7, 44.4, 38.3, 34.5, 30.5, 12.7; LRMS (APCI): m/z calcd for C$_{20}$H$_{25}$N$_2$O$_3$S [M+H]$^+$ 373.16, found 373.04.

<2-56> Synthesis of Methyl 4-methyl-2-(4-(4-methylpiperazin-1-yl)phenyl)-5-oxo-4,5,6,7-tetrahydrothieno[3,2-b]pyridine-7-carboxylate (6ia)

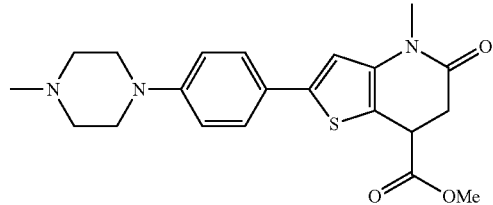 [SMILES: COC(=O)C1CC(=O)N(C)c2cc(-c3ccc(N4CCN(C)CC4)cc3)sc21]

Methyl 4-methyl-2-(4-(4-methylpiperazin-1-yl)phenyl)-5-oxo-4,5,6,7-tetrahydrothieno[3,2-b]pyridine-7-carboxylate (6ia)

Compound 5ia (50.0 mg, 0.174 mmol, 1.0 equiv.) was used in a similar manner to synthesis step III of Example 1 to afford compound 6ia as a pale orange yellow solid (26.1 mg, 0.0653 mmol, 38%). In addition, the reaction mixture was purified by flash column chromatography (DCM/MeOH=15/1, v/v) on silica. NMR data for compound 6ia are given as follow:
$^1$H NMR (600 MHz, CDCl$_3$) δ 7.45 (d, J=8.4 Hz, 2H), 6.91 (d, J=9.0 Hz, 2H), 6.86 (s, 1H), 4.00 (t, J=7.2 Hz, 1H), 3.78 (s, 3H), 3.34 (s, 3H), 3.30-3.28 (m, 4H), 3.02 (ddd, J=49.8 Hz, J=16.2 Hz and J=7.2 Hz, 2H), 2.34-2.62 (m, 4H), 2.39 (s, 3H); $^{13}$CNMR (150 MHz, CDCl$_3$) δ 171.5, 167.2, 151.0, 144.2, 140.3, 126.6, 125.2, 116.0, 111.9, 110.8, 55.0, 52.9, 48.5, 46.1, 38.4, 34.5, 30.6; LRMS (APCI): m/z calcd for C$_{21}$H$_{26}$N$_3$O$_3$S [M+H]$^+$ 400.17, found 400.11.

<2-57> Synthesis of Methyl 4-methyl-5-oxo-2-(2,3,6,7-tetrahydro-1H, 5H-pyrido[3,2,1-ij]quinolin-9-yl)-4,5,6,7-tetrahydrothieno[3,2-b]pyridine-7-carboxylate (6ja)

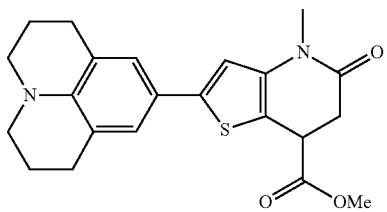 [SMILES: COC(=O)C1CC(=O)N(C)c2cc(-c3cc4c5c(c3)CCCN5CCC4)sc21]

Methyl 4-methyl-5-oxo-2-(2,3,6,7-tetrahydro-1H, 5H-pyrido[3,2,1-ij]quinolin-9-yl)-4,5,6,7-tetrahydrothieno[3,2-b]pyridine-7-carboxylate (6ja)

Compound 5ja (70.0 mg, 0.246 mmol, 1.0 equiv.) was used in a similar manner to synthesis step III of Example 1 to afford compound 6ja as an orange yellow solid (63.6 mg, 0.160 mmol, 65%). NMR data for compound 6ja are given as follow:
$^1$H NMR (500 MHz, CDCl$_3$) δ 7.00 (s, 2H), 6.77 (s, 1H), 3.98 (t, J=7.3 Hz, 1H), 3.78 (s, 3H), 3.34 (s, 3H), 3.19 (m, 4H), (ddd, J=44.0 Hz, J=16.3 Hz and J=7.8 Hz, 2H) 2.78 (t, J=6.5 Hz, 4H), 2.00 (m, 4H); $^{13}$CNMR (125 MHz, CDCl$_3$) δ 171.6, 167.3, 145.3, 143.1, 140.1, 125.0, 124.4, 121.7, 121.6, 121.1, 110.6, 109.4, 52.8, 50.1, 38.4, 34.6, 30.6, 27.8, 22.0; LRMS (APCI): m/z calcd for C$_{22}$H$_{25}$N$_2$O$_3$S [M+H]$^+$ 397.16, found 397.12.

<2-58> Synthesis of Methyl 2-(4-methoxyphenyl)-4-methyl-5-oxo-4,5-dihydrothieno[3,2-b]pyridine-7-carboxylate (8ba)

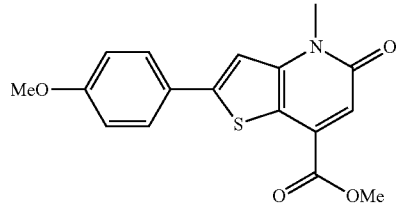

Methyl 2-(4-methoxyphenyl)-4-methyl-5-oxo-4,5-dihydrothieno[3,2-b]pyridine-7-carboxylate (8ba)

Compound 6ba (60.0 mg, 0.181 mmol, 1.0 equiv.) was used in a similar manner to synthesis step IV of Example 1 to afford compound 8ba as a yellow solid (29.5 mg, 0.0896 mmol, 50%). NMR data for compound 8ba are given as follow:
$^1$H NMR (600 MHz, CDCl$_3$) δ 7.65 (d, J=9.0 Hz, 2H), 7.22 (s, 1H), 7.17 (s, 1H), 6.97 (d, J=9.0 Hz, 2H), 4.01 (s, 3H), 3.87 (s, 3H), 3.79 (s, 3H); $^{13}$CNMR (150 MHz, CDCl$_3$) δ 165.2, 162.5, 160.8, 151.6, 146.0, 134.1, 127.7, 126.0, 118.1, 114.8, 110.1, 55.6, 53.3, 32.4.

<2-59> Synthesis of Methyl 2-(3-methoxyphenyl)-4-methyl-5-oxo-4,5-dihydrothieno[3,2-b]pyridine-7-carboxylate (8bb)

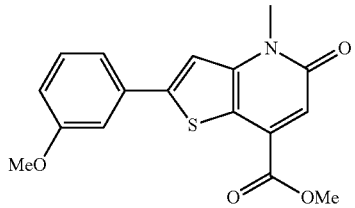 [SMILES: COC(=O)c1cc(=O)n(C)c2cc(-c3cccc(OC)c3)sc12]

Methyl 2-(3-methoxyphenyl)-4-methyl-5-oxo-4,5-dihydrothieno[3,2-b]pyridine-7-carboxylate (8bb)

Compound 6bb (85.1 mg, 0.257 mmol, 1.0 equiv.) was used in a similar manner to synthesis step IV of Example 1 to afford compound 8bb as a yellow solid (54.8 mg, 0.166 mmol, 65%). NMR data for compound 8bb are given as follow:

$^1$H NMR (600 MHz, CDCl$_3$) δ 7.40 (t, J=8.1 Hz, 1H), 7.34 (d, J=7.2 Hz, 1H), 7.29 (d, J=4.2 Hz, 2H), 7.26-7.25 (m, 1H), 6.98 (dd, J=8.1 Hz and J=2.7 Hz, 1H), 4.05 (s, 3H), 3.92 (s, 3H), 3.82 (s, 3H); $^{13}$CNMR (150 MHz, CDCl$_3$) δ 165.1, 162.3, 160.3, 151.0, 145.7, 134.6, 134.0, 130.4, 119.0, 118.8, 115.6, 115.0, 111.8, 111.4, 55.6, 53.3, 32.3; LRMS (APCI): m/z calcd for C$_{17}$H$_{16}$NO$_4$S [M+H]$^+$ 330.08, found 329.78.

<2-60> Synthesis of Methyl 2-(2-methoxyphenyl)-4-methyl-5-oxo-4,5-dihydrothieno[3,2-b]pyridine-7-carboxylate (8bc)

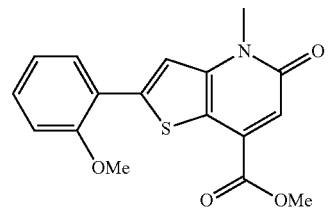 [SMILES: COC(=O)c1cc(=O)n(C)c2cc(-c3ccccc3OC)sc12]

Methyl 2-(2-methoxyphenyl)-4-methyl-5-oxo-4,5-dihydrothieno[3,2-b]pyridine-7-carboxylate (8bc)

Compound 6bc (98.6 mg, 0.297 mmol, 1.0 equiv.) was used in a similar manner to synthesis step IV of Example 1 to afford compound 8bc as a yellow solid (47.8 mg, 0.145 mmol, 49%). NMR data for compound 8bc are given as follow:

$^1$H NMR (600 MHz, CDCl$_3$) δ 7.70 (dd, J=8.0 Hz and J=1.8 Hz, 1H), 7.45 (s, 1H), 7.35 (td, J=8.0 Hz and J=1.5 Hz, 1H), 7.17 (s, 1H), 7.05-7.01 (m, 2H), 3.98 (s, 3H), 3.97 (s, 3H), 3.75 (s, 3H); $^{13}$CNMR (150 MHz, CDCl$_3$) δ 165.3, 162.5, 156.5, 147.2, 145.2, 134.1, 130.5, 128.9, 122.1, 121.3, 118.6, 116.4, 113.6, 112.0, 55.8, 53.2, 32.3; LRMS (APCI): m/z calcd for C$_{17}$H$_{16}$NO$_4$S [M+H]$^+$ 330.08, found 329.92.

<2-61> Synthesis of Methyl 2-(4-methoxyphenyl)-5-oxo-4,5-dihydrothieno[3,2-b]pyridine-7-carboxylate (8bd)

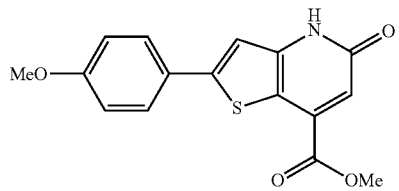 [SMILES: COC(=O)c1cc(=O)[nH]c2cc(-c3ccc(OC)cc3)sc12]

Methyl 2-(4-methoxyphenyl)-5-oxo-4,5-dihydrothieno[3,2-b] pyridine-7-carboxylate (8bd)

Compound 6bd (9.50 mg, 0.0299 mmol, 1.0 equiv.) was used in a similar manner to synthesis step IV of Example 1 to afford compound 8bd as a yellow solid (6.40 mg, 0.0203 mmol, 68%). NMR data for compound 8bd are given as follow:

$^1$H NMR (600 MHz, DMSO-d$_6$) δ 7.71 (d, J=7.8 Hz, 2H), 7.30 (s, 1H), 7.05 (d, J=8.4 Hz, 2H), 6.86 (s, 1H), 3.95 (s, 3H), 3.82 (s, 3H); $^{13}$CNMR (150 MHz, DMSO-d$_6$) δ 164.4, 162.1, 160.2, 149.6, 134.7, 127.4, 125.2, 114.8, 111.8, 55.4, 53.2; LRMS (APCI): m/z calcd for C$_{16}$H$_{14}$NO$_4$S [M+H]$^+$ 316.06, found 315.89.

<2-62> Synthesis of Methyl 4-benzyl-2-(4-methoxyphenyl)-5-oxo-4,5-dihydrothieno[3,2-b]pyridine-7-carboxylate (8be)

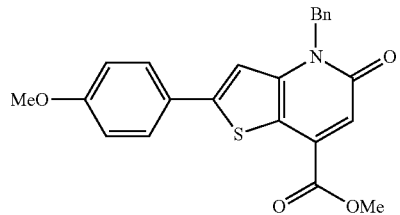 [SMILES: COC(=O)c1cc(=O)n(Cc2ccccc2)c2cc(-c3ccc(OC)cc3)sc12]

Methyl 4-benzyl-2-(4-methoxyphenyl)-5-oxo-4,5-dihydrothieno[3,2-b] pyridine-7-carboxylate (8be)

Compound 6be (42.3 mg, 0.104 mmol, 1.0 equiv.) was used in a similar manner to synthesis step IV of Example 1 to afford compound 8be as a yellow solid (17.8 mg, 0.0439 mmol, 42%). NMR data for compound 8be are given as follow:

$^1$H NMR (600 MHz, CDCl$_3$) δ 7.54 (dd, J=6.9 Hz and J=2.1 Hz, 2H), 7.32-7.26 (m, 6H), 7.06 (s, 1H), 6.93 (dd, J=6.6 Hz and J=1.8 Hz, 2H), 5.52 (s, 2H), 4.02 (s, 3H), 3.84 (s, 3H); $^{13}$CNMR (150 MHz, CDCl$_3$) δ 165.2, 162.4, 160.8, 151.4, 145.6, 135.9, 134.4, 129.1, 127.9, 127.7, 127.2, 126.0, 118.4, 115.4, 114.7, 110.7, 55.6, 53.3, 48.7; LRMS (APCI): m/z calcd for C$_{23}$H$_{20}$NO$_4$S [M+H]$^+$ 406.11, found 406.07.

<2-63> Synthesis of 2-(4-methoxyphenyl)-4,7-디메틸thieno[3,2-b] pyridine-5 (4H)-one (2-(4-Methoxyphenyl)-4,7-dimethylthieno[3,2-b]pyridine-5(4H)-one (8bg))의 합성

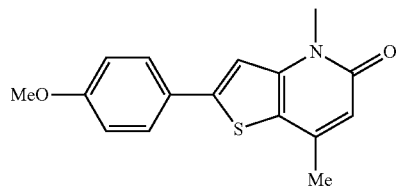 [SMILES: COc1ccc(-c2cc3c(s2)c(C)cc(=O)n3C)cc1]

2-(4-Methoxyphenyl)-4,7-dimethylthieno[3,2-b] pyridine-5(4H)-one (8bg)

Compound 5ba (56.4 mg, 0.257 mmol, 1.0 equiv.) and crotonic acid (26.6 mg, 0.309 mmol, 1.2 equiv.) were used in a similar manner to synthesis steps III and IV of Example 1 to afford compound 8bg as a white solid (15.9 mg, 0.0557 mmol, 22%, two steps). NMR data for compound 8bg are given as follow:

¹H NMR (600 MHz, CDCl₃) δ 7.58 (dd, J=6.6 Hz and J=2.4 Hz, 2H), 7.12 (s, 1H), 6.95 (dd, J=6.6 Hz and J=1.8 Hz, 2H), 6.37 (d, J=1.2 Hz, 1H), 3.85 (s, 3H), 3.69 (s, 3H), 2.35 (d, J=1.2 Hz, 3H); ¹³CNMR (150 MHz, CDCl₃) δ 162.8, 160.5, 147.5, 144.0, 127.5, 126.2, 119.3, 115.6, 114.7, 111.2, 55.6, 31.8, 19.8; LRMS (APCI): m/z calcd for $C_{16}H_{16}NO_2S$ [M+H]⁺ 286.09, found 285.77.

<2-64> Synthesis of 2-(4-Methoxyphenyl)-4-methyl-7-phenylthieno[3,2-b]pyridine-5 (4H)-one (8bh)

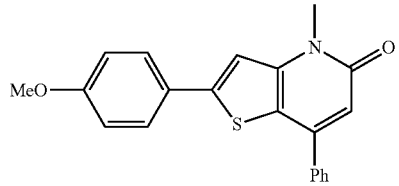 [SMILES: COc1ccc(-c2cc3c(s2)c(-c2ccccc2)cc(=O)n3C)cc1]

2-(4-Methoxyphenyl)-4-methyl-7-phenylthieno[3,2-b]pyridine-5(4H)-one (8bh)

Compound 5ba (68.8 mg, 0.314 mmol, 1.0 equiv.) and trans-cinnamic acid (55.8 mg, 0.376 mmol, 1.2 equiv.) were used in a similar manner to synthesis steps III and IV of Example to afford compound 8bh as a white solid (16.4 mg, 0.0472 mmol, 15%, two steps). NMR data for compound 8bh are given as follow:

¹H NMR (600 MHz, CDCl₃) δ 7.68-7.67 (m, 2H), 7.58 (d, J=8.4 Hz, 2H), 7.52-7.49 (m, 3H), 7.19 (s, 1H), 6.93 (d, J=8.4 Hz, 2H), 6.60 (s, 1H), 3.85 (s, 3H), 3.77 (s, 3H); ¹³CNMR (150 MHz, CDCl₃) δ 162.8, 160.6, 148.8, 147.1, 145.0, 137.5, 129.7, 129.1, 127.8, 127.5, 126.0, 117.4, 114.9, 114.7, 111.2, 55.6, 31.9; LRMS (APCI): m/z calcd for $C_{21}H_{18}NO_2S$ [M+H]⁺ 348.11, found 347.90.

<2-65> Synthesis of 7-Acetyl-2-(4-methoxyphenyl)-4-methylthieno[3,2-b]pyridine-5 (4H)-one (8bi)

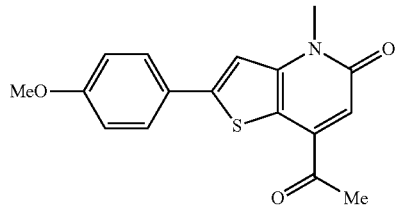

7-Acetyl-2-(4-methoxyphenyl)-4-methylthieno[3,2-b]pyridine-5(4H)-one (8bi)

Compound 5ba (30.0 mg, 0.137 mmol, 1.0 equiv.) and (E)-4-oxopent-2-enoic acid (18.7 mg, 0.164 mmol, 1.2 equiv.) were used in a similar manner to synthesis step III of Example 1 to afford compound 8bi as an orange yellow solid (19.6 mg, 0.0625 mmol, 46%). NMR data for compound 8bi are given as follow:

¹H NMR (600 MHz, CDCl₃) δ 7.64 (d, J=8.4 Hz, 2H), 7.13 (s, 1H), 7.09 (s, 1H), 6.96 (d, J=9.0 Hz, 2H), 3.86 (s, 3H), 3.78 (s, 3H), 2.65 (s, 3H); ¹³CNMR (150 MHz, CDCl₃) δ 197.9, 163.0, 160.8, 152.8, 146.1, 139.1, 127.7, 126.1, 118.3, 114.7, 113.1, 109.6, 55.6, 32.4, 26.3; LRMS (APCI): m/z calcd for $C_{17}H_{16}NO_3S$ [M+H]⁺ 314.09, found 313.74.

<2-66> Synthesis of 7-Acetyl-4-benzyl-2-(4-methoxyphenyl)thieno[3,2-b]pyridine-5(4H)-one (8bj)

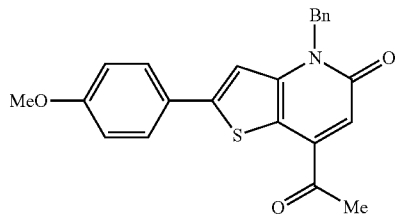

7-Acetyl-4-benzyl-2-(4-methoxyphenyl)thieno[3,2-b]pyridine-5(4H)-one (8bj)

Compound 5be (60.0 mg, 0.203 mmol, 1.0 equiv.) and (E)-4-oxopent-2-enoic acid (27.8 mg, 0.244 mmol, 1.2 equiv.) were used in a similar manner to synthesis step III of Example 1 to afford compound 8bj as a green solid (20.4 mg, 0.0524 mmol, 26%). NMR data for compound 8bj are given as follow:

¹H NMR (600 MHz, CDCl₃) δ 7.54 (dd, J=6.6 Hz and J=1.8 Hz, 2H), 7.33-7.24 (m, 5H), 7.17 (s, 1H), 7.05 (s, 1H), 6.92 (dd, J=6.9 Hz and J=2.1 Hz, 2H), 5.52 (s, 2H), 3.83 (s, 3H), 2.67 (s, 3H); ¹³CNMR (150 MHz, CDCl₃) δ 197.9, 163.0, 160.7, 152.8, 145.8, 139.4, 135.8, 129.0, 127.9, 127.7, 127.1, 126.1, 118.5, 114.6, 113.5, 110.1, 55.5, 48.7, 26.4; LRMS (APCI): m/z calcd for $C_{23}H_{20}NO_3S$ [M+H]⁺ 390.12, found 390.05.

<2-67> Synthesis of 7-Benzoyl-4-benzyl-2-(4-methoxyphenyl)thieno[3,2-b]pyridine-5(4H)-one (8bk)

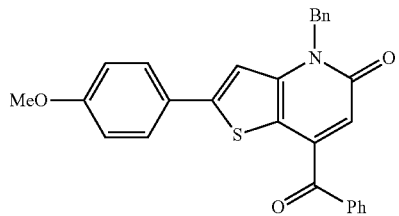 [SMILES: COc1ccc(-c2cc3c(s2)c(C(=O)c2ccccc2)cc(=O)n3Cc2ccccc2)cc1]

7-Benzoyl-4-benzyl-2-(4-methoxyphenyl)thieno[3,2-b]pyridine-5(4H)-one (8bk)

Compound 5be (40.0 mg, 0.135 mmol, 1.0 equiv.) and 3-benzoylacrylic acid (28.6 mg, 0.163 mmol, 1.2 equiv.) were used in a similar manner to synthesis step III of Example 1 to afford compound 8bk as an orange yellow solid (23.2 mg, 0.0514 mmol, 38%). NMR data for compound 8bk are given as follow:

¹H NMR (600 MHz, CDCl₃) δ 7.89 (dd, J=8.1 Hz and J=1.5 Hz, 2H), 7.65 (tt, J=7.5 Hz and J=1.2 Hz, 1H), 7.55-7.52 (m, 4H), 7.34 (d, J=4.8 Hz, 4H), 6.92 (quin, J=4.2

Hz, 1H), 7.11 (s, 1H), 6.93-6.91 (m, 3H), 5.54 (s, 2H), 3.83 (s, 3H); $^{13}$CNMR (150 MHz, CDCl$_3$) δ 194.7, 162.4, 160.7, 151.8, 145.8, 139.9, 135.94, 135.9, 133.6, 130.1, 129.0, 128.8, 127.9, 127.7, 127.2, 126.0, 120.1, 115.0, 114.7, 110.6, 55.5, 48.7; LRMS (APCI): m/z calcd for C$_{28}$H$_{22}$NO$_3$S [M+H]$^+$ 452.13, found 452.19.

<2-68> Synthesis of Methyl 4-methyl-5-oxo-2-(4-phenoxyphenyl)-4,5-dihydrothieno[3,2-b]pyridine-7-carboxylate (8ca)

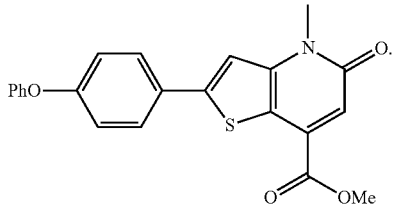 [SMILES: COC(=O)c1cc(=O)n(C)c2cc(-c3ccc(Oc4ccccc4)cc3)sc12]

Methyl 4-methyl-5-oxo-2-(4-phenoxyphenyl)-4,5-dihydrothieno[3,2-b] pyridine-7-carboxylate (8ca)

Compound 6ca (24.2 mg, 0.0615 mmol, 1.0 equiv.) was used in a similar manner to synthesis step IV of Example 1 to afford compound 8ca as a yellow solid (15.0 mg, 0.0383 mmol, 63%). NMR data for compound 8ca are given as follow:
$^1$H NMR (600 MHz, CDCl$_3$) δ 7.67 (dd, J=8.4 Hz and J=3.0 Hz, 2H), 7.39 (t, J=8.1 Hz, 2H), 7.21-7.16 (m, 3H), 7.08-7.05 (m, 4H), 4.01 (s, 3H), 3.78 (s, 3H); $^{13}$CNMR (150 MHz, CDCl$_3$) δ 165.1, 162.4, 158.9, 156.4, 150.9, 145.9, 134.1, 130.1, 128.2, 127.9, 124.2, 119.7, 119.0, 118.6, 115.4, 110.7, 53.3, 32.4; LRMS (APCI): m/z calcd for C$_{22}$H$_{18}$NO$_4$S [M+H]$^+$ 392.10, found 392.05.

<2-69> Synthesis of Methyl 2-(benzo[d][1,3]dioxol-5-yl)-4-methyl-5-oxo-4,5-dihydrothieno[3,2-b]pyridine-7-carboxylate (8da)

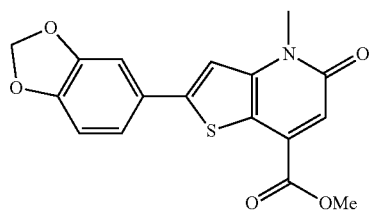 [SMILES: COC(=O)c1cc(=O)n(C)c2cc(-c3ccc4c(c3)OCO4)sc12]

Methyl 2-(benzo[d][1,3]dioxol-5-yl)-4-methyl-5-oxo-4,5-dihydrothieno[3,2-b]pyridine-7-carboxylate (8da)

Compound 6da (32.8 mg, 0.0950 mmol, 1.0 equiv.) was used in a similar manner to synthesis step IV of Example 1 to afford compound 8da as a yellow solid (13.0 mg, 0.0379 mmol, 40%). NMR data for compound 8da are given as follow:
$^1$H NMR (600 MHz, CDCl$_3$) δ 7.22 (dd, J=7.8 Hz and J=1.8 Hz, 1H), 7.20 (s, 1H), 7.16 (d, J=1.8 Hz, 1H), 7.13 (s, 1H), 6.87 (d, J=7.8 Hz, 1H), 6.04 (s, 2H), 4.01 (s, 3H), 3.77 (s, 3H); $^{13}$CNMR (150 MHz, CDCl$_3$) δ 165.1, 162.4, 151.3, 148.9, 148.6, 145.8, 134.0, 127.6, 120.6, 118.5, 115.1, 110.6, 109.1, 106.7, 101.8, 53.3, 32.3; LRMS (APCI): m/z calcd for C$_{17}$H$_{14}$NO$_5$S [M+H]$^+$ 344.06, found 343.88.

<2-70> Synthesis of Methyl 2-(2,3-dihydrobenzo[b][1,4]dioxin-6-yl)-4-methyl-5-oxo-4,5-dihydrothieno[3,2-b]pyridine-7-carboxylate (8ea)

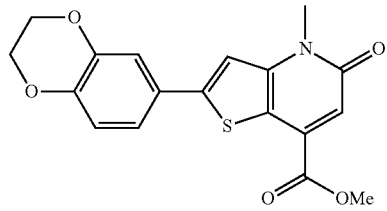 [SMILES: COC(=O)c1cc(=O)n(C)c2cc(-c3ccc4c(c3)OCCO4)sc12]

Methyl 2-(2,3-dihydrobenzo[b][1,4]dioxin-6-yl)-4-methyl-5-oxo-4,5-dihydrothieno[3,2-b]pyridine-7-carboxylate (8ea)

Compound 6ea (116 mg, 0.323 mmol, 1.0 equiv.) was used in a similar manner to synthesis step IV of Example 1 to afford compound 8ea as a yellow solid (58.4 mg, 0.163 mmol, 50%). NMR data for compound 8ea are given as follow:
$^1$H NMR (600 MHz, CDCl$_3$) δ 7.17-7.13 (m, 2H), 7.22 (s, 1H), 7.07 (s, 1H), 6.68 (d, J=8.4 Hz, 1H), 4.29 (s, 4H), 3.98 (s, 3H), 3.72 (s, 3H); $^{13}$CNMR (150 MHz, CDCl$_3$) δ 165.0, 162.3, 151.0, 145.8, 144.9, 144.0, 133.8, 126.8, 119.6, 118.3, 118.1, 115.1, 114.9, 110.3, 64.6, 64.5, 53.2, 32.2; LRMS (APCI): m/z calcd for C$_{18}$H$_{16}$NO$_5$S [M+H]$^+$ 358.07, found 357.93.

<2-71> Synthesis of Methyl 4-methyl-5-oxo-2-(3,4,5-trimethoxyphenyl)-4,5-dihydrothieno[3,2-b]pyridine-7-carboxylate (8fa)

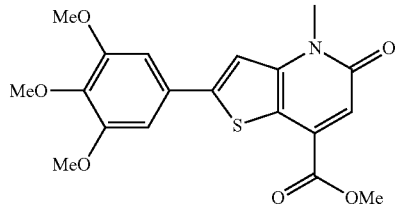 [SMILES: COC(=O)c1cc(=O)n(C)c2cc(-c3cc(OC)c(OC)c(OC)c3)sc12]

Methyl 4-methyl-5-oxo-2-(3,4,5-trimethoxyphenyl)-4,5-dihydrothieno[3,2-b]pyridine-7-carboxylate (8fa)

Compound 6fa (52.0 mg, 0.133 mmol, 1.0 equiv.) was used in a similar manner to synthesis step IV of Example 1 to afford compound 8fa as a yellow solid (13.3 mg, 0.0342 mmol, 26%). NMR data for compound 8fa are given as follow:
$^1$H NMR (600 MHz, CDCl$_3$) δ 7.21 (s, 1H), 7.18 (s, 1H), 6.89 (s, 2H), 4.01 (s, 3H), 3.95 (s, 6H), 3.90 (s, 3H), 3.80 (s, 3H); $^{13}$CNMR (150 MHz, CDCl$_3$) δ 165.2, 162.4, 153.9, 151.4, 145.7, 139.5, 133.9, 129.0, 118.8, 115.4, 111.1, 103.8, 61.2, 56.5, 53.3, 32.4; LRMS (APCI) m/z calcd for C$_{19}$H$_{20}$NO$_6$S [M+H]$^+$ 390.10, found 389.92.

<2-72> Synthesis of Methyl 2-(4-(dimethylamino)phenyl)-4-methyl-5-oxo-4,5-dihydrothieno[3,2-b]pyridine-7-carboxylate (8ga)

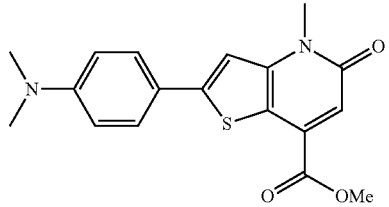 [SMILES: COC(=O)c1cc(=O)n(C)c2cc(-c3ccc(N(C)C)cc3)sc12]

Methyl 2-(4-(dimethylamino)phenyl)-4-methyl-5-oxo-4,5-dihydrothieno[3,2-b]pyridine-7-carboxylate (8ga)

Compound 6ga (60.0 mg, 0.174 mmol, 1.0 equiv.) was used in a similar manner to synthesis step IV of Example 1 to afford compound 8ga as an orange-red solid (19.6 mg, 0.0572 mmol, 33%). NMR data for compound 8ga are given as follow:

$^1$H NMR (600 MHz, CDCl$_3$) δ 7.60 (d, J=8.4 Hz, 2H), 7.14 (s, 1H), 7.10 (s, 1H), 6.73 (d, J=8.4 Hz, 2H), 4.00 (s, 3H), 3.77 (s, 3H), 3.04 (s, 6H); $^{13}$CNMR (150 MHz, CDCl$_3$) δ 165.4, 162.5, 152.6, 151.2, 146.4, 133.9, 127.3, 121.1, 117.2, 114.2, 112.3, 108.5, 53.2, 40.4, 32.3; LRMS (APCI): m/z calcd for C$_{18}$H$_{19}$N$_2$O$_3$S [M+H]$^+$ 343.11, found 342.84.

<2-73> Synthesis of Methyl 2-(3-(dimethylamino)phenyl)-4-methyl-5-oxo-4,5-dihydrothieno[3,2-b]pyridine-7-carboxylate (8gb)

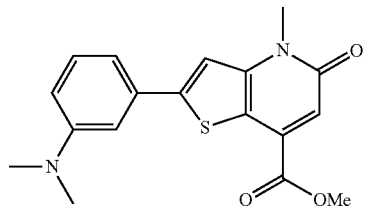 [SMILES: COC(=O)c1cc(=O)n(C)c2cc(-c3cccc(N(C)C)c3)sc12]

Methyl 2-(3-(dimethylamino)phenyl)-4-methyl-5-oxo-4,5-dihydrothieno[3,2-b]pyridine-7-carboxylate (8gb)

Compound 6gb (81.2 mg, 0.236 mmol, 1.0 equiv.) was used in a similar manner to synthesis step IV of Example 1 to afford compound 8gb as a yellow solid (22.0 mg, 0.0642 mmol, 27%). NMR data for compound 8gb are given as follow:

$^1$H NMR (600 MHz, CDCl$_3$) δ 7.29-7.26 (m, 1H), 7.19 (s, 1H), 7.16 (s, 1H), 7.02 (d, J=7.2 Hz, 1H), 6.94 (s, 1H), 6.74 (d, J=8.4 Hz, 1H), 3.99 (s, 3H), 3.75 (s, 3H), 3.01 (s, 6H); $^{13}$CNMR (150 MHz, CDCl$_3$) δ 165.1, 162.3, 152.4, 151.0, 145.7, 134.0, 133.9, 129.9, 118.5, 115.3, 114.5, 113.5, 111.0, 109.8, 53.2, 40.6, 32.3; LRMS (APCI): m/z calcd for C$_{18}$H$_{19}$N$_2$O$_3$S [M+H]$^+$ 343.11, found 342.94.

<2-74> Synthesis of Methyl 2-(2-(dimethylamino)phenyl)-4-methyl-5-oxo-4,5-dihydrothieno[3,2-b]pyridine-7-carboxylate (8gc)

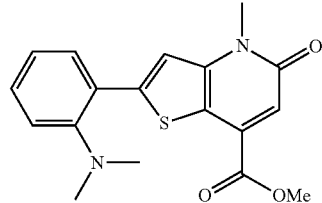 [SMILES: COC(=O)c1cc(=O)n(C)c2cc(-c3ccccc3N(C)C)sc12]

Methyl 2-(2-(dimethylamino)phenyl)-4-methyl-5-oxo-4,5-dihydrothieno[3,2-b]pyridine-7-carboxylate (8gc)

Compound 6gc (88.0 mg, 0.255 mmol, 1.0 equiv.) was used in a similar manner to synthesis step IV of Example 1 to afford compound 8gc as a yellow solid (28.3 mg, 0.0826 mmol, 32%). NMR data for compound 8gc are given as follow:

$^1$H NMR (600 MHz, CDCl$_3$) δ 7.60 (d, J=7.8 Hz, 1H), 7.41 (s, 1H), 7.32 (t, J=7.8 Hz, 1H), 7.21-7.20 (m, 2H), 7.11 (t, J=7.8 Hz, 1H), 4.00 (s, 3H), 3.78 (s, 3H), 2.69 (s, 6H); $^{13}$CNMR (150 MHz, CDCl$_3$) δ 165.3, 162.4, 151.9, 149.6, 145.0, 134.3, 129.9, 129.6, 127.9, 123.5, 120.4, 118.6, 117.2, 112.8, 53.1, 44.4, 32.2; LRMS (APCI): m/z calcd for C$_{18}$H$_{19}$N$_2$O$_3$S [M+H]$^+$ 343.11, found 342.88.

<2-75> Synthesis of Methyl 4-benzyl-2-(4-(dimethylamino)phenyl)-5-oxo-4,5-dihydrothieno[3,2-b]pyridine-7-carboxylate (8gd)

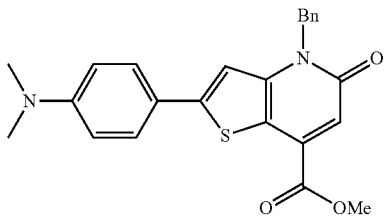 [SMILES: COC(=O)c1cc(=O)n(Cc2ccccc2)c2cc(-c3ccc(N(C)C)cc3)sc12]

Methyl 4-benzyl-2-(4-(dimethylamino)phenyl)-5-oxo-4,5-dihydrothieno[3,2-b]pyridine-7-carboxylate (8gd)

Compound 6gd (50.0 mg, 0.119 mmol, 1.0 equiv.) was used in a similar manner to synthesis step III of Example 1 to afford compound 8gd as a red solid (18.4 mg, 0.0440 mmol, 37%). NMR data for compound 8gd are given as follow:

$^1$H NMR (600 MHz, CDCl$_3$) δ 7.48 (d, J=9.0 Hz, 2H), 7.32-7.28 (m, 4H), 7.26-7.25 (m, 1H), 7.21 (s, 1H), 7.00 (s, 1H), 6.69 (d, J=8.4 Hz, 2H), 5.50 (s, 2H), 4.01 (s, 3H), 3.01 (s, 6H); $^{13}$CNMR (150 MHz, CDCl$_3$) δ 165.3, 162.5, 152.5, 151.0, 146.0, 136.0, 134.3, 129.0, 127.8, 127.3, 127.2, 117.3, 114.6, 112.3, 109.1, 53.2, 48.6, 40.4; LRMS (APCI): m/z calcd for C$_{24}$H$_{23}$N$_2$O$_3$S [M+H]$^+$ 419.14, found 419.09.

<2-76> Synthesis of 7-Acetyl-2-(4-(dimethylamino)phenyl)-4-methylthieno[3,2-b]pyridine-5(4H)-one (8ge)

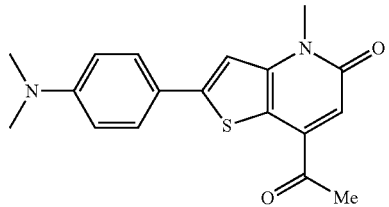 [SMILES: CC(=O)c1cc(=O)n(C)c2cc(-c3ccc(N(C)C)cc3)sc12]

7-Acetyl-2-(4-(dimethylamino)phenyl)-4-methylthieno[3,2-b]pyridine-5(4H)-one (8ge)

Compound 5ga (31.0 mg, 0.133 mmol, 1.0 equiv.) and (E)-4-oxopent-2-enoic acid (28.1 mg, 0.160 mmol, 1.2 equiv.) were used in a similar manner to synthesis step III of Example 1 to afford compound 8ge as a red solid (15.0 mg, 0.0460 mmol, 35%). NMR data for compound 8ge are given as follow:

$^1$H NMR (600 MHz, CDCl$_3$) δ 7.60 (d, J=8.4 Hz, 2H), 7.08 (s, 1H), 7.03 (s, 1H), 6.73 (d, J=8.4 Hz, 2H), 3.78 (s, 3H), 3.03 (s, 6H), 2.64 (s, 3H); $^{13}$CNMR (150 MHz, CDCl$_3$) δ 198.0, 163.1, 154.0, 151.1, 146.5, 139.0, 127.3, 121.3, 117.4, 112.4, 108.0, 40.4, 32.4, 26.4; LRMS (APCI): m/z calcd for C$_{18}$H$_{19}$N$_2$O$_2$S [M+H]$^+$ 327.12, found 327.00.

<2-77> Synthesis of 7-Benzoyl-4-benzyl-2-(4-(dimethylamino)phenyl)thieno[3,2-b]pyridine-5(4H)-one (8gf)

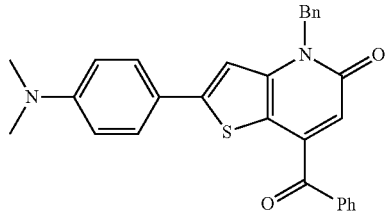 [SMILES: CN(C)c1ccc(-c2cc3c(s2)c(C(=O)c2ccccc2)cc(=O)n3Cc2ccccc2)cc1]

7-Benzoyl-4-benzyl-2-(4-(dimethylamino)phenyl)thieno[3,2-b]pyridine-5(4H)-one (8gf)

Compound 5gd (40.0 mg, 0.130 mmol, 1.0 equiv.) and 3-benzoylacrylic acid (27.4 mg, 0.156 mmol, 1.2 equiv.) were used in a similar manner to synthesis step III of Example 1 to afford compound 8gf as a red solid (25.0 mg, 0.0538 mmol, 41%). NMR data for compound 8gf are given as follow:

$^1$H NMR (600 MHz, CDCl$_3$) δ 7.91 (dd, J=8.4 Hz and J=1.8 Hz, 2H), 7.64 (tt, J=7.5 Hz and J=1.3 Hz, 1H), 7.54-7.49 (m, 4H), 7.35-7.33 (m, 4H), 7.27-7.26 (m, 1H), 7.05 (s, 1H), 6.85 (s, 1H), 6.69 (d, J=9.0 Hz, 2H), 5.54 (s, 2H), 3.01 (s, 6H); $^{13}$CNMR (150 MHz, CDCl$_3$) δ 194.9, 165.5, 153.0, 151.1, 146.2, 139.9, 136.1, 136.0, 133.6, 130.1, 129.0, 128.8, 127.8, 127.3, 127.2, 121.1, 119.1, 114.3, 112.3, 109.0, 48.7, 40.4; LRMS (APCI): m/z calcd for C$_{29}$H$_{25}$N$_2$O$_2$S [M+H]$^+$ 465.16, found 465.18.

<2-78> Synthesis of Methyl 2-(4-(diethylamino)phenyl)-4-methyl-5-oxo-4,5-dihydrothieno[3,2-b]pyridine-7-carboxylate (8ha)

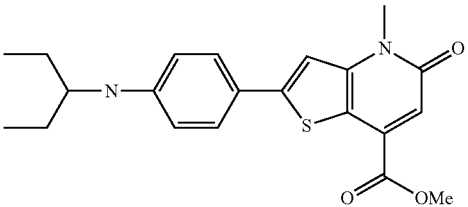 [SMILES: CCC(CC)Nc1ccc(-c2cc3c(s2)c(C(=O)OC)cc(=O)n3C)cc1]

Methyl 2-(4-(diethylamino)phenyl)-4-methyl-5-oxo-4,5-dihydrothieno[3,2-b]pyridine-7-carboxylate (8ha)

Compound 6ha (55.8 mg, 0.150 mmol, 1.0 equiv.) was used in a similar manner to synthesis step IV of Example 1 to afford compound 8ha as an orange yellow solid (29.4 mg, 0.0794 mmol, 53%). NMR data for compound 8ha are given as follow:

$^1$H NMR (600 MHz, CDCl$_3$) δ 7.53 (d, J=9.0 Hz, 2H), 7.08 (s, 1H), 7.02 (s, 1H), 6.66 (d, J=8.4 Hz, 2H), 3.97 (s, 3H), 3.72 (s, 3H), 3.40 (q, J=7.2 Hz, 4H), 1.20 (t, J=7.2 Hz, 6H); $^{13}$CNMR (150 MHz, CDCl$_3$) δ 165.3, 162.5, 151.7, 148.6, 146.4, 133.8, 127.5, 120.0, 116.8, 114.0, 111.6, 108.0, 53.1, 44.5, 32.2, 12.7; LRMS (APCI): m/z calcd for C$_{20}$H$_{23}$N$_2$O$_3$S [M+H]$^+$ 371.14, found 371.02.

<2-79> Synthesis of Methyl 4-methyl-2-(4-(4-methylpiperazin-1-yl)phenyl)-5-oxo-4,5-dihydrothieno[3,2-b]pyridine-7-carboxylate (8ia)

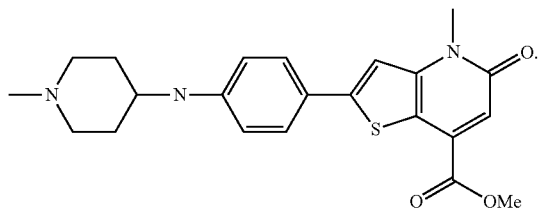 [SMILES: COC(=O)c1cc(=O)n(C)c2cc(-c3ccc(NC4CCN(C)CC4)cc3)sc12]

Methyl 4-methyl-2-(4-(4-methylpiperazin-1-yl)phenyl)-5-oxo-4,5-dihydrothieno[3,2-b]pyridine-7-carboxylate (8ia)

Compound 6ia (24.6 mg, 0.0616 mmol, 1.0 equiv.) was used in a similar manner to synthesis step IV of Example 1 to afford compound 8ia as a dark red solid (10.0 mg, 0.0252 mmol, 41%). NMR data for compound 8ia are given as follow:

$^1$H NMR (600 MHz, CDCl$_3$) δ 7.60 (d, J=10.2 Hz, 2H), 7.15 (s, 1H), 7.12 (s, 1H), 6.93 (d, J=10.8 Hz, 2H), 3.99 (s, 3H), 3.76 (s, 3H), 3.32 (t, J=5.7 Hz, 4H), 2.62 (t, J=5.7 Hz, 4H), 2.38 (s, 3H); $^{13}$CNMR (150 MHz, CDCl$_3$) δ 165.3, 162.5, 151.9, 151.8, 146.2, 133.9, 127.3, 124.0, 117.8, 115.6, 114.6, 109.4, 54.9, 53.2, 48.1, 46.2, 32.3; LRMS (APCI): m/z calcd for C$_{21}$H$_{24}$N$_3$O$_3$S [M+H]$^+$ 398.15, found 397.94.

<2-80> Synthesis of Methyl 4-methyl-5-oxo-2-(2,3,6,7-tetrahydro-1H,5H-pyrido[3,2,1-ij]quinolin-9-yl)-4,5-dihydrothieno[3,2-b]pyridine-7-carboxylate (8ja)

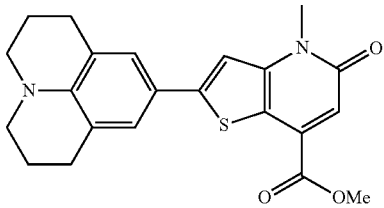 [SMILES: COC(=O)c1cc(=O)n(C)c2cc(-c3cc4c5c(c3)CCCN5CCC4)sc12]

Methyl 4-methyl-5-oxo-2-(2,3,6,7-tetrahydro-1H,5H-pyrido[3,2,1-ij]quinolin-9-yl)-4,5-dihydrothieno[3,2-b]pyridine-7-carboxylate (8ja)

Compound 6ja (50.0 mg, 0.126 mmol, 1.0 equiv.) was used in a similar manner to synthesis step IV of Example 1 to afford compound 8ja as an orange yellow solid (18.0 mg, 0.0456 mmol, 36%). NMR data for compound 8ja are given as follow:

$^1$H NMR (600 MHz, CDCl$_3$) δ 7.16 (s, 2H), 7.10 (s, 1H), 7.03 (s, 1H), 3.99 (s, 3H), 3.76 (s, 3H), 3.24-3.22 (m, 4H), 2.89 (t, J=6.6 Hz, 4H), 2.10-2.08 (m, 4H); $^{13}$CNMR (150 MHz, CDCl$_3$) δ 165.4, 162.6, 153.2, 146.5, 144.2, 133.9, 125.0, 121.6, 120.0, 116.6, 114.0, 107.8, 53.1, 50.0, 32.3, 27.9, 21.8; LRMS (APCI): m/z calcd for C$_{22}$H$_{23}$N$_2$O$_3$S [M+H]$^+$ 395.14, found 395.20.

<2-81> Synthesis of 7-Benzoyl-2-(4-(diphenylamino)phenyl)-4-methylthieno[3,2-b]pyridine-5(4H)-one (8ka)

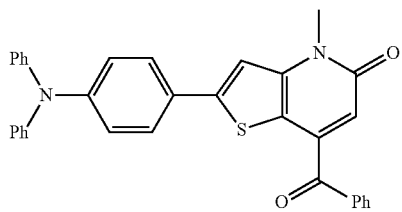 [SMILES: Cn1c(=O)cc(C(=O)c2ccccc2)c2sc(-c3ccc(N(c4ccccc4)c4ccccc4)cc3)cc21]

7-Benzoyl-2-(4-(diphenylamino)phenyl)-4-methylthieno[3,2-b]pyridine-5(4H)-one (8ka)

Compound 5ka (40.0 mg, 0.112 mmol, 1.0 equiv.) and 3-benzoylacrylic acid (23.7 mg, 0.134 mmol, 1.2 equiv.) were used in a similar manner to synthesis step III of Example 1 to afford compound 8ka as a red solid (26.9 mg, 0.0525 mmol, 47%). NMR data for compound 8ka are given as follow:

$^1$H NMR (600 MHz, CDCl$_3$) δ 7.86 (dd, J=8.4 Hz and J=0.6 Hz, 2H), 7.65-7.27 (m, 1H), 7.56 (dd, J=6.6 Hz and J=2.4 Hz, 2H), 7.52 (t, J=7.8 Hz, 2H), 7.31-7.29 (m, 4H), 7.20 (s, 1H), 7.16-7.14 (m, 4H), 7.11-7.07 (m, 4H), 6.85 (s, 1H), 3.81 (s, 3H); $^{13}$CNMR (150 MHz, CDCl$_3$) δ 194.7, 162.4, 152.2, 149.3, 147.1, 146.3, 139.6, 136.0, 133.6, 130.1, 129.6, 129.0, 128.8, 127.2, 126.4, 125.3, 124.0, 122.5, 119.5, 115.1, 109.8, 32.5; LRMS (APCI): m/z calcd for C$_{33}$H$_{25}$N$_2$O$_2$S [M+H]$^+$ 513.16, found 513.17.

<2-82> Synthesis of 7-Benzoyl-4-methyl-2-(4-(trifluoromethoxy)phenyl)thieno[3,2-b]pyridine-5(4H)-one (81a)

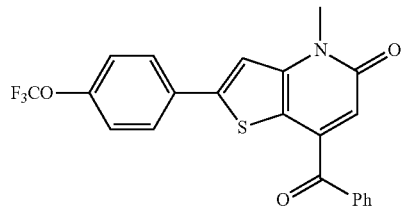

7-Benzoyl-4-methyl-2-(4-(trifluoromethoxy)phenyl)thieno[3,2-b]pyridine-5(4H)-one (81a)

Compound 51a (40.0 mg, 0.146 mmol, 1.0 equiv.) and 3-benzoylacrylic acid (30.9 mg, 0.175 mmol, 1.2 equiv.) were used in a similar manner to synthesis step III of Example 1 to afford compound 81a as a green solid (22.0 mg, 0.0512 mmol, 35%). NMR data for compound 81a are given as follow:

$^1$H NMR (600 MHz, CDCl$_3$) δ 7.83 (dd, J=7.2 Hz and J=1.2 Hz, 2H), 7.72 (dd, J=8.7 Hz and J=0.9 Hz, 2H), 7.63 (td, J=7.8 Hz and J=1.2 Hz, 1H), 7.50 (t, J=7.5 Hz, 2H), 7.27 (d, J=8.4 Hz, 2H), 7.23 (s, 1H), 6.89 (s, 1H), 3.80 (s, 3H); $^{13}$CNMR (150 MHz, CDCl$_3$) δ 194.6, 162.4, 150.0, 145.9, 139.4, 135.9, 133.7, 132.1, 130.1, 129.5, 128.9, 127.9, 127.4, 121.8, 121.4, 121.7, 119.7, 115.7, 111.7, 32.4, 29.9; $^{19}$F NMR (600 MHz, CDCl$_3$) δ −57.8; LRMS (APCI): m/z calcd for C$_{22}$H$_{15}$F$_3$NO$_3$S [M+H]$^+$ 430.07, found 430.01.

<2-83> Synthesis of 7-Benzoyl-4-methyl-2-(4-(trifluoromethyl)phenyl)thieno[3,2-b]pyridine-5(4H)-one (8ma)

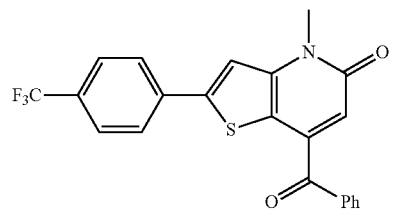

7-Benzoyl-4-methyl-2-(4-(trifluoromethyl)phenyl)thieno[3,2-b]pyridine-5(4H)-one (8ma)

Compound 5ma (40.0 mg, 0.155 mmol, 1.0 equiv.) and 3-benzoylacrylic acid (32.8 mg, 0.186 mmol, 1.2 equiv.) was used in a similar manner to synthesis step III of Example 1 to afford compound 8ma as a green solid (18.8 mg, 0.0455 mmol, 29%). NMR data for compound 8ma are given as follow:

$^1$H NMR (600 MHz, CDCl$_3$) δ 7.85 (dd, J=20.1 Hz and J=7.5 Hz, 4H), 7.72 (d, J=8.4 Hz, 2H), 7.67 (t, J=7.2 Hz, 1H), 7.54 (t, J=7.8 Hz, 2H), 7.38 (s, 1H), 6.94 (s, 1H), 3.85 (s, 3H); $^{13}$CNMR (150 MHz, CDCl$_3$) δ 194.6, 162.3, 149.5, 145.8, 139.4, 136.8, 135.9, 133.8, 131.5, 131.3, 131.1, 130.9, 130.1, 128.9, 126.6, 126.44, 126.41, 126.39, 126.36, 124.9, 123.1, 121.8, 116.1, 112.4, 32.4, 29.9; $^{19}$F NMR (600 MHz, CDCl$_3$) δ −62.8; LRMS (APCI): m/z calcd for C$_{22}$H$_{15}$F$_3$NO$_2$S [M+H]$^+$ 414.08, found 413.85.

<2-84> Synthesis of 4-Benzyl-2-(4-methoxyphenyl)-5-oxo-4,5-dihydrothieno[3,2-b]pyridine-7-carboxylic acid (9a))

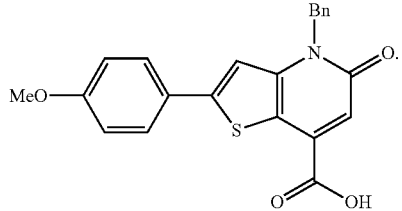 [SMILES: COc1ccc(-c2cc3c(s2)c(C(=O)O)cc(=O)n3Cc2ccccc2)cc1]

4-Benzyl-2-(4-methoxyphenyl)-5-oxo-4,5-dihydrothieno[3,2-b]pyridine-7-carboxylic acid (9a)

To a solution of compound 8be (26.2 mg, 0.0646 mmol, 1.0 equiv) in ethanol (2 mL) was added 1N KOH (0.32 mL). The mixture was heated at 70° C. for 1 hour. After completion of the reaction, the solvent was evaporated. The residue was acidified by 1N HCl (2 mL). The crude produce was extracted three times with ethyl acetate (3 mL), dried over Na$_2$SO$_4$, filtered, and evaporated in a vacuum to afford compound 9a as a yellow solid (19.8 mg, 0.0506 mmol, 78%).

NMR data for compound 9a are given as follow:
$^1$H NMR (600 MHz, DMSO-d$_6$) δ 7.71 (d, J=9.0 Hz, 2H), 7.68 (s, 1H), 7.33-7.30 (m, 4H), 7.26-7.23 (m, 1H), 7.02 (d, J=9.0 Hz, 2H), 6.95 (s, 1H), 5.51 (s, 2H), 3.80 (3H); $^{13}$CNMR (150 MHz, DMSO) δ 165.5, 161.3, 160.2, 149.7, 145.6, 136.7, 135.5, 128.6, 127.34, 127.30, 127.2, 125.3, 117.2, 114.7, 113.9, 111.7, 55.4, 47.4; LRMS (APCI): m/z calcd for C$_{22}$H$_{18}$NO$_4$S [M+H]$^+$ 392.10, found 391.95.

<2-85> Synthesis of 2-(4-(Diethylamino)phenyl)-4-methyl-5-oxo-4,5-dihydrothieno[3,2-b]pyridine-7-carboxylic acid (9b)

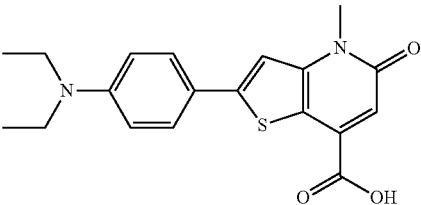 [SMILES: CCN(CC)c1ccc(-c2cc3c(s2)c(C(=O)O)cc(=O)n3C)cc1]

2-(4-(Diethylamino)phenyl)-4-methyl-5-oxo-4,5-dihydrothieno[3,2-b]pyridine-7-carboxylic acid (9b)

To a solution of compound 8ha (22.4 mg, 0.0605 mmol, 1.0 equiv) in ethanol (2.0 mL) was added 1N KOH (0.3 mL). The mixed was heated at 70° C. for 1 hour. After completion of the reaction, the solvent was evaporated and the residue was acidified by 1N HCl (2 mL). The crude produce was extracted five times with ethyl acetate (3 mL), dried over Na$_2$SO$_4$, filtered, and evaporated in a vacuum to afford compound 9b as an orange yellow solid (13.8 mg, 0.0387 mmol, 64%).

NMR data for compound 9b are given as follow:
$^1$H NMR (500 MHz, DMSO-d$_6$) δ 7.63 (d, J=8.5 Hz, 2H), 7.56 (s, 1H), 6.79 (s, 1H), 6.73 (d, J=9.0 Hz, 2H), 3.67 (s, 3H), 3.42-3.37 (m, 4H), 1.19 (t, J=7.0 Hz, 6H); $^{13}$CNMR (150 MHz, DMSO-d$_6$) δ 165.7, 161.3, 151.2, 148.2, 146.5, 127.2, 119.4, 115.5, 112.4, 111.4, 109.4, 43.7, 32.0, 12.5; LRMS (APCI): m/z calcd for C$_{19}$H$_{19}$N$_2$O$_3$S [M−H]$^−$ 355.11, found 355.33.

Example 3

Analysis of Fluoresence Property of Novel Derivative Compounds

Photophysical analysis results of the novel derivative compounds synthesized in Example 2 are summarized in Table 1, below.

TABLE 1

| | in dichloromethane (10 μM) | | | | | | in acetonitrile (10 μM) | | | | | |
| --- | --- | --- | --- | --- | --- | --- | --- | --- | --- | --- | --- | --- |
| entry | $\lambda_{abs}$ | $\lambda_{em}$ | ε | $\Phi_F$ | brightness | Stoke's shift | $\lambda_{abs}$ | $\lambda_{em}$ | ε | $\Phi_F$ | brightness | Stoke's shift |
| 8aa | 394 | 462 | 7,600 | 0.63 | 4,800 | 68 | 392 | 462 | 17,600 | 0.46 | 8,100 | 70 |
| 8ba | 400 | 472 | 16,000 | 0.9 | 14,400 | 72 | 396 | 474 | 10,400 | 0.77 | 8,000 | 78 |
| 8bb | 394 | 464 | 46,000 | 0.48 | 22,100 | 70 | 394 | 463 | 35,100 | 0.32 | 11,200 | 69 |
| 8bc | 398 | 469 | 21,000 | 0.51 | 10,700 | 71 | 396 | 468 | 15,100 | 0.31 | 4,700 | 72 |
| 8bd | 408 | 477 | 34,000 | 1.8 | 61,000 | 69 | 408 | 477 | 11,000 | 0.1 | 1,100 | 69 |
| 8be | 404 | 474 | 40,000 | 0.99 | 39,600 | 70 | 400 | 477 | 23,600 | 0.9 | 21,200 | 77 |
| 8bf | 378 | 426 | 29,000 | 0.83 | 24,000 | 48 | 376 | 424 | 26,000 | 0.42 | 10,900 | 48 |
| 8bg | 376 | 427 | 39,000 | 0.4 | 16,000 | 51 | 374 | 425 | 37,000 | 0.98 | 36,300 | 51 |
| 8bh | 386 | 437 | 28,000 | 0.46 | 13,000 | 51 | 384 | 435 | 30,000 | 0.42 | 12,600 | 51 |
| 8bi | 418 | 510 | 13,300 | 0.98 | 13,000 | 92 | 412 | 512 | 7,300 | 0.84 | 6,100 | 100 |
| 8bj | 426 | 512 | 38,000 | 0.99 | 37,600 | 86 | 420 | 515 | 15,000 | 0.61 | 9,100 | 95 |
| 8bk | 416 | 547 | 9,400 | 0.67 | 6,300 | 131 | 406 | 558 | 19,700 | 0.48 | 9,500 | 152 |
| 8ca | 398 | 469 | 12,300 | 0.83 | 14,800 | 71 | 396 | 469 | 31,500 | 0.63 | 19,800 | 73 |
| 8da | 404 | 474 | 4,400 | 0.62 | 2,700 | 70 | 400 | 482 | 36,300 | 0.44 | 16,000 | 82 |

TABLE 1-continued

| | in dichloromethane (10 μM) | | | | | | in acetonitrile (10 μM) | | | | | |
|---|---|---|---|---|---|---|---|---|---|---|---|---|
| entry | $\lambda_{abs}$ | $\lambda_{em}$ | ε | $\Phi_F$ | brightness | Stoke's shift | $\lambda_{abs}$ | $\lambda_{em}$ | ε | $\Phi_F$ | brightness | Stoke's shift |
| 8ea | 402 | 473 | 28,600 | 0.83 | 23,700 | 71 | 398 | 478 | 18,800 | 0.68 | 12,800 | 80 |
| 8fa | 400 | 485 | 24,700 | 0.53 | 13,100 | 85 | 398 | 495 | 11,300 | 0.38 | 4,300 | 97 |
| 8ga | 434 | 554 | 29,100 | 0.82 | 23,900 | 120 | 428 | 599 | 22,800 | 0.08 | 1,800 | 171 |
| 8gb | 396 | 560 | 11,800 | 0.01 | 100 | 164 | 396 | 460 | 3,300 | 0.03 | 100 | 64 |
| 8gc | 406 | 537 | 17,700 | 0.17 | 3,000 | 131 | 402 | 484 | 27,400 | n.d. | n.d. | 82 |
| 8gd | 436 | 563 | 21,800 | 0.98 | 21,400 | 127 | 330, 432 | 488, 610 | 40,300 | 0.05 | 2,000 | 178 |
| 8ge | 448 | 610 | 27,200 | 0.18 | 4,900 | 162 | 440 | 504 | 23,800 | n.d. | n.d. | 64 |
| 8gf | 446 | 643, 681 | 35,200 | 0.01 | 400 | 232 | 438 | 521 | 11,100 | n.d. | n.d. | 83 |
| 8ha | 442 | 562 | 36,900 | 0.91 | 33,600 | 120 | 436 | 605 | 38,200 | 0.08 | 3,100 | 169 |
| 8ia | 420 | 550 | 23,900 | 0.99 | 23,700 | 130 | 418 | 587 | 27,800 | 0.03 | 800 | 169 |
| 8ja | 454 | 605 | 31,200 | 0.25 | 7,800 | 151 | 448 | 511 | 28,500 | 0.02 | 600 | 63 |
| 8ka | 438 | 635 | 34,600 | 0.05 | 1,700 | 197 | 430 | 504 | 26,600 | n.d. | n.d. | 74 |
| 8la | 400 | 518 | 9,900 | 0.85 | 8,400 | 118 | 394 | 526 | 11,000 | 0.65 | 7,200 | 132 |
| 8ma | 398 | 511 | 6,900 | 0.82 | 5,700 | 113 | 388 | 517 | 10,000 | 0.8 | 8,000 | 179 |

The analysis data exhibit that emission wavelengths of the novel derivative compound of the present disclosure are largely dependent on types of substituent groups on the thieno[3,2-b] pyridine-5(4H)-one scaffold. It is therefore noteworthy that the derivative compounds in Table 1 exhibit a wide spectrum of fluorescent emissions (λem: 427-678 nm, λem: 424-610 nm) along with large Stokes shifts (up to 232 nm in dichloromethane; up to 179 nm in acetonitrile) and high quantum yields (up to 99% in dichloromethane; up to 98% in acetonitrile). For reference, Stokes shift is the difference between the band maxima of the first absorption and fluorescent emission spectra and can provide information on an excited state. For example, when the dipole moment of a fluorescent molecule is higher the ground state, Stokes shift increases with an increase in solvent polarity. This phenomenon can be used in fluorescent polarity probing.

Compared to compound 8aa, which contains a simple phenyl group at the $C_2$ position, its electron-rich counterparts exhibited obvious bathochromic shifts (red shifts) in emission. For example, the emission maxima of the derivative compounds bearing an oxygen atom on the phenyl ring at the $C_2$ position, as in the case of 8ca, 8ba, 8ea, 8da, and 8fa, tended to gradually red-shift with an increase in electron-donating ability of the R2 group, thus emitting at different wavelengths (469, 472, 473, 474, and 485 nm, respectively), while the absorption maxima remained relatively constant (398-404 nm). In addition, a similar trend was observed in a series of nitrogen atom-containing derivative compounds such as 8ga, 8ha, 8ia, and 8ja as they fluoresced at 554, 562, 550, and 605 nm, respectively, with the absorption maxima ranging from 420 to 454 nm. As other examples, two different sets including 8ma, 8la, and 8ka in one set and 8bk and 8gf in the other set demonstrated the same trend in emission wavelengths.

Considering the regioisomeric effects of specific auxochromes such as methoxy and dimethylamino groups on the fluorescence property, a series of ortho-, meta-, and parasubstituted derivative compounds of the present disclosure (see: 8bc, 8bb, and 8ba for methoxy group; see: 8gc, 8gb, and 8ga for dimethylamino group) were prepared and compared with respect to the quantum yield and the absorption/emission maxima.

As a result, it can be concluded that the para substitution provides improved photophysical properties including a high quantum yield and significant bathochromic shift in the emission wavelengths (8ba and 8ga).

The brightness of a fluorophore is calculated by the multiplication of its molar extinction coefficient (ε) with its quantum yield (Φ). When a benzyl group was introduced at the R1 position as a replacement of a methyl group (compounds 8ba/8be and 8bi/8bj), a normally higher molar extinction coefficient (ε), and thus, a much greater brightness, was obtained with the exception of 8ga/8gd, which had a similar brightness. Particularly when R1 is H (8bd), the quantum yield became larger than 1 because a photoinduced reaction was performed by a single photon for a long period of time or because a chain reaction was performed by radiation.

Figure 3:
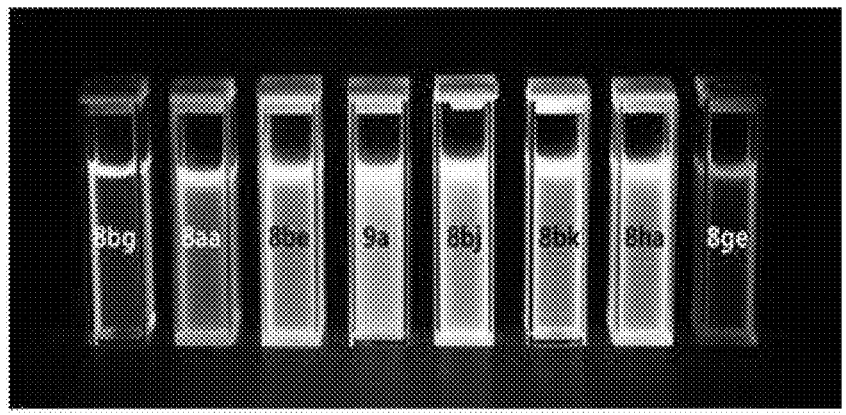
FIG. 3 is an image of derivative compounds of the present disclosure in dichloromethane, which are excited at 365 nm under a UV lamp.

With respect to the impact of the R3 substituent, an increase in electron-withdrawing ability from H (8bf) to methyl (8bg), phenyl (8bh), methyl ester (8ba), and acetyl (8bi) with larger conjugations resulted in bathochromic shifts in the emission wavelengths from 426, 427, 437, 472, and 510 nm, respectively. The same bathochromic shifts were observed in both 8ga/8ge and 8gd/8gf. Therefore, the photophysical properties of the derivative compounds of the present disclosure can be fine-tuned by a proper combination of an electrondonating R2 and an electron-withdrawing R3 substituent (See FIG. 3).

Example 4

Analysis of Solvatochromic Property of Novel Derivative Compounds

Figure 4A:
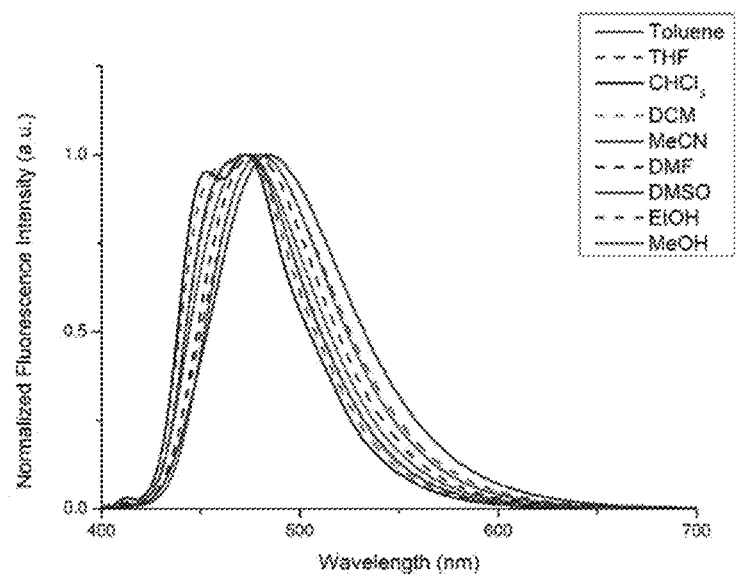
FIG. 4A to 4C shows analysis results accounting for solvatochromic properties of some of the derivative compounds of the present disclosure.
Figure 4B:
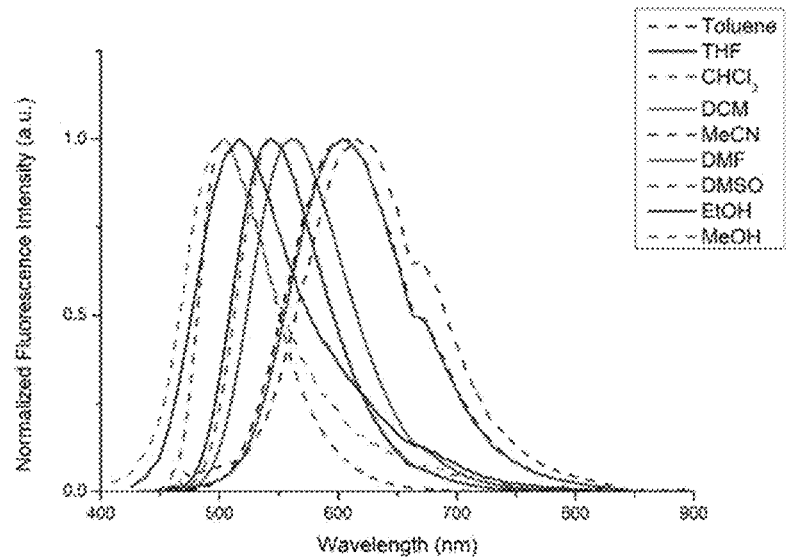
Figure 4C:
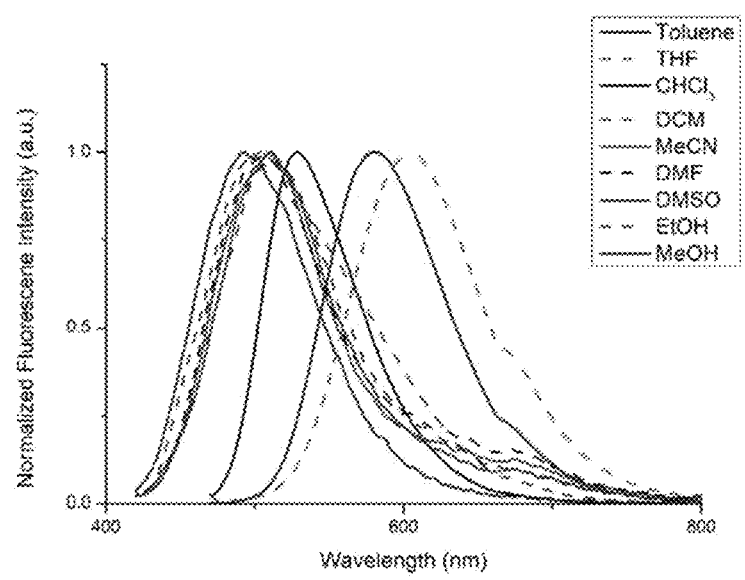

Of the novel derivative compounds synthesized in the Examples, some derivative compounds (8ba, 8ha, and 8ja) were analyzed for solvatochromic properties, and the analysis results are summarized in Table 2 and depicted in FIG. 4A to 4C.

TABLE 2

| | Name | | | | | | | | |
|---|---|---|---|---|---|---|---|---|---|
| | 8ba | | | 8ha | | | 8ja | | |
| | Structure | | | | | | | | |

| Solvent | $\lambda_{Abs}$ (nm) | $\lambda_{Em}$ (nm) | $\Phi_F$ | $\lambda_{Abs}$ (nm) | $\lambda_{Em}$ (nm) | $\Phi_F$ | $\lambda_{Abs}$ (nm) | $\lambda_{Em}$ (nm) | $\Phi_F$ |
|---|---|---|---|---|---|---|---|---|---|
| Hexane | — | — | — | — | — | — | — | — | — |
| Toluene | 402 | 473 | 0.98 | 434 | 504 | 0.98 | 442 | 529 | — |
| THF | 402 | 472 | 0.99 | 436 | 543 | 0.97 | 430 | 502 | — |
| CHCl3 | 400 | 472 | 0.95 | 442 | 545 | 0.99 | 454 | 580 | 0.48 |
| DCM | 400 | 472 | 0.9 | 442 | 562 | 0.91 | 454 | 615 | 0.25 |
| MeCN | 396 | 474 | 0.77 | 436 | 605 | 0.08 | 448 | 511 | 0.02 |
| DMF | 402 | 477 | 0.99 | 442 | 604 | 0.16 | 456 | 509 | 0.10 |
| DMSO | 404 | 480 | 0.99 | 446 | 615 | 0.1 | 460 | 508 | 0.17 |
| EtOH | 400 | 480 | 0.99 | 444 | 516 | 0.04 | 458 | 508 | 0.09 |
| MeOH | 396 | 484 | 0.99 | 444 | 503 | 0 | 456 | 493 | 0.30 |

Interestingly, 8ha showed a broad spectrum of emission wavelengths (504-615 nm) in the visible region with increase in solvent polarity (positive solvatochromism), whereas 8ba had a spectrally narrow emission window from 472 to 484 nm. This result indicates that 8ba is relatively insensitive to solvent polarity, compared to 8ha. Particularly, the julolidine derivative 8ja exhibited red shifts only in toluene, chloroform, and dichloromethane. However, its emission wavelengths were remarkably blue-shifted (hypsochromic shift) in polar solvents, suggesting that 8ja has negative solvatochromic characteristics.

Example 5

Analysis of Fluorescent Property of Novel Derivative Compound with pH Change

Figure 5:
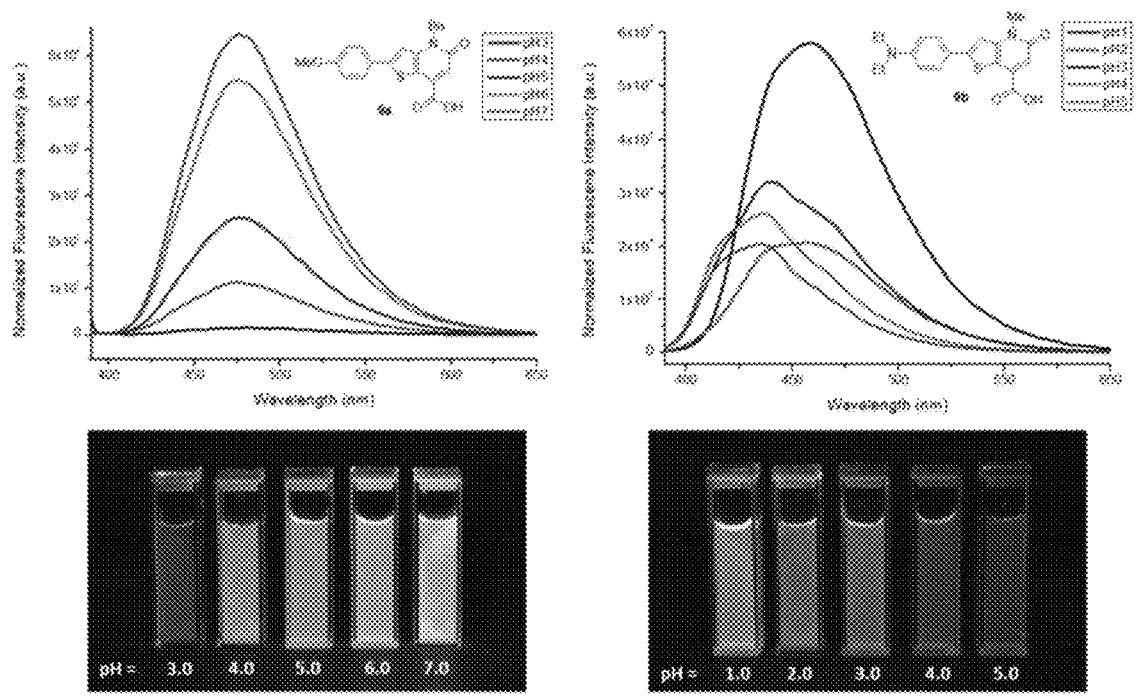
FIG. 5 shows pH-dependent fluorescence spectra of the derivative compounds of the present disclosure.

Of the compounds synthesized in the present disclosure, the carboxylic acid derivatives 9a and 9b were prepared by hydrolysis of 8ba and 8ha, respectively, and their photophysical properties were analyzed under various pH conditions (pH 1.0-7.0). The results are summarized in Table 3, below and depicted in FIG. 5.

TABLE 3

| | Name | | |
|---|---|---|---|
| | 9a | | 9b |
| | Structure | | |

| pH | $\lambda_{Ex}$ (nm) | $\lambda_{Em}$ (nm) | $\lambda_{Ex}$ (nm) | $\lambda_{Em}$ (nm) |
|---|---|---|---|---|
| pH 1 | — | — | 382 | 461 |
| pH 2 | — | — | — | — |
| pH 3 | 381 | 482 | 378 | 441 |
| pH 4 | 382 | 475 | 376 | 436 |
| pH 5 | 381 | 475 | 373 | 434 |
| pH 6 | 379 | 475 | — | — |
| pH 7 | 382 | 476 | — | — |

As a result of analysis, the derivative compound 9a bearing a p-methoxy group on the C2-phenyl ring exhibited a gradual increase in fluorescence intensity with increasing of pH, demonstrating the applicability thereof to the development of a fluorescent pH sensor for monitoring a fine change in micro environment. In contrast to 9a, 9b was observed to significantly decrease in fluorescence intensity in presponse to an increase in pH (particularly, the highest fluorescent intensity at a condition of pH 1.0). This remarkable enhancement in fluorescence intensity was supposedly attributed to the inhibition of fluorescent quenching via photoinduced electron transfer (PET) due to the protonation of the p-diethylamino group on the C2-phenyl ring.

Therefore, photophysical properties of the novel derivative compounds synthesized in the present disclosure can be readily fine-tuned by varying the electrondonating R2 and electron-withdrawing R3 substituents. Particularly, the derivative compounds exhibit a wide spectrum of fluorescent emissions (λem: 427-678 nm, λem: 424-610 nm) along with large Stokes shifts (up to 232 nm in dichloromethane; up to 179 nm in acetonitrile) and high quantum yields (up to 99% in dichloromethane; up to 98% in acetonitrile). Therefore, the novel derivative compounds of the present disclosure can find applications in physical, chemical, and biomedical studies. Particularly, compounds with emission wavelengths of interest can be selected from the pool of derivative compounds having a wide spectrum of fluorescence emissions.

Although embodiments of the present disclosure have been described herein, it should be understood that the foregoing embodiments and advantages are merely examples and are not to be construed as limiting the present disclosure or the scope of the claims. Numerous other modifications and embodiments can be devised by those skilled in the art that will fall within the spirit and scope of the principles of this disclosure, and the present teaching can also be readily applied to other types of apparatuses. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

The invention claimed is:

1. A compound selected from the group consisting of the compounds having the structural formulas 3 to 4, and 6 to 28, below:

| structure |
|---|
| 3 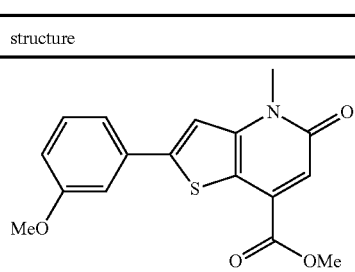 |
| 4 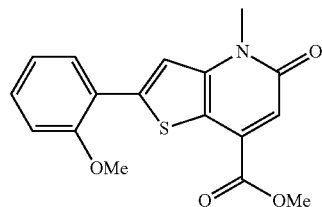 [SMILES: COC(=O)c1cc(=O)n(C)c2cc(-c3ccccc3OC)sc12] |

-continued

| structure |
|---|
| 6 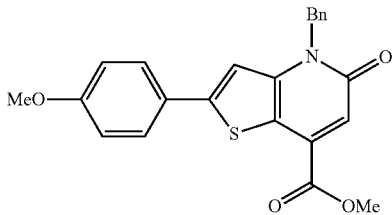 [SMILES: COC(=O)c1cc(=O)n(Cc2ccccc2)c2cc(-c3ccc(OC)cc3)sc12] |
| 7 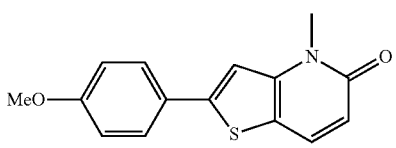 [SMILES: COc1ccc(-c2cc3c(ccc(=O)n3C)s2)cc1] |
| 8 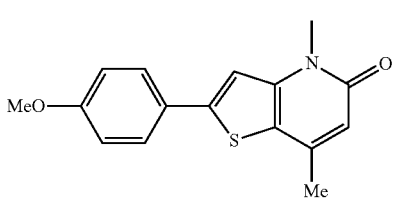 [SMILES: COc1ccc(-c2cc3c(s2)c(C)cc(=O)n3C)cc1] |
| 9 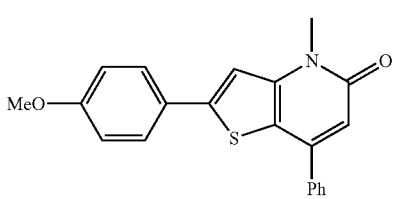 |
| 10 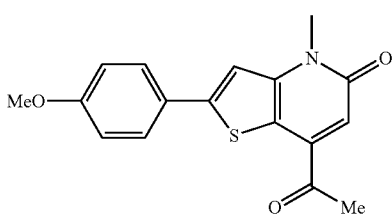 [SMILES: COc1ccc(-c2cc3c(s2)c(C(C)=O)cc(=O)n3C)cc1] |
| 11 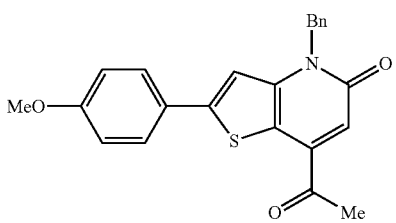 |
| 12 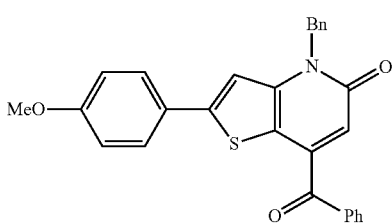 |

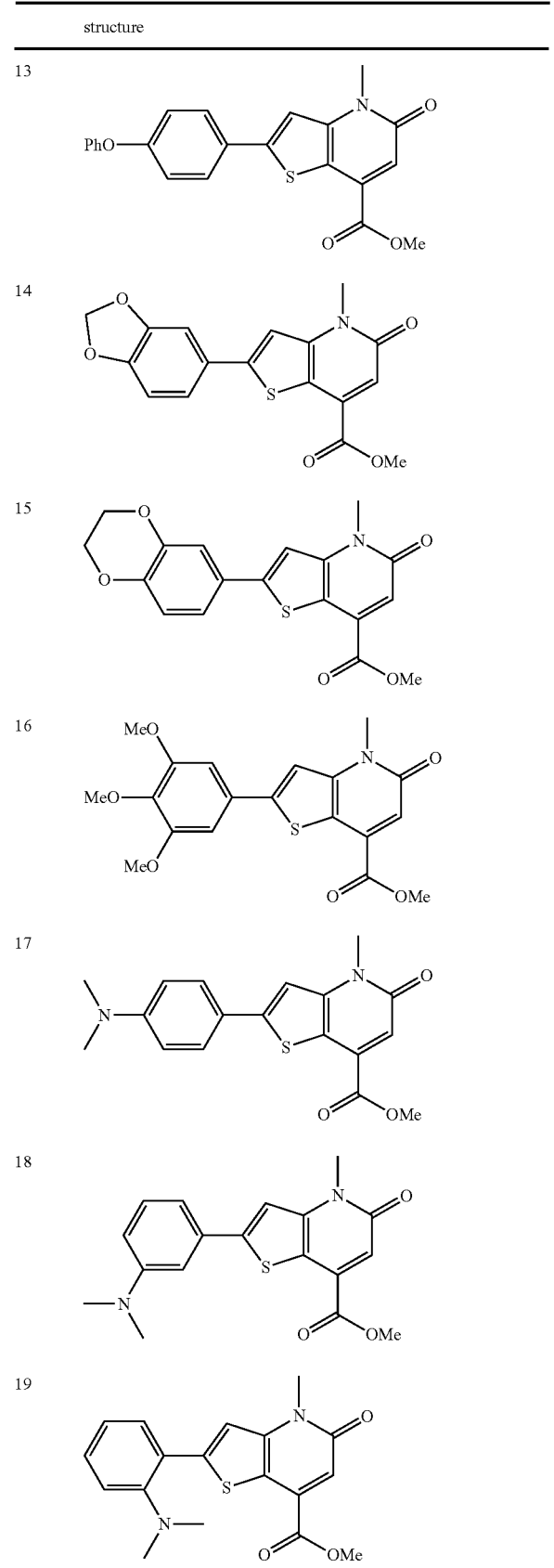
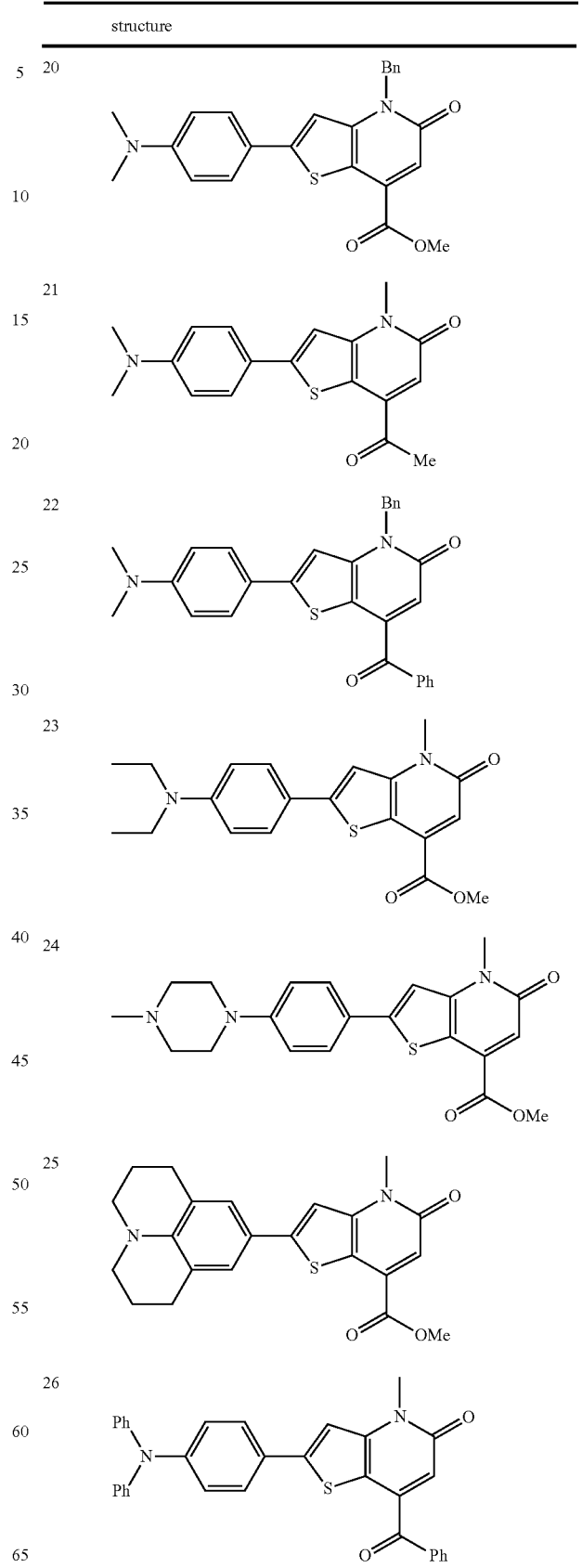

| | structure | |
|---|---|---|
| 27 | 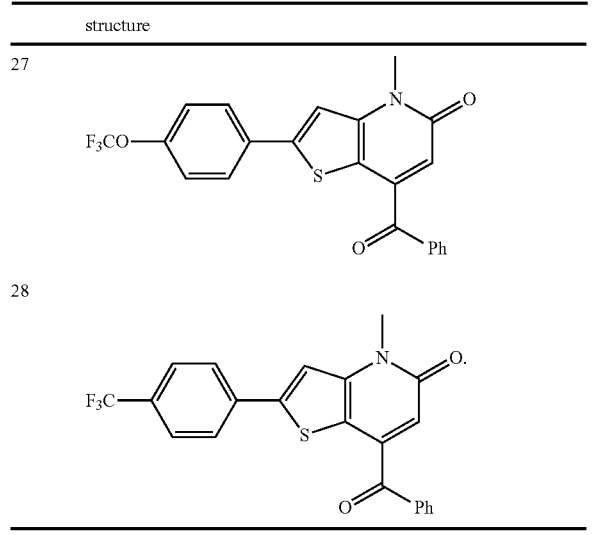 | 5 |
| | | 10 |
| 28 | 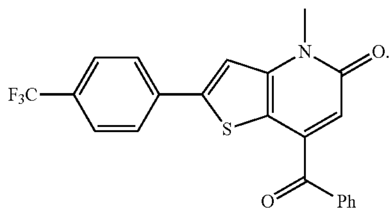 [SMILES: Cn1c(=O)cc(C(=O)c2ccccc2)c2sc(-c3ccc(C(F)(F)F)cc3)cc21] | 15 |
| | | 20 |

2. A method for preparing a compound of Chemical Formula 1 as illustrated in the following Reaction Scheme 1:

[Reaction Scheme 1]

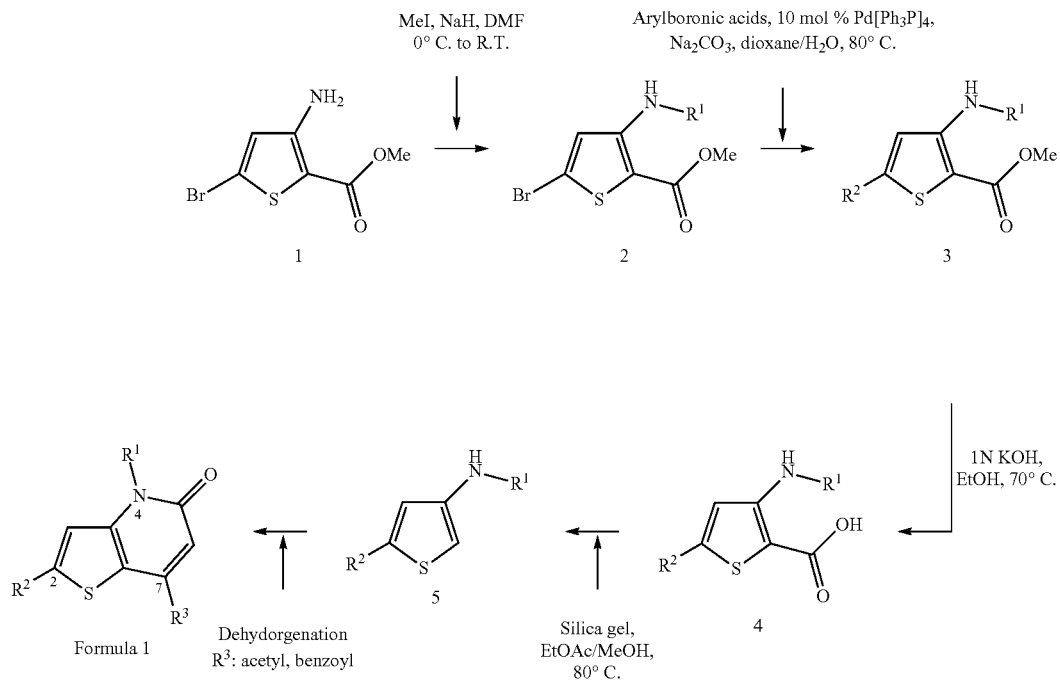

wherein,

R1 is H, Me, or Bn,

R2 is an aryl of $C_6$-$C_{10}$ that may be substituted or unsubstituted with one or more substituents overlappingly selected from the group consisting of a linear or branched alkyl of $C_1$-$C_{10}$, an amine, a 5- or 6-membered aromatic or non-aromatic heterocylic ring amine bearing one or two N atoms, $F_3CO$—, an aryl of $C_6$-$C_{10}$, and an alkoxy of $C_1$-$C_4$; and R3 is

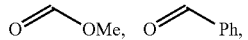

H, Me, or Ph.

3. A method for preparing a compound of Chemical Formula 1 as illustrated in the following Reaction Scheme 2:

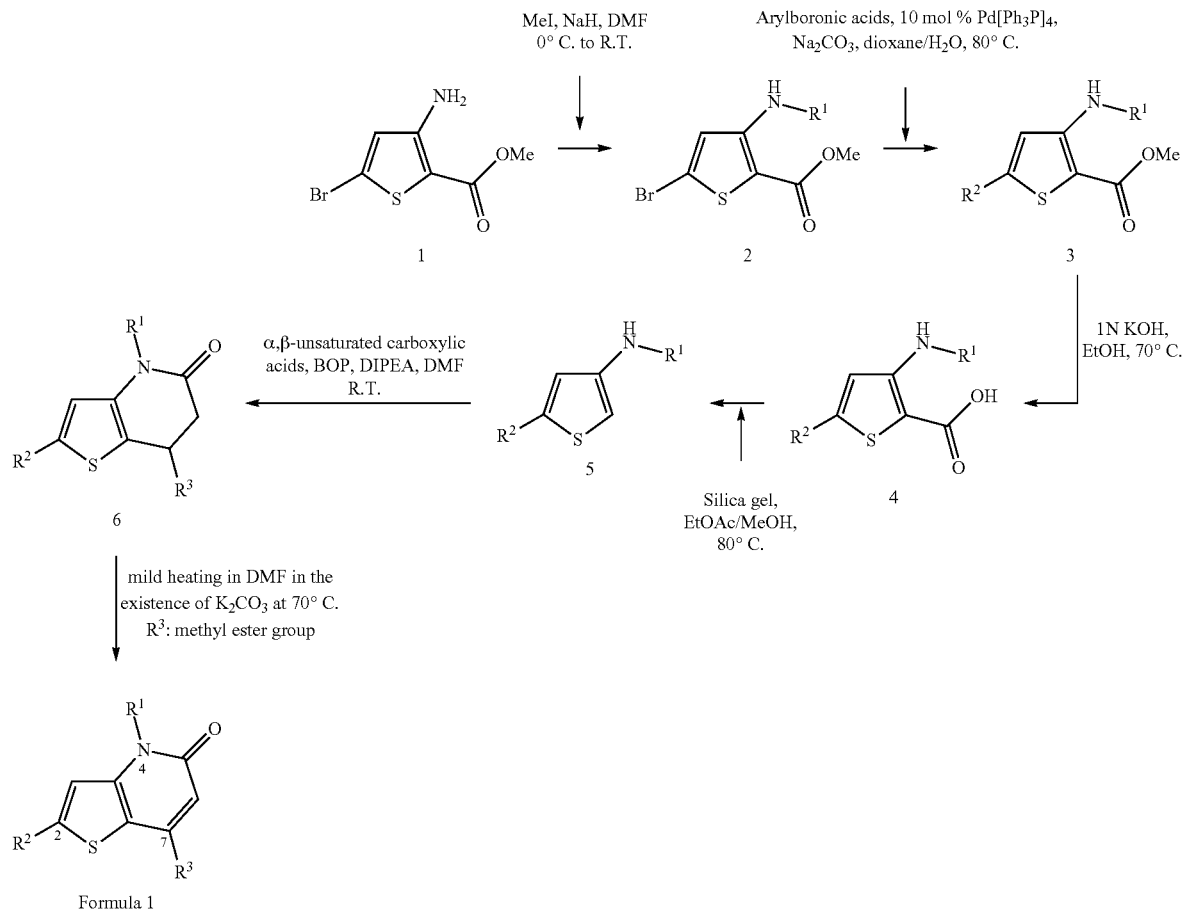

[Reaction Scheme 2]

Formula 1 wherein,
R1 is H, Me, or Bn,
R2 is an aryl of $C_6$-$C_{10}$ that may be substituted or unsubstituted with one or more substituents overlappingly selected from the group consisting of a linear or branched alkyl of $C_1$-$C_{10}$, an amine, a 5- or 6-membered aromatic or non-aromatic heterocylic ring amine bearing one or two N atoms, $F_3CO$—, an aryl of $C_6$-$C_{10}$, and an alkoxy of $C_1$-$C_4$; and R3 is H, Me, or Ph.

4. A method for preparing the compound of Chemical Formula 1 as illustrated in the following Reaction Scheme 3:

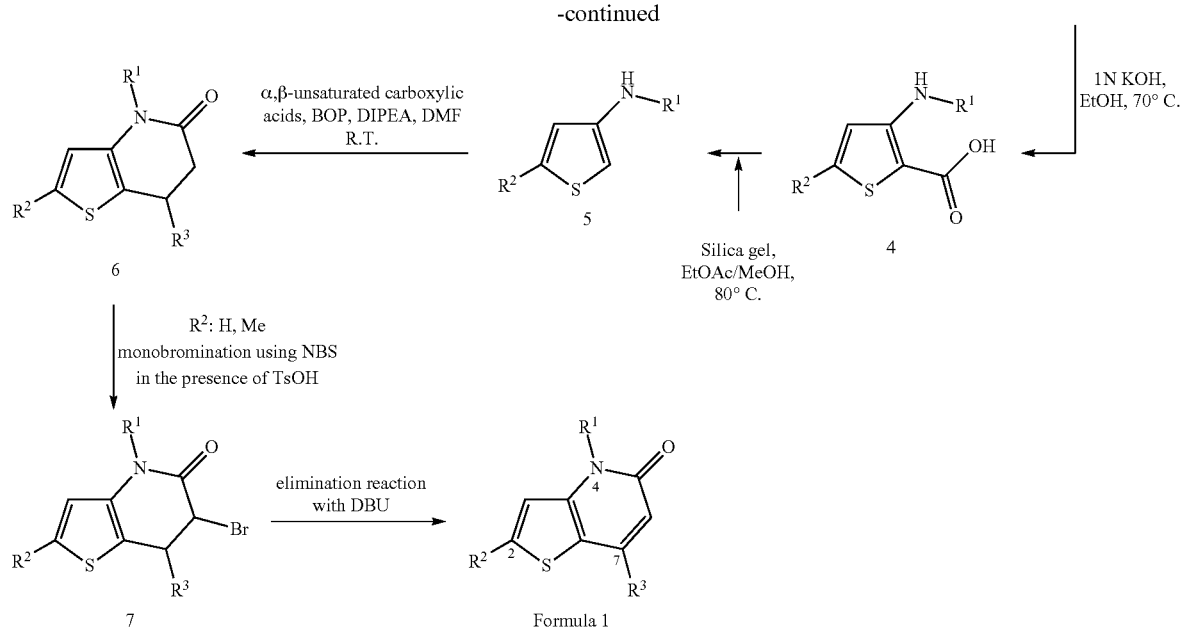

wherein,

R1 is H, Me, or Bn,

R2 is an aryl of $C_6$-$C_{10}$ that may be substituted or unsubstituted with one or more substituents overlappingly selected from the group consisting of a linear or branched alkyl of $C_1$-$C_{10}$, an amine, a 5- or 6-membered aromatic or non-aromatic heterocylic ring amine bearing one or two N atoms, $F_3CO—$, an aryl of $C_6$-$C_{10}$, and an alkoxy of $C_1$-$C_4$; and R3 is

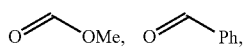

H, Me, or Ph.

5. A fluorescent composition, comprising the compound of claim 1, an enantiomer or diastereomer thereof, or an acid or base addition salt thereof as an active ingredient.

6. A biomolecular labeling or analyzing kit comprising the fluorescent composition of claim 5.

7. A pH sensing composition, comprising the compound of claim 1, an enantiomer or diastereomer thereof, or an acid or base addition salt thereof as a fluorescent dye.

8. A pH sensor, comprising the pH sensing composition of claim 7.

* * * * *